US012779228B2

(12) United States Patent
Drake

(10) Patent No.: US 12,779,228 B2
(45) Date of Patent: Nov. 3, 2026

(54) IMPLANTABLE MEDICAL DEVICE DELIVERY FOR CARDIAC THERAPY

(71) Applicant: MEDTRONIC, INC., Minneapolis, MN (US)

(72) Inventor: Ronald Drake, St. Louis Park, MN (US)

(73) Assignee: Medtronic, Inc., Minneapolis, MN (US)

(*) Notice: Subject to any disclaimer, the term of this patent is extended or adjusted under 35 U.S.C. 154(b) by 225 days.

(21) Appl. No.: 18/667,455

(22) Filed: May 17, 2024

(65) Prior Publication Data

US 2024/0299755 A1 Sep. 12, 2024

Related U.S. Application Data

(62) Division of application No. 16/227,774, filed on Dec. 20, 2018, now abandoned.

(51) Int. Cl.
*A61N 1/368* (2006.01)
*A61B 5/361* (2021.01)
(Continued)

(52) U.S. Cl.
CPC ....... *A61N 1/3682* (2013.01); *A61N 1/36585* (2013.01); *A61N 1/3684* (2013.01); (Continued)

(58) Field of Classification Search
None
See application file for complete search history.

(56) References Cited

U.S. PATENT DOCUMENTS 3,835,864 A 9/1974 Rasor et al.
3,865,118 A 2/1975 Bures
(Continued)

FOREIGN PATENT DOCUMENTS

AU 2008279789 B2 10/2011
AU 2008329620 B2 5/2014
(Continued)

OTHER PUBLICATIONS

US 8,886,318 B2, 11/2014, Jacobson et al. (withdrawn)
(Continued)

*Primary Examiner* — Manolis Pahakis
(74) *Attorney, Agent, or Firm* — Mueting Raasch Group

(57) ABSTRACT

Various techniques include advancing an implantable medical device comprising a tissue-piercing electrode toward the triangle of Koch region of the right atrium or through the coronary sinus to deliver cardiac therapy to or sense electrical activity of the left ventricle in the basal region, septal region, or basal-septal region of the left ventricular myocardium of a patient's heart. The tissue-piercing electrode may include an imagable material. The implantable medical device may include an imagable member made of an imagable material coupled to a housing or a lead of the implantable medical device. Image information representing the patient's heart and the imagable material may be acquired using two-dimensional imaging. Orientation information representing the implantable medical device may be generated based on the acquired image information.

20 Claims, 25 Drawing Sheets

(51) Int. Cl.

| | |
|---|---|
| ***A61B 5/363*** | (2021.01) |
| ***A61N 1/365*** | (2006.01) |
| ***A61N 1/37*** | (2006.01) |
| ***A61N 1/372*** | (2006.01) |
| ***A61N 1/375*** | (2006.01) |
| ***A61N 1/378*** | (2006.01) |
| ***A61N 1/39*** | (2006.01) |

(52) U.S. Cl.

CPC ....... *A61N 1/37288* (2013.01); *A61N 1/3787* (2013.01); *A61B 5/361* (2021.01); *A61B 5/363* (2021.01); *A61N 1/36578* (2013.01); *A61N 1/3706* (2013.01); *A61N 1/37217* (2013.01); *A61N 1/37512* (2017.08); *A61N 1/3756* (2013.01); *A61N 1/3962* (2013.01)

(56) References Cited

U.S. PATENT DOCUMENTS 3,943,936 A 3/1976 Rasor et al.
3,949,757 A 4/1976 Sabel
4,142,530 A 3/1979 Wittkampf
4,151,513 A 4/1979 Menken et al.
4,157,720 A 6/1979 Greatbatch
RE30,366 E 8/1980 Rasor et al.
4,243,045 A 1/1981 Mass
4,250,884 A 2/1981 Hartlaub et al.
4,256,115 A 3/1981 Bilitch
4,263,919 A 4/1981 Levin
4,280,502 A 7/1981 Baker, Jr. et al.
4,289,144 A 9/1981 Gilman
4,310,000 A 1/1982 Lindemans
4,312,354 A 1/1982 Walters
4,323,081 A 4/1982 Wiebusch
4,332,259 A 6/1982 McCorkle, Jr.
4,357,946 A 11/1982 Dutcher et al.
4,365,639 A 12/1982 Goldreyer
4,374,382 A 2/1983 Markowitz et al.
4,393,883 A 7/1983 Smyth et al.
4,440,173 A 4/1984 Hudziak et al.
4,476,868 A 10/1984 Thompson
4,479,500 A 10/1984 Smits
4,522,208 A 6/1985 Buffet
4,537,200 A 8/1985 Widrow
4,546,777 A 10/1985 Groch et al.
4,556,063 A 12/1985 Thompson et al.
4,562,841 A 1/1986 Brockway et al.
4,574,814 A 3/1986 Buffet
4,593,702 A 6/1986 Kepski et al.
4,593,955 A 6/1986 Leiber
4,630,611 A 12/1986 King
4,635,639 A 1/1987 Hakala et al.
4,674,508 A 6/1987 DeCote
4,712,554 A 12/1987 Garson
4,729,376 A 3/1988 DeCote
4,754,753 A 7/1988 King
4,759,366 A 7/1988 Callaghan
4,776,338 A 10/1988 Lekholm et al.
4,787,389 A 11/1988 Tarjan
4,793,353 A 12/1988 Borkan
4,819,662 A 4/1989 Heil et al.
4,830,006 A 5/1989 Haluska et al.
4,858,610 A 8/1989 Callaghan et al.
4,865,037 A 9/1989 Chin et al.
4,886,064 A 12/1989 Strandberg
4,887,609 A 12/1989 Cole, Jr.
4,928,688 A 5/1990 Mower
4,953,564 A 9/1990 Berthelsen
4,967,746 A 11/1990 Vandegriff
4,987,897 A 1/1991 Funke
4,989,602 A 2/1991 Sholder et al.
5,012,806 A 5/1991 De Bellis
5,036,849 A 8/1991 Hauck et al.
5,040,534 A 8/1991 Mann et al.
5,058,581 A 10/1991 Silvian
5,078,134 A 1/1992 Heilman et al.
5,109,845 A 5/1992 Yuuchi et al.
5,113,859 A 5/1992 Funke
5,113,869 A 5/1992 Nappholz et al.
5,117,824 A 6/1992 Keimel et al.
5,127,401 A 7/1992 Grievous et al.
5,133,353 A 7/1992 Hauser
5,144,950 A 9/1992 Stoop et al.
5,154,170 A 10/1992 Bennett et al.
5,170,784 A 12/1992 Ramon et al.
5,174,289 A 12/1992 Cohen
5,179,945 A 1/1993 Van Hofwegen et al.
5,193,539 A 3/1993 Schulman et al.
5,193,540 A 3/1993 Schulman et al.
5,241,961 A 9/1993 Henry
5,243,977 A 9/1993 Trabucco et al.
5,255,692 A 10/1993 Neubauer et al.
5,259,387 A 11/1993 dePinto
5,269,326 A 12/1993 Verrier
5,284,136 A 2/1994 Hauck et al.
5,300,107 A 4/1994 Stokes et al.
5,301,677 A 4/1994 Hsung
5,305,760 A 4/1994 McKown et al.
5,312,439 A 5/1994 Loeb
5,313,953 A 5/1994 Yomtov et al.
5,314,459 A 5/1994 Swanson et al.
5,318,594 A 6/1994 Limousin et al.
5,318,597 A 6/1994 Hauck et al.
5,324,316 A 6/1994 Schulman et al.
5,331,966 A 7/1994 Bennett et al.
5,334,222 A 8/1994 Salo et al.
5,342,408 A 8/1994 Decoriolis et al.
5,370,667 A 12/1994 Alt
5,372,606 A 12/1994 Lang et al.
5,376,106 A 12/1994 Stahmann et al.
5,383,915 A 1/1995 Adams
5,388,578 A 2/1995 Yomtov et al.
5,404,877 A 4/1995 Nolan et al.
5,405,367 A 4/1995 Schulman et al.
5,411,031 A 5/1995 Yomtov
5,411,525 A 5/1995 Swanson et al.
5,411,535 A 5/1995 Fujii et al.
5,456,691 A 10/1995 Snell
5,458,622 A 10/1995 Alt
5,466,246 A 11/1995 Silvian
5,468,254 A 11/1995 Hahn et al.
5,472,453 A 12/1995 Alt
5,522,866 A 6/1996 Fernald
5,540,727 A 7/1996 Tockman et al.
5,545,186 A 8/1996 Olson et al.
5,545,202 A 8/1996 Dahl et al.
5,554,177 A 9/1996 Kieval et al.
5,562,711 A 10/1996 Yerich et al.
5,571,146 A 11/1996 Jones et al.
5,591,214 A 1/1997 Lu
5,620,466 A 4/1997 Haefner et al.
5,634,938 A 6/1997 Swanson et al.
5,649,968 A 7/1997 Alt et al.
5,662,688 A 9/1997 Haefner et al.
5,674,259 A 10/1997 Gray
5,683,426 A 11/1997 Greenhut et al.
5,683,432 A 11/1997 Goedeke et al.
5,706,823 A 1/1998 Wodlinger
5,709,215 A 1/1998 Perttu et al.
5,720,770 A 2/1998 Nappholz et al.
5,728,140 A 3/1998 Salo et al.
5,728,154 A 3/1998 Crossett et al.
5,741,314 A 4/1998 Daly et al.
5,741,315 A 4/1998 Lee et al.
5,749,909 A 5/1998 Schroeppel et al.
5,752,976 A 5/1998 Duffin et al.
5,752,977 A 5/1998 Grievous et al.
5,755,736 A 5/1998 Gillberg et al.
5,759,199 A 6/1998 Snell et al.
5,774,501 A 6/1998 Halpern et al.
5,792,195 A 8/1998 Carlson et al.
5,792,202 A 8/1998 Rueter
5,792,203 A 8/1998 Schroeppel
5,792,205 A 8/1998 Alt et al.

(56) References Cited

U.S. PATENT DOCUMENTS

| | | | |
|---|---|---|---|
| 5,792,208 | A | 8/1998 | Gray |
| 5,814,089 | A | 9/1998 | Stokes et al. |
| 5,817,130 | A | 10/1998 | Cox et al. |
| 5,827,216 | A | 10/1998 | Igo et al. |
| 5,836,985 | A | 11/1998 | Goyal et al. |
| 5,836,987 | A | 11/1998 | Baumann et al. |
| 5,842,977 | A | 12/1998 | Lesho et al. |
| 5,855,593 | A | 1/1999 | Olson et al. |
| 5,873,894 | A | 2/1999 | Vandegriff et al. |
| 5,891,184 | A | 4/1999 | Lee et al. |
| 5,897,586 | A | 4/1999 | Molina |
| 5,899,876 | A | 5/1999 | Flower |
| 5,899,928 | A | 5/1999 | Sholder et al. |
| 5,919,214 | A | 7/1999 | Ciciarelli et al. |
| 5,928,271 | A | 7/1999 | Hess et al. |
| 5,935,078 | A | 8/1999 | Feierbach |
| 5,941,906 | A | 8/1999 | Barreras et al. |
| 5,944,744 | A | 8/1999 | Paul et al. |
| 5,954,757 | A | 9/1999 | Gray |
| 5,978,713 | A | 11/1999 | Prutchi et al. |
| 5,991,660 | A | 11/1999 | Goyal |
| 5,991,661 | A | 11/1999 | Park et al. |
| 5,999,848 | A | 12/1999 | Gord et al. |
| 5,999,857 | A | 12/1999 | Weijand et al. |
| 6,016,445 | A | 1/2000 | Baura |
| 6,026,320 | A | 2/2000 | Carlson et al. |
| 6,029,085 | A | 2/2000 | Olson et al. |
| 6,041,250 | A | 3/2000 | dePinto |
| 6,044,298 | A | 3/2000 | Salo et al. |
| 6,044,300 | A | 3/2000 | Gray |
| 6,055,454 | A | 4/2000 | Heemels |
| 6,073,050 | A | 6/2000 | Griffith |
| 6,076,016 | A | 6/2000 | Feierbach |
| 6,077,236 | A | 6/2000 | Cunningham |
| 6,080,187 | A | 6/2000 | Alt et al. |
| 6,083,248 | A | 7/2000 | Thompson |
| 6,106,551 | A | 8/2000 | Crossett et al. |
| 6,115,636 | A | 9/2000 | Ryan |
| 6,128,526 | A | 10/2000 | Stadler et al. |
| 6,132,456 | A | 10/2000 | Sommer et al. |
| 6,141,581 | A | 10/2000 | Olson et al. |
| 6,141,588 | A | 10/2000 | Cox et al. |
| 6,141,592 | A | 10/2000 | Pauly |
| 6,144,879 | A | 11/2000 | Gray |
| 6,162,195 | A | 12/2000 | Igo et al. |
| 6,164,284 | A | 12/2000 | Schulman et al. |
| 6,167,310 | A | 12/2000 | Grevious |
| 6,201,993 | B1 | 3/2001 | Kruse et al. |
| 6,208,894 | B1 | 3/2001 | Schulman et al. |
| 6,211,799 | B1 | 4/2001 | Post et al. |
| 6,221,011 | B1 | 4/2001 | Bardy |
| 6,240,316 | B1 | 5/2001 | Richmond et al. |
| 6,240,317 | B1 | 5/2001 | Villaseca et al. |
| 6,256,534 | B1 | 7/2001 | Dahl |
| 6,259,947 | B1 | 7/2001 | Olson et al. |
| 6,266,558 | B1 | 7/2001 | Gozani et al. |
| 6,266,567 | B1 | 7/2001 | Ishikawa et al. |
| 6,270,457 | B1 | 8/2001 | Bardy |
| 6,272,377 | B1 | 8/2001 | Sweeney et al. |
| 6,273,856 | B1 | 8/2001 | Sun et al. |
| 6,277,072 | B1 | 8/2001 | Bardy |
| 6,280,380 | B1 | 8/2001 | Bardy |
| 6,285,903 | B1 | 9/2001 | Rosenthal et al. |
| 6,285,907 | B1 | 9/2001 | Kramer et al. |
| 6,292,698 | B1 | 9/2001 | Duffin et al. |
| 6,295,473 | B1 | 9/2001 | Rosar |
| 6,297,943 | B1 | 10/2001 | Carson |
| 6,298,271 | B1 | 10/2001 | Weijand |
| 6,307,751 | B1 | 10/2001 | Bodony et al. |
| 6,312,378 | B1 | 11/2001 | Bardy |
| 6,315,721 | B2 | 11/2001 | Schulman et al. |
| 6,336,903 | B1 | 1/2002 | Bardy |
| 6,345,202 | B2 | 2/2002 | Richmond et al. |
| 6,351,667 | B1 | 2/2002 | Godie |
| 6,351,669 | B1 | 2/2002 | Hartley et al. |
| 6,353,759 | B1 | 3/2002 | Hartley et al. |
| 6,358,203 | B2 | 3/2002 | Bardy |
| 6,361,780 | B1 | 3/2002 | Ley et al. |
| 6,368,284 | B1 | 4/2002 | Bardy |
| 6,371,922 | B1 | 4/2002 | Baumann et al. |
| 6,393,316 | B1 | 5/2002 | Gillberg et al. |
| 6,398,728 | B1 | 6/2002 | Bardy |
| 6,400,982 | B2 | 6/2002 | Sweeney et al. |
| 6,400,990 | B1 | 6/2002 | Silvian |
| 6,408,208 | B1 | 6/2002 | Sun |
| 6,409,674 | B1 | 6/2002 | Brockway et al. |
| 6,411,848 | B2 | 6/2002 | Kramer et al. |
| 6,424,865 | B1 | 7/2002 | Ding |
| 6,434,429 | B1 | 8/2002 | Kraus et al. |
| 6,438,410 | B2 | 8/2002 | Hsu et al. |
| 6,438,417 | B1 | 8/2002 | Rockwell et al. |
| 6,438,421 | B1 | 8/2002 | Stahmann et al. |
| 6,440,066 | B1 | 8/2002 | Bardy |
| 6,441,747 | B1 | 8/2002 | Khair et al. |
| 6,442,426 | B1 | 8/2002 | Kroll |
| 6,442,432 | B2 | 8/2002 | Lee |
| 6,443,891 | B1 | 9/2002 | Grevious |
| 6,445,953 | B1 | 9/2002 | Bulkes et al. |
| 6,453,200 | B1 | 9/2002 | Koslar |
| 6,459,929 | B1 | 10/2002 | Hopper et al. |
| 6,470,215 | B1 | 10/2002 | Kraus et al. |
| 6,471,645 | B1 | 10/2002 | Warkentin et al. |
| 6,480,745 | B2 | 11/2002 | Nelson et al. |
| 6,487,443 | B2 | 11/2002 | Olson et al. |
| 6,490,487 | B1 | 12/2002 | Kraus et al. |
| 6,498,951 | B1 | 12/2002 | Larson et al. |
| 6,507,755 | B1 | 1/2003 | Gozani et al. |
| 6,507,759 | B1 | 1/2003 | Prutchi et al. |
| 6,508,771 | B1 | 1/2003 | Padmanabhan et al. |
| 6,512,940 | B1 | 1/2003 | Brabec et al. |
| 6,522,915 | B1 | 2/2003 | Ceballos et al. |
| 6,526,311 | B2 | 2/2003 | Begemann |
| 6,539,253 | B2 | 3/2003 | Thompson et al. |
| 6,542,775 | B2 | 4/2003 | Ding et al. |
| 6,553,258 | B2 | 4/2003 | Stahmann et al. |
| 6,561,975 | B1 | 5/2003 | Pool et al. |
| 6,564,807 | B1 | 5/2003 | Schulman et al. |
| 6,574,506 | B2 | 6/2003 | Kramer et al. |
| 6,584,351 | B1 | 6/2003 | Ekwall |
| 6,584,352 | B2 | 6/2003 | Combs et al. |
| 6,597,948 | B1 | 7/2003 | Rockwell et al. |
| 6,597,951 | B2 | 7/2003 | Kramer et al. |
| 6,622,046 | B2 | 9/2003 | Fraley et al. |
| 6,623,518 | B2 | 9/2003 | Thompson et al. |
| 6,628,985 | B2 | 9/2003 | Sweeney et al. |
| 6,647,292 | B1 | 11/2003 | Bardy et al. |
| 6,666,844 | B1 | 12/2003 | Igo et al. |
| 6,689,117 | B2 | 2/2004 | Sweeney et al. |
| 6,690,959 | B2 | 2/2004 | Thompson |
| 6,694,189 | B2 | 2/2004 | Begemann |
| 6,704,602 | B2 | 3/2004 | Berg et al. |
| 6,718,212 | B2 | 4/2004 | Parry et al. |
| 6,721,597 | B1 | 4/2004 | Bardy et al. |
| 6,738,670 | B1 | 5/2004 | Almendinger et al. |
| 6,746,797 | B2 | 6/2004 | Benson et al. |
| 6,749,566 | B2 | 6/2004 | Russ |
| 6,754,528 | B2 | 6/2004 | Bardy et al. |
| 6,758,810 | B2 | 7/2004 | Lebel et al. |
| 6,763,269 | B2 | 7/2004 | Cox |
| 6,778,860 | B2 | 8/2004 | Ostroff et al. |
| 6,788,971 | B1 | 9/2004 | Sloman et al. |
| 6,788,974 | B2 | 9/2004 | Bardy et al. |
| 6,804,558 | B2 | 10/2004 | Haller et al. |
| 6,807,442 | B1 | 10/2004 | Myklebust et al. |
| 6,847,844 | B2 | 1/2005 | Sun et al. |
| 6,869,404 | B2 | 3/2005 | Schulhauser et al. |
| 6,871,095 | B2 | 3/2005 | Stahmann et al. |
| 6,871,096 | B2 | 3/2005 | Hill |
| 6,878,112 | B2 | 4/2005 | Linberg et al. |
| 6,885,889 | B2 | 4/2005 | Chinchoy |
| 6,892,094 | B2 | 5/2005 | Ousdigian et al. |
| 6,897,788 | B2 | 5/2005 | Khair et al. |
| 6,904,315 | B2 | 6/2005 | Panken et al. |
| 6,922,592 | B2 | 7/2005 | Thompson et al. |

(56) References Cited

U.S. PATENT DOCUMENTS 6,931,282 B2 8/2005 Esler
6,931,286 B2 8/2005 Sigg et al.
6,934,585 B1 8/2005 Schloss et al.
6,941,169 B2 9/2005 Pappu
6,957,107 B2 10/2005 Rogers et al.
6,978,176 B2 12/2005 Lattouf
6,980,675 B2 12/2005 Evron et al.
6,985,773 B2 1/2006 Von Arx et al.
6,990,375 B2 1/2006 Kloss et al.
6,993,389 B2 1/2006 Ding et al.
7,001,366 B2 2/2006 Ballard
7,003,350 B2 2/2006 Denker et al.
7,006,864 B2 2/2006 Echt et al.
7,013,176 B2 3/2006 Ding et al.
7,013,178 B2 3/2006 Reinke et al.
7,027,871 B2 4/2006 Burnes et al.
7,031,711 B2 4/2006 Brown et al.
7,031,771 B2 4/2006 Brown et al.
7,035,684 B2 4/2006 Lee et al.
7,050,849 B2 5/2006 Echt et al.
7,060,031 B2 6/2006 Webb et al.
7,063,693 B2 6/2006 Guenst
7,082,336 B2 7/2006 Ransbury et al.
7,085,606 B2 8/2006 Flach et al.
7,092,758 B2 8/2006 Sun et al.
7,110,824 B2 9/2006 Amundson et al.
7,120,504 B2 * 10/2006 Osypka .................. A61N 1/059
607/131
7,130,681 B2 10/2006 Gebhardt et al.
7,139,613 B2 11/2006 Reinke et al.
7,142,912 B2 11/2006 Wagner et al.
7,146,225 B2 12/2006 Guenst et al.
7,146,226 B2 12/2006 Lau et al.
7,149,581 B2 12/2006 Goedeke
7,149,588 B2 12/2006 Lau et al.
7,158,839 B2 1/2007 Lau
7,162,307 B2 1/2007 Patrias
7,164,952 B2 1/2007 Lau et al.
7,177,700 B1 2/2007 Cox
7,177,704 B2 * 2/2007 Laske ................... A61N 1/057
600/375
7,181,284 B2 2/2007 Burnes et al.
7,181,505 B2 2/2007 Haller et al.
7,184,830 B2 2/2007 Echt et al.
7,186,214 B2 3/2007 Ness
7,191,015 B2 3/2007 Lamson et al.
7,200,437 B1 4/2007 Nabutovsky et al.
7,200,439 B2 4/2007 Zdeblick et al.
7,206,423 B1 4/2007 Feng et al.
7,209,785 B2 4/2007 Kim et al.
7,209,790 B2 4/2007 Thompson et al.
7,211,884 B1 5/2007 Davis et al.
7,212,871 B1 5/2007 Morgan
7,226,440 B2 6/2007 Gelfand et al.
7,228,183 B2 6/2007 Sun et al.
7,231,248 B2 6/2007 Kramer et al.
7,231,253 B2 6/2007 Tidemand et al.
7,236,821 B2 6/2007 Cates et al.
7,236,829 B1 6/2007 Farazi et al.
7,254,448 B2 8/2007 Almendinger et al.
7,260,436 B2 8/2007 Kilgore et al.
7,270,669 B1 9/2007 Sra
7,272,448 B1 9/2007 Morgan et al.
7,277,755 B1 10/2007 Falkenberg et al.
7,280,872 B1 10/2007 Mosesov et al.
7,286,866 B2 10/2007 Okerlund et al.
7,288,096 B2 10/2007 Chin
7,289,847 B1 10/2007 Gill et al.
7,289,852 B2 10/2007 Helfinstine et al.
7,289,853 B1 10/2007 Campbell et al.
7,289,855 B2 10/2007 Nghiem et al.
7,302,294 B2 11/2007 Kamath et al.
7,305,266 B1 12/2007 Kroll
7,307,321 B1 12/2007 Avanzino
7,308,297 B2 12/2007 Reddy et al.
7,308,299 B2 12/2007 Burrell et al.
7,310,556 B2 12/2007 Bulkes
7,317,950 B2 1/2008 Lee
7,319,905 B1 1/2008 Morgan et al.
7,321,677 B2 1/2008 Evron et al.
7,321,798 B2 1/2008 Muhlenberg et al.
7,333,853 B2 2/2008 Mazar et al.
7,336,994 B2 2/2008 Hettrick et al.
7,346,381 B2 3/2008 Okerlund et al.
7,346,393 B2 3/2008 Spinelli et al.
7,347,819 B2 3/2008 Lebel et al.
7,366,572 B2 4/2008 Heruth et al.
7,373,207 B2 5/2008 Lattouf
7,384,403 B2 6/2008 Sherman
7,386,342 B1 6/2008 Falkenberg et al.
7,392,090 B2 6/2008 Sweeney et al.
7,406,105 B2 7/2008 DelMain et al.
7,406,349 B2 7/2008 Seeberger et al.
7,410,497 B2 8/2008 Hastings et al.
7,425,200 B2 9/2008 Brockway et al.
7,433,739 B1 10/2008 Salys et al.
7,454,248 B2 11/2008 Burrell et al.
7,496,409 B2 2/2009 Greenhut et al.
7,496,410 B2 2/2009 Heil
7,499,743 B2 3/2009 Vass et al.
7,502,652 B2 3/2009 Gaunt et al.
7,512,448 B2 3/2009 Malick et al.
7,515,969 B2 4/2009 Tockman et al.
7,526,342 B2 4/2009 Chin et al.
7,529,589 B2 5/2009 Williams et al.
7,532,933 B2 5/2009 Hastings et al.
7,536,222 B2 5/2009 Bardy et al.
7,536,224 B2 5/2009 Ritscher et al.
7,539,541 B2 5/2009 Quiles et al.
7,544,197 B2 6/2009 Kelsch et al.
7,546,166 B2 6/2009 Michels et al.
7,558,626 B2 7/2009 Corbucci
7,558,631 B2 7/2009 Cowan et al.
7,565,190 B2 7/2009 Okerlund et al.
7,565,195 B1 7/2009 Kroll et al.
7,584,002 B2 9/2009 Burnes et al.
7,587,074 B2 9/2009 Zarkh et al.
7,590,455 B2 9/2009 Heruth et al.
7,599,730 B2 10/2009 Hunter et al.
7,606,621 B2 10/2009 Brisken et al.
7,610,088 B2 10/2009 Chinchoy
7,610,092 B2 10/2009 Cowan et al.
7,610,099 B2 10/2009 Almendinger et al.
7,610,104 B2 10/2009 Kaplan et al.
7,613,500 B2 11/2009 Vass et al.
7,616,991 B2 11/2009 Mann et al.
7,617,001 B2 11/2009 Penner et al.
7,617,007 B2 11/2009 Williams et al.
7,630,764 B2 12/2009 Ding et al.
7,630,767 B1 12/2009 Poore et al.
7,634,313 B1 12/2009 Kroll et al.
7,635,541 B2 12/2009 Scott et al.
7,637,867 B2 12/2009 Zdeblick
7,640,057 B2 12/2009 Libbus et al.
7,640,060 B2 12/2009 Zdeblick
7,647,109 B2 1/2010 Hastings et al.
7,650,186 B2 1/2010 Hastings et al.
7,657,311 B2 2/2010 Bardy et al.
7,657,313 B2 2/2010 Rom
7,668,596 B2 2/2010 Von Arx et al.
7,682,316 B2 3/2010 Anderson et al.
7,691,047 B2 4/2010 Ferrari
7,702,392 B2 4/2010 Echt et al.
7,706,879 B2 4/2010 Burnes et al.
7,713,194 B2 5/2010 Zdeblick
7,713,195 B2 5/2010 Zdeblick
7,729,783 B2 6/2010 Michels et al.
7,734,333 B2 6/2010 Ghanem et al.
7,734,343 B2 6/2010 Ransbury et al.
7,738,958 B2 6/2010 Zdeblick et al.
7,738,964 B2 6/2010 Von Arx et al.
7,742,629 B2 6/2010 Zarkh et al.
7,742,812 B2 6/2010 Ghanem et al.
7,742,816 B2 6/2010 Masoud et al.

(56) References Cited

U.S. PATENT DOCUMENTS

| | | | |
|---|---|---|---|
| 7,742,822 | B2 | 6/2010 | Masoud et al. |
| 7,743,151 | B2 | 6/2010 | Vallapureddy et al. |
| 7,747,047 | B2 | 6/2010 | Okerlund et al. |
| 7,747,335 | B2 | 6/2010 | Williams |
| 7,751,881 | B2 | 7/2010 | Cowan et al. |
| 7,758,521 | B2 | 7/2010 | Morris et al. |
| 7,761,150 | B2 | 7/2010 | Ghanem et al. |
| 7,761,164 | B2 | 7/2010 | Verhoef et al. |
| 7,765,001 | B2 | 7/2010 | Echt et al. |
| 7,769,452 | B2 | 8/2010 | Ghanem et al. |
| 7,778,685 | B2 | 8/2010 | Evron et al. |
| 7,778,686 | B2 | 8/2010 | Vass et al. |
| 7,783,362 | B2 | 8/2010 | Whitehurst et al. |
| 7,792,588 | B2 | 9/2010 | Harding |
| 7,797,059 | B1 | 9/2010 | Bornzin et al. |
| 7,801,596 | B2 | 9/2010 | Fischell et al. |
| 7,809,438 | B2 | 10/2010 | Echt et al. |
| 7,813,785 | B2 | 10/2010 | Okerlund et al. |
| 7,840,281 | B2 | 11/2010 | Kveen et al. |
| 7,844,331 | B2 | 11/2010 | Li et al. |
| 7,844,348 | B2 | 11/2010 | Swoyer et al. |
| 7,846,088 | B2 | 12/2010 | Ness |
| 7,848,815 | B2 | 12/2010 | Brisken et al. |
| 7,848,823 | B2 | 12/2010 | Drasler et al. |
| 7,860,455 | B2 | 12/2010 | Fukumoto et al. |
| 7,871,433 | B2 | 1/2011 | Lattouf |
| 7,877,136 | B1 | 1/2011 | Moffitt et al. |
| 7,877,142 | B2 | 1/2011 | Moaddeb et al. |
| 7,877,144 | B2 | 1/2011 | Coles, Jr. et al. |
| 7,881,786 | B2 | 2/2011 | Jackson |
| 7,881,791 | B2 | 2/2011 | Sambelashvili et al. |
| 7,881,798 | B2 | 2/2011 | Miesel et al. |
| 7,881,810 | B1 | 2/2011 | Chitre et al. |
| 7,890,173 | B2 | 2/2011 | Brisken et al. |
| 7,890,181 | B2 | 2/2011 | Denzene et al. |
| 7,890,192 | B1 | 2/2011 | Kelsch et al. |
| 7,894,885 | B2 | 2/2011 | Bartal et al. |
| 7,894,894 | B2 | 2/2011 | Stadler et al. |
| 7,894,902 | B2 | 2/2011 | Rom |
| 7,894,907 | B2 | 2/2011 | Cowan et al. |
| 7,894,910 | B2 | 2/2011 | Cowan et al. |
| 7,894,915 | B1 | 2/2011 | Chitre et al. |
| 7,899,537 | B1 | 3/2011 | Kroll et al. |
| 7,899,541 | B2 | 3/2011 | Cowan et al. |
| 7,899,542 | B2 | 3/2011 | Cowan et al. |
| 7,899,554 | B2 | 3/2011 | Williams et al. |
| 7,901,360 | B1 | 3/2011 | Yang et al. |
| 7,904,170 | B2 | 3/2011 | Harding |
| 7,907,993 | B2 | 3/2011 | Ghanem et al. |
| 7,912,544 | B1 | 3/2011 | Min et al. |
| 7,920,928 | B1 | 4/2011 | Yang et al. |
| 7,925,343 | B1 | 4/2011 | Min et al. |
| 7,930,022 | B2 | 4/2011 | Zhang et al. |
| 7,930,027 | B2 | 4/2011 | Prakash et al. |
| 7,930,040 | B1 | 4/2011 | Kelsch et al. |
| 7,937,135 | B2 | 5/2011 | Ghanem et al. |
| 7,937,148 | B2 | 5/2011 | Jacobson |
| 7,937,161 | B2 | 5/2011 | Hastings et al. |
| 7,941,214 | B2 | 5/2011 | Kleckner et al. |
| 7,941,218 | B2 | 5/2011 | Sambelashvili et al. |
| 7,945,333 | B2 | 5/2011 | Jacobson |
| 7,946,997 | B2 | 5/2011 | Hubinette |
| 7,949,404 | B2 | 5/2011 | Hill |
| 7,949,405 | B2 | 5/2011 | Feher |
| 7,953,486 | B2 | 5/2011 | Daum et al. |
| 7,953,493 | B2 | 5/2011 | Fowler et al. |
| 7,962,202 | B2 | 6/2011 | Bhunia |
| 7,974,702 | B1 | 7/2011 | Fain et al. |
| 7,979,136 | B2 | 7/2011 | Young et al. |
| 7,983,753 | B2 | 7/2011 | Severin |
| 7,991,467 | B2 | 8/2011 | Markowitz et al. |
| 7,991,471 | B2 | 8/2011 | Ghanem et al. |
| 7,996,063 | B2 | 8/2011 | Vass et al. |
| 7,996,087 | B2 | 8/2011 | Cowan et al. |
| 8,000,791 | B2 | 8/2011 | Sunagawa et al. |
| 8,000,807 | B2 | 8/2011 | Morris et al. |
| 8,001,975 | B2 | 8/2011 | DiSilvestro et al. |
| 8,002,700 | B2 | 8/2011 | Ferek-Petric et al. |
| 8,002,718 | B2 | 8/2011 | Buchholtz et al. |
| 8,010,209 | B2 | 8/2011 | Jacobson |
| 8,019,419 | B1 | 9/2011 | Panescu et al. |
| 8,019,434 | B2 | 9/2011 | Quiles et al. |
| 8,027,727 | B2 | 9/2011 | Freeberg |
| 8,027,729 | B2 | 9/2011 | Sunagawa et al. |
| 8,032,219 | B2 | 10/2011 | Neumann et al. |
| 8,036,743 | B2 | 10/2011 | Savage et al. |
| 8,046,065 | B2 | 10/2011 | Burnes et al. |
| 8,046,079 | B2 | 10/2011 | Bange et al. |
| 8,046,080 | B2 | 10/2011 | Von Arx et al. |
| 8,050,297 | B2 | 11/2011 | Delmain et al. |
| 8,050,759 | B2 | 11/2011 | Stegemann et al. |
| 8,050,774 | B2 | 11/2011 | Kveen et al. |
| 8,055,345 | B2 | 11/2011 | Li et al. |
| 8,055,350 | B2 | 11/2011 | Roberts |
| 8,060,185 | B2 | 11/2011 | Hunter et al. |
| 8,060,212 | B1 | 11/2011 | Rios et al. |
| 8,065,018 | B2 | 11/2011 | Haubrich et al. |
| 8,068,920 | B2 | 11/2011 | Gaudiani |
| 8,073,542 | B2 | 12/2011 | Doerr |
| 8,078,278 | B2 | 12/2011 | Penner |
| 8,078,283 | B2 | 12/2011 | Cowan et al. |
| 8,095,123 | B2 | 1/2012 | Gray |
| 8,102,789 | B2 | 1/2012 | Rosar et al. |
| 8,103,359 | B2 | 1/2012 | Reddy |
| 8,103,361 | B2 | 1/2012 | Moser |
| 8,105,714 | B2 | 1/2012 | Schmidt et al. |
| 8,112,148 | B2 | 2/2012 | Giftakis et al. |
| 8,114,021 | B2 | 2/2012 | Robertson et al. |
| 8,121,680 | B2 | 2/2012 | Falkenberg et al. |
| 8,123,684 | B2 | 2/2012 | Zdeblick |
| 8,126,545 | B2 | 2/2012 | Flach et al. |
| 8,131,334 | B2 | 3/2012 | Lu et al. |
| 8,140,161 | B2 | 3/2012 | Willerton et al. |
| 8,142,363 | B1 | 3/2012 | Eigler |
| 8,145,308 | B2 | 3/2012 | Sambelashvili et al. |
| 8,150,521 | B2 | 4/2012 | Crowley et al. |
| 8,160,672 | B2 | 4/2012 | Kim et al. |
| 8,160,702 | B2 | 4/2012 | Mann et al. |
| 8,160,704 | B2 | 4/2012 | Freeberg |
| 8,165,694 | B2 | 4/2012 | Carbanaru et al. |
| 8,175,715 | B1 | 5/2012 | Cox |
| 8,180,428 | B2 | 5/2012 | Kaiser et al. |
| 8,180,451 | B2 | 5/2012 | Hickman et al. |
| 8,185,213 | B2 | 5/2012 | Kveen et al. |
| 8,187,161 | B2 | 5/2012 | Li et al. |
| 8,195,293 | B2 | 6/2012 | Limousin et al. |
| 8,204,590 | B2 | 6/2012 | Sambelashvili et al. |
| 8,204,595 | B2 | 6/2012 | Pianca et al. |
| 8,204,605 | B2 | 6/2012 | Hastings et al. |
| 8,209,014 | B2 | 6/2012 | Doerr |
| 8,214,041 | B2 | 7/2012 | Van Gelder et al. |
| 8,214,043 | B2 | 7/2012 | Matos |
| 8,224,244 | B2 | 7/2012 | Kim et al. |
| 8,229,556 | B2 | 7/2012 | Li |
| 8,233,985 | B2 | 7/2012 | Bulkes et al. |
| 8,262,578 | B1 | 9/2012 | Bharmi et al. |
| 8,265,748 | B2 | 9/2012 | Liu et al. |
| 8,265,757 | B2 | 9/2012 | Mass et al. |
| 8,280,521 | B2 | 10/2012 | Haubrich et al. |
| 8,285,387 | B2 | 10/2012 | Utsi et al. |
| 8,290,598 | B2 | 10/2012 | Boon et al. |
| 8,290,600 | B2 | 10/2012 | Hastings et al. |
| 8,295,939 | B2 | 10/2012 | Jacobson |
| 8,301,254 | B2 | 10/2012 | Mosesov et al. |
| 8,315,701 | B2 | 11/2012 | Cowan et al. |
| 8,315,708 | B2 | 11/2012 | Berthelsdorf et al. |
| 8,321,014 | B2 | 11/2012 | Maskara et al. |
| 8,321,021 | B2 | 11/2012 | Kisker et al. |
| 8,321,036 | B2 | 11/2012 | Brockway et al. |
| 8,332,036 | B2 | 12/2012 | Hastings et al. |
| 8,335,563 | B2 | 12/2012 | Stessman |
| 8,335,568 | B2 | 12/2012 | Heruth et al. |
| 8,340,750 | B2 | 12/2012 | Prakash et al. |
| 8,340,780 | B2 | 12/2012 | Hastings et al. |

(56) References Cited

U.S. PATENT DOCUMENTS 8,352,025 B2 1/2013 Jacobson
8,352,027 B2 1/2013 Spinelli et al.
8,352,028 B2 1/2013 Wenger
8,352,038 B2 1/2013 Mao et al.
8,359,098 B2 1/2013 Lund et al.
8,364,261 B2 1/2013 Stubbs et al.
8,364,276 B2 1/2013 Willis
8,369,959 B2 2/2013 Meskens
8,369,962 B2 2/2013 Abrahamson
8,380,320 B2 2/2013 Spital
8,383,269 B2 2/2013 Scott et al.
8,386,051 B2 2/2013 Rys
8,391,964 B2 3/2013 Musley et al.
8,391,981 B2 3/2013 Mosesov
8,391,990 B2 3/2013 Smith et al.
8,391,995 B2 * 3/2013 Efimov .................. A61N 1/362 607/122
8,401,616 B2 3/2013 Verard et al.
8,406,874 B2 3/2013 Liu et al.
8,406,879 B2 3/2013 Shuros et al.
8,406,886 B2 3/2013 Gaunt et al.
8,406,899 B2 3/2013 Reddy et al.
8,412,352 B2 4/2013 Griswold et al.
8,417,340 B2 4/2013 Goossen
8,417,341 B2 4/2013 Freeberg
8,423,149 B2 4/2013 Hennig
8,428,716 B2 4/2013 Mullen et al.
8,428,722 B2 4/2013 Verhoef et al.
8,433,402 B2 4/2013 Ruben et al.
8,433,409 B2 4/2013 Johnson et al.
8,433,420 B2 4/2013 Bange et al.
8,447,412 B2 5/2013 Dal Molin et al.
8,452,413 B2 5/2013 Young et al.
8,457,740 B2 6/2013 Osche
8,457,742 B2 6/2013 Jacobson
8,457,744 B2 6/2013 Janzig et al.
8,457,761 B2 6/2013 Wariar
8,467,871 B2 6/2013 Maskara
8,478,407 B2 7/2013 Demmer et al.
8,478,408 B2 7/2013 Hastings et al.
8,478,431 B2 7/2013 Griswold et al.
8,494,632 B2 7/2013 Sun et al.
8,504,156 B2 8/2013 Bonner et al.
8,509,910 B2 8/2013 Sowder et al.
8,509,916 B2 8/2013 Byrd et al.
8,515,559 B2 8/2013 Roberts et al.
8,521,268 B2 8/2013 Zhang et al.
8,525,340 B2 9/2013 Eckhardt et al.
8,527,068 B2 9/2013 Ostroff
8,532,790 B2 9/2013 Griswold
8,538,526 B2 9/2013 Stahmann et al.
8,541,131 B2 9/2013 Lund
8,543,205 B2 9/2013 Ostroff
8,547,248 B2 10/2013 Zdeblick et al.
8,548,605 B2 10/2013 Ollivier
8,554,333 B2 10/2013 Wu et al.
8,565,882 B2 10/2013 Matoes
8,565,897 B2 10/2013 Regnier et al.
8,571,678 B2 10/2013 Wang
8,577,327 B2 11/2013 Makdissi et al.
8,588,926 B2 11/2013 Moore et al.
8,594,775 B2 11/2013 Ghosh et al.
8,612,002 B2 12/2013 Faltys et al.
8,615,310 B2 12/2013 Khairkhahan et al.
8,617,082 B2 12/2013 Zhang et al.
8,626,280 B2 1/2014 Allavatam et al.
8,626,294 B2 1/2014 Sheldon et al.
8,634,908 B2 1/2014 Cowan
8,634,912 B2 1/2014 Bornzin et al.
8,634,919 B1 1/2014 Hou et al.
8,639,333 B2 1/2014 Stadler et al.
8,639,335 B2 1/2014 Peichel et al.
8,644,934 B2 2/2014 Hastings et al.
8,649,859 B2 2/2014 Smith et al.
8,670,842 B1 3/2014 Bornzin et al.
8,676,314 B2 3/2014 Maskara et al.
8,676,319 B2 3/2014 Knoll
8,676,335 B2 3/2014 Katoozi et al.
8,688,234 B2 * 4/2014 Zhu ........................ A61N 1/368 607/119
8,700,173 B2 4/2014 Edlund
8,700,181 B2 4/2014 Bornzin et al.
8,705,599 B2 4/2014 Dal Molin et al.
8,718,766 B2 5/2014 Wahlberg
8,718,773 B2 5/2014 Willis et al.
8,725,260 B2 5/2014 Shuros et al.
8,731,642 B2 5/2014 Zarkh et al.
8,738,133 B2 5/2014 Shuros et al.
8,738,147 B2 5/2014 Hastings et al.
8,744,555 B2 6/2014 Allavatam et al.
8,744,572 B1 6/2014 Greenhut et al.
8,747,314 B2 6/2014 Stahmann et al.
8,750,994 B2 6/2014 Ghosh et al.
8,750,998 B1 6/2014 Ghosh et al.
8,755,884 B2 6/2014 Demmer et al.
8,758,365 B2 6/2014 Bonner et al.
8,761,880 B2 * 6/2014 Maskara .............. A61N 1/3627 607/9
8,768,459 B2 7/2014 Ghosh et al.
8,768,483 B2 7/2014 Schmitt et al.
8,774,572 B2 7/2014 Hamamoto
8,781,605 B2 7/2014 Bornzin et al.
8,788,035 B2 7/2014 Jacobson
8,788,053 B2 7/2014 Jacobson
8,798,740 B2 8/2014 Samade et al.
8,798,745 B2 8/2014 Jacobson
8,798,762 B2 8/2014 Fain et al.
8,798,770 B2 8/2014 Reddy
8,805,505 B1 8/2014 Roberts
8,805,528 B2 8/2014 Corndorf
8,812,109 B2 8/2014 Blomqvist et al.
8,818,504 B2 8/2014 Bodner et al.
8,827,913 B2 9/2014 Havel et al.
8,831,747 B1 9/2014 Min et al.
8,838,237 B1 * 9/2014 Niazi ................... A61N 1/0587 607/9
8,855,789 B2 10/2014 Jacobson
8,861,830 B2 10/2014 Brada et al.
8,868,186 B2 10/2014 Kroll
8,886,307 B2 11/2014 Sambelashvili et al.
8,886,311 B2 11/2014 Anderson et al.
8,886,339 B2 11/2014 Faltys et al.
8,903,473 B2 12/2014 Rogers et al.
8,903,513 B2 12/2014 Ollivier
8,909,336 B2 12/2014 Navarro-Paredes et al.
8,914,131 B2 12/2014 Bornzin et al.
8,923,795 B2 12/2014 Makdissi et al.
8,923,963 B2 12/2014 Bonner et al.
8,938,300 B2 1/2015 Rosero
8,942,806 B2 1/2015 Sheldon et al.
8,948,883 B2 2/2015 Eggen et al.
8,958,892 B2 2/2015 Khairkhahan et al.
8,977,358 B2 3/2015 Ewert et al.
8,989,873 B2 3/2015 Locsin
8,996,109 B2 3/2015 Karst et al.
9,002,467 B2 4/2015 Smith et al.
9,008,776 B2 4/2015 Cowan et al.
9,008,777 B2 4/2015 Dianaty et al.
9,014,818 B2 4/2015 Deterre et al.
9,017,341 B2 4/2015 Bornzin et al.
9,020,611 B2 4/2015 Khairkhahan et al.
9,033,996 B1 5/2015 West
9,037,262 B2 5/2015 Regnier et al.
9,042,984 B2 5/2015 Demmer et al.
9,072,872 B2 7/2015 Asleson et al.
9,072,911 B2 7/2015 Hastings et al.
9,072,913 B2 7/2015 Jacobson
9,101,281 B2 8/2015 Reinert et al.
9,119,959 B2 9/2015 Rys et al.
9,155,882 B2 10/2015 Grubac et al.
9,168,372 B2 10/2015 Fain
9,168,380 B1 10/2015 Greenhut et al.
9,168,383 B2 10/2015 Jacobson et al.
9,180,285 B2 11/2015 Moore et al.

(56) References Cited

U.S. PATENT DOCUMENTS 9,192,774 B2 11/2015 Jacobson
9,205,225 B2 12/2015 Khairkhahan et al.
9,216,285 B1 12/2015 Boling et al.
9,216,293 B2 12/2015 Berthiaume et al.
9,216,298 B2 12/2015 Jacobson
9,227,077 B2 1/2016 Jacobson
9,238,145 B2 1/2016 Wenzel et al.
9,242,102 B2 1/2016 Khairkhahan et al.
9,242,113 B2 1/2016 Smith et al.
9,248,300 B2 2/2016 Rys et al.
9,265,436 B2 2/2016 Min et al.
9,265,962 B2 2/2016 Dianaty et al.
9,272,155 B2 3/2016 Ostroff
9,278,218 B2 3/2016 Karst et al.
9,278,229 B1 3/2016 Reinke et al.
9,283,381 B2 3/2016 Grubac et al.
9,283,382 B2 3/2016 Berthiaume et al.
9,289,612 B1 3/2016 Sambelashbili et al.
9,302,115 B2 4/2016 Molin et al.
9,320,446 B2 4/2016 Gillberg et al.
9,333,364 B2 5/2016 Echt et al.
9,358,387 B2 6/2016 Suwito et al.
9,358,400 B2 6/2016 Jacobson
9,364,675 B2 6/2016 Deterre et al.
9,370,663 B2 6/2016 Moulder
9,375,580 B2 6/2016 Bonner et al.
9,375,581 B2 6/2016 Baru et al.
9,381,365 B2 7/2016 Kibler et al.
9,393,424 B2 7/2016 Demmer et al.
9,393,436 B2 7/2016 Doerr
9,399,139 B2 7/2016 Demmer et al.
9,399,140 B2 7/2016 Cho et al.
9,409,033 B2 8/2016 Jacobson
9,427,594 B1 8/2016 Bornzin et al.
9,433,368 B2 9/2016 Stahmann et al.
9,433,780 B2 9/2016 Regnier et al.
9,457,193 B2 10/2016 Klimovitch et al.
9,474,457 B2 10/2016 Ghosh et al.
9,486,151 B2 11/2016 Ghosh et al.
9,492,668 B2 11/2016 Sheldon et al.
9,492,669 B2 11/2016 Demmer et al.
9,492,674 B2 11/2016 Schmidt et al.
9,492,677 B2 11/2016 Greenhut et al.
9,511,233 B2 12/2016 Sambelashvili
9,511,236 B2 12/2016 Varady et al.
9,511,237 B2 12/2016 Deterre et al.
9,517,336 B2 12/2016 Eggen et al.
9,522,276 B2 12/2016 Shen et al.
9,522,280 B2 12/2016 Fishler et al.
9,526,522 B2 12/2016 Wood et al.
9,526,891 B2 12/2016 Eggen et al.
9,526,909 B2 12/2016 Stahmann et al.
9,533,163 B2 1/2017 Klimovitch et al.
9,561,382 B2 2/2017 Persson et al.
9,566,012 B2 2/2017 Greenhut et al.
9,579,500 B2 2/2017 Rys et al.
9,623,234 B2 4/2017 Anderson
9,636,511 B2 5/2017 Carney et al.
9,643,014 B2 5/2017 Zhang et al.
9,675,579 B2 6/2017 Rock et al.
9,707,399 B2 7/2017 Zielinski et al.
9,724,519 B2 8/2017 Demmer et al.
9,789,319 B2 10/2017 Sambelashvili
9,808,628 B2 11/2017 Sheldon et al.
9,808,633 B2 11/2017 Bonner et al.
9,877,789 B2 1/2018 Ghosh
9,924,884 B2 3/2018 Ghosh et al.
10,004,467 B2 6/2018 Lahm et al.
10,064,567 B2 9/2018 Ghosh et al.
10,099,050 B2 10/2018 Chen et al.
10,166,396 B2 1/2019 Schrock et al.
10,251,555 B2 4/2019 Ghosh et al.
10,549,092 B1 * 2/2020 Hakki .................... A61N 7/00
10,780,281 B2 * 9/2020 Ghosh .................. A61N 1/3684
10,981,001 B2 * 4/2021 Prillinger ................. A61N 1/37
11,207,529 B2 * 12/2021 Zhou .................... A61N 1/3627
11,400,296 B2 * 8/2022 Yang .................... A61N 1/0573
RE50,170 E * 10/2024 Niazi .................. A61N 1/3622
2002/0032470 A1 3/2002 Linberg
2002/0035376 A1 3/2002 Bardy et al.
2002/0035377 A1 3/2002 Bardy et al.
2002/0035378 A1 3/2002 Bardy et al.
2002/0035380 A1 3/2002 Rissmann et al.
2002/0035381 A1 3/2002 Bardy et al.
2002/0042629 A1 4/2002 Bardy et al.
2002/0042630 A1 4/2002 Bardy et al.
2002/0042634 A1 4/2002 Bardy et al.
2002/0049475 A1 4/2002 Bardy et al.
2002/0049476 A1 4/2002 Bardy et al.
2002/0052636 A1 5/2002 Bardy et al.
2002/0068958 A1 6/2002 Bardy et al.
2002/0072773 A1 6/2002 Bardy et al.
2002/0082665 A1 6/2002 Haller et al.
2002/0091414 A1 7/2002 Bardy et al.
2002/0095196 A1 7/2002 Linberg
2002/0099423 A1 7/2002 Berg et al.
2002/0103510 A1 8/2002 Bardy et al.
2002/0107545 A1 8/2002 Rissmann et al.
2002/0107546 A1 8/2002 Ostroff et al.
2002/0107547 A1 8/2002 Erlinger et al.
2002/0107548 A1 8/2002 Bardy et al.
2002/0107549 A1 8/2002 Bardy et al.
2002/0107559 A1 8/2002 Sanders et al.
2002/0120299 A1 8/2002 Ostroff et al.
2002/0169484 A1 11/2002 Mathis
2002/0173830 A1 11/2002 Starkweather et al.
2002/0193846 A1 12/2002 Pool et al.
2003/0004549 A1 1/2003 Hill et al.
2003/0009203 A1 1/2003 Lebel et al.
2003/0028082 A1 2/2003 Thompson
2003/0040779 A1 2/2003 Engmark et al.
2003/0041866 A1 3/2003 Linberg et al.
2003/0045805 A1 3/2003 Sheldon et al.
2003/0083702 A1 5/2003 Stadler
2003/0088278 A1 5/2003 Bardy et al.
2003/0092995 A1 5/2003 Thompson
2003/0097153 A1 5/2003 Bardy et al.
2003/0105497 A1 6/2003 Zhu et al.
2003/0114908 A1 6/2003 Flach
2003/0144701 A1 7/2003 Mehra et al.
2003/0187460 A1 10/2003 Chin et al.
2003/0187461 A1 10/2003 Chin
2003/0199938 A1 10/2003 Smits
2003/0204233 A1 10/2003 Laske .................... A61N 1/057
607/127
2004/0024435 A1 2/2004 Leckrone et al.
2004/0064158 A1 4/2004 Klein ..................... A61N 1/056
607/9
2004/0068302 A1 4/2004 Rodgers et al.
2004/0087938 A1 5/2004 Leckrone et al.
2004/0088035 A1 5/2004 Guenst et al.
2004/0102830 A1 5/2004 Williams
2004/0127959 A1 7/2004 Amundson et al.
2004/0133242 A1 7/2004 Chapman et al.
2004/0147969 A1 7/2004 Mann et al.
2004/0147973 A1 7/2004 Hauser
2004/0167558 A1 8/2004 Igo et al.
2004/0167587 A1 8/2004 Thompson
2004/0172071 A1 9/2004 Bardy et al.
2004/0172077 A1 9/2004 Chinchoy
2004/0172104 A1 9/2004 Berg et al.
2004/0176817 A1 9/2004 Wahlstrand et al.
2004/0176818 A1 9/2004 Wahlstrand et al.
2004/0176830 A1 9/2004 Fang
2004/0186529 A1 9/2004 Bardy et al.
2004/0204673 A1 10/2004 Flaherty
2004/0210292 A1 10/2004 Bardy et al.
2004/0210293 A1 10/2004 Bardy et al.
2004/0210294 A1 10/2004 Bardy et al.
2004/0215308 A1 10/2004 Bardy et al.
2004/0220624 A1 11/2004 Ritscher et al.
2004/0220626 A1 11/2004 Wagner
2004/0220639 A1 11/2004 Mulligan et al.

(56) References Cited

U.S. PATENT DOCUMENTS

2004/0230236 A1 11/2004 Struble ................ A61N 1/3622 607/9
2004/0230283 A1 11/2004 Prinzen ................ A61N 1/362 607/126
2004/0249431 A1 12/2004 Ransbury et al.
2004/0260348 A1 12/2004 Bakken et al.
2004/0267303 A1 12/2004 Guenst
2005/0008210 A1 1/2005 Evron et al.
2005/0038477 A1 2/2005 Kramer et al.
2005/0061320 A1 3/2005 Lee et al.
2005/0070962 A1 3/2005 Echt et al.
2005/0102003 A1 5/2005 Grabek et al.
2005/0137629 A1 6/2005 Dyjach et al.
2005/0137671 A1 6/2005 Liu ...................... A61N 1/0568 607/122
2005/0149138 A1 7/2005 Min et al.
2005/0165466 A1 7/2005 Morris et al.
2005/0182465 A1 8/2005 Ness
2005/0203410 A1 9/2005 Jenkins
2005/0277990 A1 12/2005 Ostroff et al.
2005/0283208 A1 12/2005 Von Arx et al.
2005/0288743 A1 12/2005 Ahn et al.
2006/0042830 A1 3/2006 Maghribi et al.
2006/0052829 A1 3/2006 Sun et al.
2006/0052830 A1 3/2006 Spinelli et al.
2006/0064135 A1 3/2006 Brockway
2006/0064149 A1 3/2006 Belacazar et al.
2006/0074285 A1 4/2006 Zarkh et al.
2006/0085039 A1 4/2006 Hastings et al.
2006/0085041 A1 4/2006 Hastings et al.
2006/0085042 A1 4/2006 Hastings et al.
2006/0095078 A1 5/2006 Tronnes
2006/0106442 A1 5/2006 Richardson et al.
2006/0116746 A1 6/2006 Chin
2006/0135999 A1 6/2006 Bodner et al.
2006/0136004 A1 6/2006 Cowan et al.
2006/0142814 A1* 6/2006 Laske .................... A61N 1/056 607/28
2006/0161061 A1 7/2006 Echt et al.
2006/0161205 A1 7/2006 Mitrani et al.
2006/0161211 A1 7/2006 Thompson ............. A61N 1/368 607/19
2006/0200002 A1 9/2006 Guenst
2006/0206151 A1 9/2006 Lu
2006/0212079 A1 9/2006 Routh et al.
2006/0235478 A1 10/2006 Van Gelder et al.
2006/0241701 A1 10/2006 Markowitz et al.
2006/0241705 A1 10/2006 Neumann et al.
2006/0247672 A1 11/2006 Vidlund et al.
2006/0259088 A1 11/2006 Pastore et al.
2006/0265018 A1 11/2006 Smith et al.
2007/0004979 A1 1/2007 Wojciechowicz et al.
2007/0016098 A1 1/2007 Kim et al.
2007/0027508 A1 2/2007 Cowan
2007/0049975 A1 3/2007 Cates et al.
2007/0078490 A1 4/2007 Cowan et al.
2007/0088394 A1 4/2007 Jacobson
2007/0088396 A1 4/2007 Jacobson
2007/0088397 A1 4/2007 Jacobson
2007/0088398 A1 4/2007 Jacobson
2007/0088405 A1 4/2007 Jaconson
2007/0135882 A1 6/2007 Drasler et al.
2007/0135883 A1 6/2007 Drasler et al.
2007/0150037 A1 6/2007 Hastings et al.
2007/0150038 A1 6/2007 Hastings et al.
2007/0156190 A1 7/2007 Cinbis
2007/0167758 A1 7/2007 Costello ................. A61B 6/037 600/437
2007/0219525 A1 9/2007 Gelfand et al.
2007/0219590 A1 9/2007 Hastings et al.
2007/0225545 A1 9/2007 Ferrari
2007/0233206 A1 10/2007 Frikart et al.
2007/0233216 A1 10/2007 Liu ...................... A61N 1/0568 607/122
2007/0239244 A1 10/2007 Morgan et al.
2007/0239248 A1 10/2007 Hastings .............. A61N 1/0573 607/127
2007/0255376 A1 11/2007 Michels et al.
2007/0276444 A1 11/2007 Gelbart et al.
2007/0293900 A1 12/2007 Sheldon et al.
2007/0293904 A1 12/2007 Gelbart et al.
2007/0299475 A1 12/2007 Levin et al.
2008/0004663 A1 1/2008 Jorgenson
2008/0021505 A1 1/2008 Hastings et al.
2008/0021519 A1 1/2008 De Geest et al.
2008/0021532 A1 1/2008 Kveen et al.
2008/0058656 A1 3/2008 Costello ............... A61B 5/1107 600/508
2008/0065183 A1 3/2008 Whitehurst et al.
2008/0065185 A1 3/2008 Worley
2008/0071318 A1 3/2008 Brooke et al.
2008/0109054 A1 5/2008 Hastings et al.
2008/0119911 A1 5/2008 Rosero
2008/0130670 A1 6/2008 Kim et al.
2008/0154139 A1 6/2008 Shuros et al.
2008/0154322 A1 6/2008 Jackson et al.
2008/0183072 A1 7/2008 Robertson ............ A61B 5/1107 600/425
2008/0228234 A1 9/2008 Stancer
2008/0234771 A1 9/2008 Chinchoy et al.
2008/0242976 A1 10/2008 Robertson .......... A61N 1/36514 600/425
2008/0243217 A1 10/2008 Wildon
2008/0269814 A1 10/2008 Rosero
2008/0269816 A1 10/2008 Prakash et al.
2008/0269823 A1 10/2008 Burnes et al.
2008/0269825 A1 10/2008 Chinchoy et al.
2008/0275518 A1 11/2008 Ghanem et al.
2008/0275519 A1 11/2008 Ghanem et al.
2008/0288039 A1 11/2008 Reddy
2008/0294208 A1 11/2008 Willis et al.
2008/0294210 A1 11/2008 Rosero
2008/0294229 A1 11/2008 Friedman et al.
2008/0306359 A1 12/2008 Zdeblick et al.
2009/0018599 A1 1/2009 Hastings et al.
2009/0024180 A1 1/2009 Kisker et al.
2009/0036769 A1 2/2009 Zdeblick .............. A61B 5/1107 600/424
2009/0036941 A1 2/2009 Corbucci
2009/0048646 A1 2/2009 Katoozi et al.
2009/0062895 A1 3/2009 Stahmann et al.
2009/0082827 A1 3/2009 Kveen et al.
2009/0082828 A1 3/2009 Ostroff
2009/0088813 A1 4/2009 Brockway et al.
2009/0099619 A1 4/2009 Lessmeier et al.
2009/0131907 A1 5/2009 Chin et al.
2009/0135886 A1 5/2009 Robertson et al.
2009/0143835 A1 6/2009 Pastore et al.
2009/0171408 A1 7/2009 Solem
2009/0171414 A1 7/2009 Kelly et al.
2009/0204163 A1 8/2009 Shuros et al.
2009/0204170 A1 8/2009 Hastings et al.
2009/0210024 A1 8/2009 Jason
2009/0216292 A1 8/2009 Pless et al.
2009/0234407 A1 9/2009 Hastings et al.
2009/0234411 A1 9/2009 Sambelashvili et al.
2009/0234412 A1 9/2009 Sambelashvili
2009/0234413 A1 9/2009 Sambelashvili et al.
2009/0234414 A1 9/2009 Sambelashvili et al.
2009/0234415 A1 9/2009 Sambelashvili et al.
2009/0248103 A1 10/2009 Sambelashvili et al.
2009/0259272 A1* 10/2009 Reddy .................. A61N 1/0573 607/9
2009/0266573 A1 10/2009 Engmark et al.
2009/0275998 A1 11/2009 Burnes et al.
2009/0275999 A1 11/2009 Burnes et al.
2009/0299447 A1 12/2009 Jensen et al.
2009/0306732 A1 12/2009 Rosenberg ........... A61B 5/0452 607/9
2009/0326397 A1 12/2009 Behzadi ................. A61B 5/415 600/508
2010/0013668 A1 1/2010 Kantervik

(56) References Cited

U.S. PATENT DOCUMENTS

2010/0016911 A1 1/2010 Willis et al.
2010/0016914 A1 1/2010 Mullen et al.
2010/0016917 A1* 1/2010 Efimov .................. A61N 1/362 607/17
2010/0016918 A1 1/2010 Mann ................. A61N 1/37229 607/23
2010/0023078 A1 1/2010 Dong et al.
2010/0023085 A1 1/2010 Wu et al.
2010/0030061 A1 2/2010 Canfield et al.
2010/0030327 A1 2/2010 Chatel
2010/0042108 A1 2/2010 Hibino
2010/0063375 A1 3/2010 Kassab et al.
2010/0063562 A1 3/2010 Cowan et al.
2010/0065871 A1 3/2010 Govari et al.
2010/0069983 A1 3/2010 Peacock, III .......... A61N 1/057 607/9
2010/0094367 A1 4/2010 Sen
2010/0114209 A1 5/2010 Krause et al.
2010/0114214 A1 5/2010 Morelli et al.
2010/0114284 A1 5/2010 Doerr ..................... A61N 1/057 607/120
2010/0125281 A1 5/2010 Jacobson et al.
2010/0152798 A1 6/2010 Sanghera et al.
2010/0152801 A1 6/2010 Koh .................... A61N 1/3686 607/9
2010/0168761 A1 7/2010 Kassab et al.
2010/0168819 A1 7/2010 Freeberg
2010/0185250 A1 7/2010 Rom
2010/0198288 A1 8/2010 Ostroff
2010/0198291 A1 8/2010 Sambelashvili et al.
2010/0198304 A1 8/2010 Wang
2010/0204766 A1 8/2010 Zdeblick ................ A61N 1/372 607/119
2010/0217367 A1 8/2010 Belson
2010/0228308 A1 9/2010 Cowan et al.
2010/0234906 A1 9/2010 Koh
2010/0234924 A1 9/2010 Willis
2010/0241185 A1 9/2010 Mahapatra et al.
2010/0249729 A1 9/2010 Morris et al.
2010/0286541 A1 11/2010 Musley et al.
2010/0286626 A1 11/2010 Petersen
2010/0286744 A1 11/2010 Echt et al.
2010/0298841 A1 11/2010 Prinzen .............. A61N 1/37254 606/129
2010/0305451 A1 12/2010 Kim ......................... A61B 8/12 600/463
2010/0312309 A1 12/2010 Harding
2010/0318147 A1 12/2010 Forslund .............. A61N 1/0573 607/17
2011/0022113 A1 1/2011 Ideblick et al.
2011/0071586 A1 3/2011 Jacobson
2011/0077708 A1 3/2011 Ostroff
2011/0106202 A1 5/2011 Ding et al.
2011/0112398 A1 5/2011 Zarkh et al.
2011/0112600 A1 5/2011 Cowan et al.
2011/0118588 A1 5/2011 Komblau et al.
2011/0118810 A1 5/2011 Cowan et al.
2011/0137187 A1 6/2011 Yang et al.
2011/0144720 A1 6/2011 Cowan et al.
2011/0152970 A1 6/2011 Jollota et al.
2011/0160558 A1 6/2011 Rassatt et al.
2011/0160565 A1 6/2011 Stubbs
2011/0160801 A1 6/2011 Markowitz et al.
2011/0160806 A1 6/2011 Lyden et al.
2011/0166620 A1 7/2011 Cowan et al.
2011/0166621 A1 7/2011 Cowan et al.
2011/0184491 A1 7/2011 Kivi
2011/0190835 A1 8/2011 Brockway et al.
2011/0190841 A1 8/2011 Sambelashvili et al.
2011/0196444 A1 8/2011 Prakash et al.
2011/0208260 A1 8/2011 Jacobson
2011/0218587 A1 9/2011 Jacobson
2011/0230734 A1 9/2011 Fain et al.
2011/0237967 A1 9/2011 Moore et al.
2011/0238102 A1 9/2011 Gutfinger ............. A61B 5/0215 606/184
2011/0245890 A1 10/2011 Brisben et al.
2011/0251660 A1 10/2011 Griswold
2011/0251662 A1 10/2011 Griswold et al.
2011/0270099 A1 11/2011 Ruben et al.
2011/0270339 A1 11/2011 Murray, III et al.
2011/0270340 A1 11/2011 Pellegrini et al.
2011/0276102 A1 11/2011 Cohen
2011/0282423 A1 11/2011 Jacobson
2012/0004527 A1 1/2012 Thompson et al.
2012/0029323 A1 2/2012 Zhao
2012/0035685 A1 2/2012 Saha et al.
2012/0041500 A1 2/2012 Zhu ...................... A61N 1/3627 607/4
2012/0041508 A1 2/2012 Rousso et al.
2012/0059433 A1 3/2012 Cowan et al.
2012/0059436 A1 3/2012 Fontaine et al.
2012/0065500 A1 3/2012 Rogers et al.
2012/0078322 A1 3/2012 Dal Molin et al.
2012/0089198 A1 4/2012 Ostroff
2012/0089214 A1 4/2012 Kroll et al.
2012/0093245 A1 4/2012 Makdissi et al.
2012/0095521 A1 4/2012 Hintz
2012/0095539 A1 4/2012 Khairkhahan et al.
2012/0101540 A1 4/2012 O'Brien et al.
2012/0101553 A1 4/2012 Reddy
2012/0109148 A1 5/2012 Bonner et al.
2012/0109149 A1 5/2012 Bonner et al.
2012/0109235 A1 5/2012 Sheldon et al.
2012/0109236 A1 5/2012 Jacobson et al.
2012/0109259 A1 5/2012 Bond et al.
2012/0116489 A1 5/2012 Khairkhahan et al.
2012/0150251 A1 6/2012 Giftakis et al.
2012/0158111 A1 6/2012 Khairkhahan et al.
2012/0165827 A1 6/2012 Khairkhahan et al.
2012/0172690 A1 7/2012 Anderson et al.
2012/0172891 A1 7/2012 Lee
2012/0172892 A1 7/2012 Grubac et al.
2012/0172942 A1 7/2012 Berg
2012/0179221 A1 7/2012 Reddy .................. A61N 1/0573 607/37
2012/0197350 A1 8/2012 Roberts et al.
2012/0197373 A1 8/2012 Khairkhahan et al.
2012/0215285 A1 8/2012 Tahmasian et al.
2012/0232478 A1 9/2012 Haslinger
2012/0232563 A1 9/2012 Williams .......... A61M 25/0147 606/129
2012/0232565 A1 9/2012 Kveen et al.
2012/0245665 A1* 9/2012 Friedman ............. A61N 1/0573 607/122
2012/0263218 A1 10/2012 Dal Molin et al.
2012/0271369 A1 10/2012 Ollivier .................. A61N 1/059 607/4
2012/0277600 A1 11/2012 Greenhut
2012/0277606 A1 11/2012 Ellingson et al.
2012/0283587 A1 11/2012 Gosh et al.
2012/0283795 A1 11/2012 Stancer et al.
2012/0283807 A1 11/2012 Deterre et al.
2012/0284003 A1 11/2012 Gosh et al.
2012/0290025 A1 11/2012 Keimel
2012/0296228 A1 11/2012 Zhang et al.
2012/0296381 A1 11/2012 Matos
2012/0303082 A1 11/2012 Dong et al.
2012/0316613 A1 12/2012 Keefe et al.
2013/0012151 A1 1/2013 Hankins
2013/0013017 A1 1/2013 Mullen et al.
2013/0023975 A1 1/2013 Locsin
2013/0035748 A1 2/2013 Bonner et al.
2013/0041422 A1 2/2013 Jacobson
2013/0053906 A1 2/2013 Ghosh et al.
2013/0053908 A1 2/2013 Smith et al.
2013/0053915 A1 2/2013 Holmstrom et al.
2013/0053921 A1 2/2013 Bonner et al.
2013/0060298 A1 3/2013 Splett et al.
2013/0066169 A1 3/2013 Rys et al.
2013/0072770 A1 3/2013 Rao et al.
2013/0079798 A1 3/2013 Tran et al.
2013/0079861 A1 3/2013 Reinert et al.

(56) References Cited

U.S. PATENT DOCUMENTS

2013/0085350 A1 4/2013 Schugt et al.
2013/0085403 A1 4/2013 Gunderson et al.
2013/0085550 A1 4/2013 Polefko et al.
2013/0096649 A1 4/2013 Martin et al.
2013/0103047 A1 4/2013 Steingisser et al.
2013/0103109 A1 4/2013 Jacobson
2013/0110008 A1 5/2013 Bourg et al.
2013/0110127 A1 5/2013 Bornzin et al.
2013/0110192 A1 5/2013 Tran et al.
2013/0110219 A1 5/2013 Bornzin et al.
2013/0116529 A1 5/2013 Min et al.
2013/0116738 A1* 5/2013 Samade ............... A61N 1/3684 607/9
2013/0116739 A1 5/2013 Brada et al.
2013/0116740 A1* 5/2013 Bornzin ............... A61N 1/3684 607/9
2013/0116741 A1* 5/2013 Bornzin ............... A61N 1/3684 607/9
2013/0123872 A1* 5/2013 Bornzin ............... A61N 1/3684 607/17
2013/0123875 A1 5/2013 Varady et al.
2013/0131591 A1 5/2013 Berthiaume et al.
2013/0131693 A1 5/2013 Berthiaume et al.
2013/0131750 A1 5/2013 Stadler et al.
2013/0131751 A1 5/2013 Stadler et al.
2013/0138006 A1 5/2013 Bornzin et al.
2013/0150695 A1 6/2013 Biela et al.
2013/0150911 A1 6/2013 Perschbacher et al.
2013/0150912 A1 6/2013 Perschbacher et al.
2013/0184776 A1 7/2013 Shuros et al.
2013/0196703 A1 8/2013 Masoud et al.
2013/0197599 A1 8/2013 Sambelashvili et al.
2013/0197609 A1 8/2013 Moore et al.
2013/0231710 A1 9/2013 Jacobson
2013/0231728 A1 9/2013 Ollivier .................. A61N 1/059 607/127
2013/0238072 A1 9/2013 Deterre et al.
2013/0238073 A1 9/2013 Makdissi et al.
2013/0253342 A1 9/2013 Griswold et al.
2013/0253343 A1 9/2013 Walfhauser et al.
2013/0253344 A1 9/2013 Griswold et al.
2013/0253345 A1 9/2013 Griswold et al.
2013/0253346 A1 9/2013 Griswold et al.
2013/0253347 A1 9/2013 Griswold et al.
2013/0261497 A1 10/2013 Pertijs et al.
2013/0265144 A1 10/2013 Banna et al.
2013/0268017 A1 10/2013 Zhang et al.
2013/0268042 A1 10/2013 Hastings et al.
2013/0274828 A1 10/2013 Willis
2013/0274847 A1 10/2013 Ostroff
2013/0282070 A1 10/2013 Cowan et al.
2013/0282073 A1* 10/2013 Cowan ................ A61N 1/3621 607/14
2013/0296727 A1 11/2013 Sullivan et al.
2013/0303872 A1 11/2013 Taff et al.
2013/0324825 A1 12/2013 Ostroff et al.
2013/0325081 A1 12/2013 Karst et al.
2013/0345770 A1 12/2013 Dianaty et al.
2014/0012344 A1 1/2014 Hastings et al.
2014/0018876 A1 1/2014 Ostroff
2014/0018877 A1 1/2014 Demmer et al.
2014/0031836 A1 1/2014 Ollivier
2014/0039591 A1 2/2014 Drasler et al.
2014/0043146 A1 2/2014 Makdissi et al.
2014/0046395 A1 2/2014 Regnier et al.
2014/0046420 A1 2/2014 Moore et al.
2014/0058240 A1 2/2014 Mothilal et al.
2014/0058494 A1 2/2014 Ostroff et al.
2014/0067036 A1 3/2014 Shuros ................ A61N 1/0573 607/126
2014/0074114 A1 3/2014 Khairkhahan et al.
2014/0074186 A1 3/2014 Faltys et al.
2014/0094891 A1 4/2014 Pare et al.
2014/0100627 A1 4/2014 Min
2014/0107723 A1* 4/2014 Hou .................... A61N 1/3756 607/9
2014/0107724 A1* 4/2014 Shuros ................ A61N 1/3712 607/28
2014/0114173 A1 4/2014 Bar-Tal et al.
2014/0114372 A1 4/2014 Ghosh et al.
2014/0121719 A1 5/2014 Bonner et al.
2014/0121720 A1 5/2014 Bonner et al.
2014/0121722 A1 5/2014 Sheldon et al.
2014/0128935 A1 5/2014 Kumar et al.
2014/0135865 A1 5/2014 Hastings et al.
2014/0142648 A1 5/2014 Smith et al.
2014/0148675 A1 5/2014 Nordstrom et al.
2014/0148815 A1 5/2014 Wenzel et al.
2014/0155950 A1 6/2014 Hastings et al.
2014/0169162 A1 6/2014 Romano et al.
2014/0172033 A1 6/2014 Pei .................... A61N 1/36507 607/14
2014/0172060 A1 6/2014 Bornzin ................ A61N 1/059 607/126
2014/0180306 A1 6/2014 Grubac et al.
2014/0180366 A1 6/2014 Edlund
2014/0207149 A1 7/2014 Hastings et al.
2014/0207210 A1 7/2014 Willis et al.
2014/0214104 A1 7/2014 Greenhut et al.
2014/0222098 A1 8/2014 Baru et al.
2014/0222109 A1 8/2014 Moulder
2014/0228913 A1 8/2014 Molin et al.
2014/0236172 A1 8/2014 Hastings et al.
2014/0243848 A1 8/2014 Auricchio et al.
2014/0255298 A1 9/2014 Cole et al.
2014/0257324 A1 9/2014 Fain
2014/0257422 A1 9/2014 Herken
2014/0257444 A1 9/2014 Cole et al.
2014/0276929 A1 9/2014 Foster et al.
2014/0303704 A1 10/2014 Suwito et al.
2014/0309706 A1 10/2014 Jacobson
2014/0323882 A1 10/2014 Ghosh et al.
2014/0323892 A1 10/2014 Ghosh et al.
2014/0330208 A1 11/2014 Christie et al.
2014/0330287 A1 11/2014 Thompson-Nauman et al.
2014/0330326 A1 11/2014 Thompson-Nauman et al.
2014/0339570 A1 11/2014 Mollard et al.
2014/0358135 A1 12/2014 Sambelashvili et al.
2014/0371832 A1 12/2014 Ghosh
2014/0371833 A1 12/2014 Ghosh et al.
2014/0379041 A1 12/2014 Foster
2015/0025612 A1 1/2015 Haasl et al.
2015/0039041 A1 2/2015 Smith et al.
2015/0051609 A1 2/2015 Schmidt et al.
2015/0051610 A1 2/2015 Schmidt et al.
2015/0051611 A1 2/2015 Schmidt et al.
2015/0051612 A1 2/2015 Schmidt et al.
2015/0051613 A1 2/2015 Schmidt et al.
2015/0051614 A1 2/2015 Schmidt et al.
2015/0051615 A1 2/2015 Schmidt et al.
2015/0051616 A1 2/2015 Haasl et al.
2015/0051682 A1 2/2015 Schmidt et al.
2015/0057520 A1 2/2015 Foster et al.
2015/0057558 A1 2/2015 Stahmann et al.
2015/0057721 A1 2/2015 Stahmann et al.
2015/0088155 A1 3/2015 Foster et al.
2015/0105836 A1 4/2015 Bonner et al.
2015/0142070 A1 5/2015 Sambelashvili
2015/0148697 A1 5/2015 Burnes et al.
2015/0149096 A1 5/2015 Soykan
2015/0157861 A1 6/2015 Aghassian
2015/0173655 A1 6/2015 Demmer et al.
2015/0190638 A1 7/2015 Smith et al.
2015/0196756 A1 7/2015 Stahmann et al.
2015/0196757 A1 7/2015 Stahmann et al.
2015/0196758 A1 7/2015 Stahmann et al.
2015/0196769 A1 7/2015 Stahmann et al.
2015/0217119 A1 8/2015 Nikolski et al.
2015/0221898 A1 8/2015 Chi et al.
2015/0224315 A1 8/2015 Stahmann
2015/0224320 A1 8/2015 Stahmann
2015/0258345 A1 9/2015 Smith et al.
2015/0290468 A1 10/2015 Zhang

(56) References Cited

U.S. PATENT DOCUMENTS

2015/0297905 A1 10/2015 Greenhut et al.
2015/0297907 A1 10/2015 Zhang
2015/0305637 A1 10/2015 Greenhut et al.
2015/0305638 A1 10/2015 Zhang
2015/0305639 A1 10/2015 Greenhut et al.
2015/0305640 A1 10/2015 Reinke et al.
2015/0305641 A1 10/2015 Stadler et al.
2015/0305642 A1 10/2015 Reinke et al.
2015/0305695 A1 10/2015 Lahm et al.
2015/0306374 A1 10/2015 Seifert et al.
2015/0306375 A1 10/2015 Marshall et al.
2015/0306406 A1 10/2015 Crutchfield et al.
2015/0306407 A1 10/2015 Crutchfield et al.
2015/0306408 A1 10/2015 Greenhut et al.
2015/0321016 A1 11/2015 O'Brien et al.
2015/0328459 A1 11/2015 Chin et al.
2015/0335894 A1 11/2015 Bornzin et al.
2016/0015287 A1 1/2016 Anderson et al.
2016/0015322 A1 1/2016 Anderson et al.
2016/0023000 A1 1/2016 Cho et al.
2016/0030757 A1 2/2016 Jacobson
2016/0033177 A1 2/2016 Barot et al.
2016/0045738 A1 2/2016 Ghosh et al.
2016/0051821 A1 2/2016 Sambelashvili et al.
2016/0059002 A1 3/2016 Grubac et al.
2016/0067486 A1 3/2016 Brown et al.
2016/0067487 A1 3/2016 Demmer et al.
2016/0067490 A1 3/2016 Carney et al.
2016/0114161 A1 4/2016 Amblard et al.
2016/0121127 A1 5/2016 Klimovitch et al.
2016/0121128 A1 5/2016 Fishler et al.
2016/0121129 A1 5/2016 Persson et al.
2016/0129239 A1 5/2016 Anderson
2016/0213919 A1 7/2016 Suwito et al.
2016/0213937 A1 7/2016 Reinke et al.
2016/0213939 A1 7/2016 Carney et al.
2016/0228026 A1 8/2016 Jackson
2016/0242887 A1 8/2016 Watschke
2016/0317825 A1 11/2016 Jacobson
2016/0367823 A1 12/2016 Cowan et al.
2017/0014629 A1 1/2017 Ghosh et al.
2017/0035315 A1 2/2017 Jackson
2017/0043173 A1 2/2017 Sharma et al.
2017/0043174 A1 2/2017 Greenhut et al.
2017/0056670 A1 3/2017 Sheldon et al.
2017/0182327 A1* 6/2017 Liu ...................... A61B 5/6869
2017/0189681 A1 7/2017 Anderson
2017/0209689 A1 7/2017 Chen
2017/0216575 A1* 8/2017 Asleson ................. A61N 1/056
2017/0304624 A1 10/2017 Friedman et al.
2017/0326369 A1 11/2017 Koop et al.
2017/0340885 A1 11/2017 Sambelashvili
2018/0008829 A1 1/2018 An et al.
2018/0021567 A1 1/2018 An et al.
2018/0021581 A1 1/2018 An et al.
2018/0021582 A1 1/2018 An et al.
2018/0050208 A1* 2/2018 Shuros ............... A61N 1/36843
2018/0078773 A1 3/2018 Thakur et al.
2018/0078779 A1 3/2018 An et al.
2018/0117324 A1 5/2018 Schilling et al.
2018/0140848 A1 5/2018 Stahmann
2018/0178007 A1 6/2018 Shuros et al.
2018/0212451 A1 7/2018 Schmidt et al.
2018/0256902 A1 9/2018 Toy
2018/0264262 A1 9/2018 Haasl et al.
2018/0264272 A1 9/2018 Haasl et al.
2018/0264273 A1 9/2018 Haasl et al.
2018/0264274 A1 9/2018 Haasl et al.
2018/0280686 A1 10/2018 Shuros et al.
2018/0318594 A1* 11/2018 Dosdall ................ A61N 1/3987
2018/0326215 A1* 11/2018 Ghosh .................. A61N 1/3682
2019/0030346 A1 1/2019 Li
2019/0038906 A1 2/2019 Koop et al.
2019/0083779 A1 3/2019 Yang et al.
2019/0083800 A1 3/2019 Yang et al.
2019/0083801 A1 3/2019 Yang et al.
2019/0111270 A1* 4/2019 Zhou .................... A61N 1/3627
2019/0134405 A1* 5/2019 Sheldon ................. A61N 1/371
2019/0134412 A1* 5/2019 Shuros ............... A61N 1/37205
2019/0290905 A1* 9/2019 Yang .................. A61N 1/36592
2019/0290909 A1* 9/2019 Ghosh .................. A61N 1/3684
2019/0290910 A1* 9/2019 Yang .................. A61N 1/37518
2019/0290915 A1* 9/2019 Yang ...................... A61N 1/059
2020/0016395 A1* 1/2020 Makharinsky ......... A61N 1/056
2020/0155798 A1* 5/2020 Yang ...................... A61N 1/057
2020/0206511 A1 7/2020 Goedeke .................. A61B 5/02
2020/0316386 A1* 10/2020 Demmer ............ A61N 1/36592
2020/0338336 A1 10/2020 Makharinsky ....... A61N 1/0573
2020/0338356 A1* 10/2020 Anderson ............ A61N 1/3756

FOREIGN PATENT DOCUMENTS

AU 2014203793 A1 7/2014
CN 202933393 5/2013
EP 0362611 A1 4/1990
EP 0459 239 A2 12/1991
EP 0 728 497 A2 8/1996
EP 1 541 191 A1 6/2005
EP 1 702 648 A1 9/2006
EP 1 904 166 B1 6/2011
EP 2 452 721 A1 5/2012
EP 2 471 452 A1 7/2012
EP 2 662 113 A2 11/2013
EP 1 703 944 B1 7/2015
JP 2005245215 9/2005
WO WO 95/00202 1/1995
WO WO 96/36134 11/1996
WO WO 97/24981 7/1997
WO WO 02/22206 A1 3/2002
WO WO 03/092800 A1 11/2003
WO WO 2005/000206 A2 1/2005
WO WO 2005/042089 A1 5/2005
WO WO 2006/086435 A2 8/2006
WO WO 2006/113659 A1 10/2006
WO WO 2007/073435 A1 6/2007
WO WO 2007/075974 A2 7/2007
WO WO 2009/006531 A1 1/2009
WO WO 2013/080038 A2 6/2013
WO WO 2013/098644 A2 7/2013
WO WO 2015/081221 A1 6/2015
WO WO 2016/011042 A1 1/2016
WO WO 2016/077099 A1 5/2016
WO WO 2016/110856 A1 7/2016
WO WO 2016/171891 A1 10/2016
WO WO 2017/075193 A1 5/2017
WO WO 2018/009569 A1 1/2018
WO WO 2018/017226 A1 1/2018
WO WO 2018/017361 A1 1/2018
WO WO 2018/035343 A1 2/2018
WO WO 2018/081519 A1 5/2018

OTHER PUBLICATIONS

Cantu et al., Validation of Criteria for Selective His Bundle and Para-Hisian Permanent Pacing, PACE, vol. 29, Dec. 2006 (Year: 2006).*
Nagarajan et al., Anatomical Considerations for His Bundle Pacing, Circulation: Arrhythmia and Electrophysiology, 2019 (Year: 2019).*
Saremi et al., Fibrous Skeleton of the Heart: Anatomic Overview and Evaluation of Pathologic Conditions with CT and MR Imaging, Cardiac Imaging, Aug. 18, 2017, (abstract and Figures only) (Year: 2017).*
Schoonderwoerd et al., "Atrial ultrastructural changes during experimental atrial tachycardia depend on high ventricular rate," *J Cardiovasc Electrophysiol.*, Oct. 2004; 15(10):1167-74.
Sedmera, "Function and form in the developing cardiovascular system," *Cardiovasc Res.*, Jul. 2011; 91(2):252-9.
Severi et al., "Alterations of atrial electrophysiology induced by electrolyte variations: combined computational and P-wave analysis," *Europace*, Jun. 2010; 12(6):842-9.
Seyedi et al., "A Survey on Intrabody Communications for Body

(56) References Cited

OTHER PUBLICATIONS

Area Network Application," IEEE Transactions on Biomedical Engineering, vol. 60(8): 2067-2079, 2013.
Shah et al., "Stable atrial sensing on long-term follow up of VDD pacemakers," *Indian Pacing and Electrophysiology Journal*, Oct. 2006; 6(4):189-93.
Shenthar et al., "Permanent pacemaker implantation in a patient with situs solitus, dextrocardia, and corrected transposition of the great arteries using a novel angiographic technique," *Journal of Arrhythmia*, Apr. 2014; 30(2):134-138.
Shenthar et al., "Transvenous permanent pacemaker implantation in dextrocardia: technique, challenges, outcome, and a brief review of literature," *Europace*, Sep. 2014; 16(9):1327-33.
Shirayama, "Role of atrial fibrillation threshold evaluation on guiding treatment," *Indian Pacing and Electrophysiology Journal*, Oct. 2003; 3(4):224-230.
Sperzel et al., "Intraoperative Characterization of Interventricular Mechanical Dyssynchrony Using Electroanatomic Mapping System—A Feasibility Study," Journal of Interventional Cardiac Electrophysiology, Nov. 2012, 35(2): 189-96.
Spickler et al., "Totally Self-Contained Intracardiac Pacemaker," Journal of Electrocardiology, vol. 3(3&4): 324-331, 1970.
Sreeram et al., "Indications for Electrophysiology Study in children," *Indian Pacing and Electrophysiology Journal*, Apr.-Jun. 2008; 8(Suppl. 1):S36-S54.
Stockburger et al., "Optimization of cardiac resynchronization guided by Doppler echocardiography: haemodynamic improvement and intraindividual variability with different pacing configurations and atrioventricular delays," *Europace*, Oct. 2006; 8(10):881-6.
Stroobandt et al., "Prediction of Wenckebach Behavior and Block Response in DDD Pacemakers," *Pacing Clin Electrophysiol.*, Jun. 2006; 9(6):1040-6.
Suenari et al., "Idiopathic left ventricular tachycardia with dual electrocardiogram morphologies in a single patient," *Europace*, Apr. 2010; 12(4):592-4.
Sweeney et al., "Analysis of Ventricular Activation Using Surface Electrocardiogramadict Left Ventricular Reverse Volumetric Remodeling During Cardiac Resynchronization Therapy," Circulation, Feb. 9, 2010, 121(5): 626-34.
Tan et al., "Electrocardiographic evidence of ventricular repolarization remodelling during atrial fibrillation," *Europace*, Jan. 2008; 10(1):99-104.
Taramasco et al., "Internal low-energy cardioversion: a therapeutic option for restoring sinus rhythm in chronic atrial fibrillation after failure of external cardioversion," *Europace*, Jul. 1999; 1(3):179-82.
Testa et al., "Rate-control or rhythm-control: where do we stand?" *Indian Pacing and Electrophysiology Journal*, Oct. 2005; 5(4):296-304.
Thejus et al., "N-terminal Pro-Brain Natriuretic Peptide and Atrial Fibrillation," *Indian Pacing and Electrophysiology Journal*, Jan. 2009; 9(1):1-4.
Thornton et al., "Magnetic Assisted Navigation in Electrophysiology and Cardiac Resynchronisation: a Review," *Indian Pacing and Electrophysiology Journal*, Oct. 2006; 6(4):202-13.
Tilz et al., "In vivo left-ventricular contact force analysis: comparison of antegrade transseptal with retrograde transaortic mapping strategies and correlation of impedance and electrical amplitude with contact force," *Europace*, Sep. 2014; 16(9):1387-95.
Tomaske et al., "Do daily threshold trend fluctuations of epicardial leads correlate with pacing and sensing characteristics in paediatric patients?" *Europace*, Aug. 2007; 9(8):662-668.
Tomioka et al., "The effect of ventricular sequential contraction on helical heart during pacing: high septal pacing versus biventricular pacing," *European Journal of Cardio-thoracic Surgery*, Apr. 1, 2006; 29S1:S198-206.
Tournoux et al., "A 'Regularly Irregular' tachycardia: What is the diagnosis?" *Europace*, Dec. 2008; 10(12):1445-6.
Traykov et al., "Electrogram analysis at the His bundle region and the proximal coronary sinus as a tool to predict left atrial origin of focal atrial tachycardias," *Europace*, Jul. 2011; 13(7):1022-7.
Trudel et al., "Simulation of QRST integral maps with a membrane-based computer heart model employing parallel processing," *IEEE Trans Biomed Eng.*, Aug. 2004; 51(8):1319-29.
Tse et al., "Cardiac dynamics: Alternans and arrhythmogenesis," *Journal of Arrhythmia*, Oct. 2016; 32(5):411-417.
Tse, "Mechanisms of cardiac arrhythmias," *Journal of Arrhythmia*, Apr. 2016; 32(2):75-81.
Ueda et al., "Outcomes of single- or dual-chamber implantable cardioverter defibrillator systems in Japanese patients," *Journal of Arrhythmia*, Apr. 2016; 32(2):89-94.
Van Dam et al., "Volume conductor effects involved in the genesis of the P wave," *Europace*, Sep. 2005; 7 Suppl 2:30-8.
Van den Berg et al., "Depletion of atrial natriuretic peptide during longstanding atrial fibrillation," *Europace*, Sep. 2004; 6(5):433-7.
Van Deursen, et al., "Vectorcardiography as a Tool for Easy Optimization of Cardiac Resynchronization Therapy in Canine LBBB Hearts," Circulation Arrhythmia and Electrophysiology, Jun. 1, 2012, 5(3): 544-52.
Van Opstal et al., "Paradoxical increase of stimulus to atrium interval despite His-bundle capture during para-Hisian pacing," *Europace*, Dec. 2009; 11(12):1702-4.
Veenhuyzen et al., "Diagnostic pacing maneuvers for supraventricular tachycardia: part 1," *Pacing Clin Electrophysiol.*, Jun. 2011; 34(6):767-82.
Veenhuyzen et al., "Diagnostic pacing maneuvers for supraventricular tachycardias: part 2," *Pacing Clin Electrophysiol.*, Jun. 2012; 35(6):757-69.
Veenhuyzen et al., "Principles of Entrainment: Diagnostic Utility for Supraventricular Tachycardia," *Indian Pacing and Electrophysiology Journal*, 2008; 8(1):51-65.
Verbrugge et al., "Revisiting diastolic filling time as mechanistic insight for response to cardiac resynchronization therapy," *Europace*, Dec. 2013; 15(12):1747-56.
Verrier et al., "Mechanisms of ranolazine's dual protection against atrial and ventricular fibrillation," *Europace*, Mar. 2013; 15(3):317-324.
Verrijcken et al., "Pacemaker-mediated tachycardia with varying cycle length: what is the mechanism?" *Europace*, Oct. 2009; 11(10):1400-2.
Villani et al., "Reproducibility of internal atrial defibrillation threshold in paroxysmal and persistent atrial fibrillation," *Europace*, Jul. 2004; 6(4):267-72.
Violi et al., "Antioxidants for prevention of atrial fibrillation: a potentially useful future therapeutic approach? A review of the literature and meta-analysis," *Europace*, Aug. 2014; 16(8):1107-1116.
Weber et al., "Adenosine sensitive focal atrial tachycardia originating from the non-coronary aortic cusp," *Europace*, Jun. 2009; 11(6):823-6.
Weber et al., "Open-irrigated laser catheter ablation: relationship between the level of energy, myocardial thickness, and collateral damages in a dog model," *Europace*, Jan. 2014; 16(1):142-8.
Wegmoller, "Intra-Body Communication for Biomedical Sensor Networks," Diss. ETH, No. 17323, 1-173, 2007.
Wei et al., "Comparative simulation of excitation and body surface electrocardiogram with isotropic and anisotropic computer heart models," *IEEE Trans Biomed Eng.*, Apr. 1995; 42(4):343-57.
Weijs et al., "Clinical and echocardiographic correlates of intra-atrial conduction delay," *Europace*, Dec. 2011; 13(12):1681-7.
Weiss et al., "The influence of fibre orientation, extracted from different segments of the human left ventricle, on the activation and repolarization sequence: a simulation study," *Europace*, Nov. 2007; 9(Suppl. 6):vi96-vi104.
Wetzel et al., "A stepwise mapping approach for localization and ablation of ectopic right, left, and septal atrial foci using electroanatomic mapping," *European Heart Journal*, Sep. 2002; 23(17):1387-1393.
Wlodarska et al., "Thromboembolic complications in patients with arrhythmogenic right ventricular dysplasia/cardiomyopathy," *Europace*, Aug. 2006; 8(8):596-600.

(56) References Cited

OTHER PUBLICATIONS

Wong et al., "A review of mitral isthmus ablation," *Indian Pacing and Electrophysiology Journal*, 2012; 12(4):152-170.
Wu et al., "Acute and long-term outcome after catheter ablation of supraventricular tachycardia in patients after the Mustard or Senning operation for D-transposition of the great arteries," *Europace*, Jun. 2013; 15(6):886-91.
Xia et al., "Asymmetric dimethylarginine concentration and early recurrence of atrial fibrillation after electrical cardioversion," *Pacing Clin Electrophysiol.*, Aug. 2008; 31(8):1036-40.
Yamazaki et al., "Acute Regional Left Atrial Ischemia Causes Acceleration of Atrial Drivers during Atrial Fibrillation," *Heart Rhythm*, Jun. 2013; 10(6):901-9.
Yang et al., "Focal atrial tachycardia originating from the distal portion of the left atrial appendage: Characteristics and long-term outcomes of radiofrequency ablation," *Europace*, Feb. 2012; 14(2):254-60.
Yiginer et al., "Advanced Age, Female Gender and Delay in Pacemaker Implantation May Cause TdP in Patients With Complete Atrioventricular Block," *Indian Pacing and Electrophysiology Journal*, Oct. 2010; 10(10):454-63.
Yoon et al., "Measurement of thoracic current flow in pigs for the study of defibrillation and cardioversion," *IEEE Transactions on Biomedical Engineering*, Oct. 2003; 50(10):1167-1773.
Yuan et al., "Recording monophasic action potentials using a platinum-electrode ablation catheter," *Europace*, Oct. 2000; 2(4):312-9.
Yusuf et al., "5-Hydroxytryptamine and Atrial Fibrillation: How Significant is This Piece in the Puzzle?" *J Cardiovasc Electrophysiol.*, Feb. 2003; 14(2):209-14.
Zaugg et al., "Current concepts on ventricular fibrillation: a vicious circle of cardiomyocyte calcium overload in the initiation, maintenance, and termination of ventricular fibrillation," *Indian Pacing and Electrophysiology Journal*, Apr. 2004; 4(2):85-92.
Zhang et al., "Acute atrial arrhythmogenicity and altered Ca(2+) homeostasis in murine RyR2-P2328S hearts," *Cardiovascular Research*, Mar. 2011; 89(4):794-804.
Zoghi et al., "Electrical stunning and hibernation: suggestion of new terms for short- and long-term cardiac memory," *Europace*, Sep. 2004; 6(5):418-24.
Zografos et al., "Inhibition of the renin-angiotensin system for prevention of atrial fibrillation," *Pacing Clin Electrophysiol.*, Oct. 2010; 33(10):1270-85.
(PCT/US2014/066792) PCT Notification of Transmittal of the International Search Report and the Written Opinion of the International Searching Authority.
(PCT/US2014/013601) PCT Notification of Transmittal of the International Search Report and the Written Opinion of the International Searching Authority.
(PCT/US2014/036782) PCT Notification of Transmittal of the International Search Report and the Written Opinion of the International Searching Authority, Mailed Aug. 22, 2014, 11 pages.
International Search Report and Written Opinion for Application No. PCT/US2017/047378, 8 pages, date mailed Dec. 6, 2017.
(PCT/US2018/050988) PCT Notification of Transmittal of the International Search Report and the Written Opinion of the International Searching Authority, Mailed Nov. 14, 2018, 11 pages.
(PCT/US2018/050993) PCT Notification of Transmittal of the International Search Report and the Written Opinion of the International Searching Authority, mailed Nov. 16, 2018, 7 pages.
(PCT/US2019/023642) PCT Notification of Transmittal of the International Search Report and the Written Opinion of the International Searching Authority, mailed Jun. 28, 2019, 14 pages.
(PCT/US2019/064480) PCT Notification of Transmittal of International Search Report and Written Opinion, mailed Feb. 19, 2020, 12 pages.
http://www.isrctn.com/ISRCTN47824547, public posting published Aug. 2019.
Abed et al., "Obesity results in progressive atrial structural and electrical remodeling: Implications for atrial fibrillation," *Heart Rhythm Society*, Jan. 2013; 10(1):90-100.
Adragão et al., "Ablation of pulmonary vein foci for the treatment of atrial fibrillation; percutaneous electroanatomical guided approach," *Europace*, Oct. 2002; 4(4):391-9.
Aliot et al., "Arrhythmia detection by dual-chamber implantable cardioverter defibrillators: a review of current algorithms," *Europace*, Jul. 2004; 6(4):273-86.
Amirahmadi et al., "Ventricular Tachycardia Caused by Mesothelial Cyst," *Indian Pacing and Electrophysiology Journal*, 2013; 13(1):43-44.
Ammirabile et al., "Pitx2 confers left morphological, molecular, and functional identity to the sinus venosus myocardium," *Cardiovasc Res.*, Feb. 2012; 93(2):291-301.
Anfinsen, "Non-pharmacological Treatment of Atrial Fibrillation," *Indian Pacing and Electrophysiology Journal*, Jan. 2002; 2(1):4-14.
Anné et al., "Ablation of post-surgical intra-atrial reentrant Tachycardia," *European Heart Journal*, 2002; 23:169-1616.
Arenal et al., "Dominant frequency differences in atrial fibrillation patients with and without left ventricular systolic dysfunction," *Europace*, Apr. 2009; 11(4):450-457.
Arriagada et al., "Predictors of arrhythmia recurrence in patients with lone atrial fibrillation," *Europace*, Jan. 2008; 10(1):9-14.
Asirvatham et al., "Cardiac Anatomic Considerations in Pediatric Electrophysiology," *Indian Pacing and Electrophysiology Journal*, Apr. 2008; 8(Suppl 1):S75-S91.
Asirvatham et al., "Intramyocardial Pacing and Sensing for the Enhancement of Cardiac Stimulation and Sensing Specificity," *Pacing Clin. Electrophysiol.*, Jun. 2007; 30(6): 748-754.
Asirvatham et al., "Letter to the Editor," *J Cardiovasc Electrophysiol.*, Mar. 2010; 21(3): E77.
Balmer et al., "Long-term follow up of children with congenital complete atrioventricular block and the impact of pacemaker therapy," *Europace*, Oct. 2002; 4(4):345-349.
Barold et al., "Conventional and biventricular pacing in patients with first-degree atrioventricular block," *Europace*, Oct. 2012; 14(10):1414-9.
Barold et al., "The effect of hyperkalaemia on cardiac rhythm devices," *Europace*, Apr. 2014; 16(4):467-76.
Bayrak et al., "Added value of transoesophageal echocardiography during transseptal puncture performed by inexperienced operators," *Europace*, May 2012; 14(5):661-5.
Bergau et al., "Measurement of Left Atrial Pressure is a Good Predictor of Freedom From Atrial Fibrillation," *Indian Pacing and Electrophysiology Journal*, Jul. 2014; 14(4):181-93.
Bernstein et al., "The revised NASPE/BPEG generic code for antibradycardia, adaptive-rate, and multisite pacing. North American Society of Pacing and Electrophysiology/British Pacing and Electrophysiology Group," *Pacing Clin Electrophysiol.*, Feb. 2002; 25(2):260-4.

* cited by examiner

IMPLANTABLE MEDICAL DEVICE DELIVERY FOR CARDIAC THERAPY

RELATED APPLICATIONS

This application is a divisional of U.S. patent application Ser. No. 16/227,774, filed on Dec. 20, 2018, now abandoned, which is incorporated by reference herein in its entirety.

The present technology is generally related to implantable medical devices, systems, and methods. In particular, the present disclosure relates to delivering implantable medical devices to provide cardiac therapy.

The cardiac conduction system includes the sinus atrial (SA) node, the atrioventricular (AV) node, the bundle of His, bundle branches and Purkinje fibers. A heart beat is initiated in the SA node, which may be described as the natural "pacemaker" of the heart. An electrical impulse arising from the SA node causes the atrial myocardium to contract. The signal is conducted to the ventricles via the AV node which inherently delays the conduction to allow the atria to stop contracting before the ventricles begin contracting thereby providing proper AV synchrony. The electrical impulse is conducted from the AV node to the ventricular myocardium via the bundle of His, bundle branches, and Purkinje fibers.

Patients with a conduction system abnormality, such as poor AV node conduction or poor SA node function, may receive an implantable medical device (IMD), such as a pacemaker, to restore a more normal heart rhythm and AV synchrony. Some types of IMDs, such as cardiac pacemakers, implantable cardioverter defibrillators (ICDs), or cardiac resynchronization therapy (CRT) devices, provide therapeutic electrical stimulation to a heart of a patient via electrodes on one or more implantable endocardial, epicardial, or coronary venous leads that are positioned in or adjacent to the heart. The therapeutic electrical stimulation may be delivered to the heart in the form of pulses or shocks for pacing, cardioversion, or defibrillation. In some cases, an IMD may sense intrinsic depolarizations of the heart, and control the delivery of therapeutic stimulation to the heart based on the sensing.

Delivery of therapeutic electrical stimulation to the heart can be useful in addressing cardiac conditions such as ventricular dyssynchrony that may occur in patients. Ventricular dyssynchrony may be described as a lack of synchrony or a difference in the timing of contractions in different ventricles of the heart. Significant differences in timing of contractions can reduce cardiac efficiency. CRT, delivered by an IMD to the heart, may enhance cardiac output by resynchronizing the electromechanical activity of the ventricles of the heart. CRT is sometimes referred to as "triple chamber pacing" because of pacing the right atrium, right ventricle, and left ventricle.

Cardiac arrhythmias may be treated by delivering electrical shock therapy for cardioverting or defibrillating the heart in addition to cardiac pacing, for example, from an ICD, which may sense a patient's heart rhythm and classify the rhythm according to an arrhythmia detection scheme in order to detect episodes of tachycardia or fibrillation. Arrhythmias detected may include ventricular tachycardia (VT), fast ventricular tachycardia (FVT), ventricular fibrillation (VF), atrial tachycardia (AT) and atrial fibrillation (AT). Anti-tachycardia pacing (ATP), a painless therapy, can be used to treat ventricular tachycardia (VT) to substantially terminate many monomorphic fast rhythms. While ATP is painless, ATP may not deliver effective therapy for all types of VTs. For example, ATP may not be as effective for polymorphic VTs, which has variable morphologies. Polymorphic VTs and ventricular fibrillation (VFs) can be more lethal and may require expeditious treatment by shock.

Dual chamber medical devices are available that include a transvenous atrial lead carrying electrodes that may be placed in the right atrium and a transvenous ventricular lead carrying electrodes that may be placed in the right ventricle via the right atrium. The dual chamber medical device itself is generally implanted in a subcutaneous pocket and the transvenous leads are tunneled to the subcutaneous pocket. A dual chamber medical device may sense atrial electrical signals and ventricular electrical signals and can provide both atrial pacing and ventricular pacing as needed to promote a normal heart rhythm and AV synchrony. Some dual chamber medical devices can treat both atrial and ventricular arrhythmias.

Intracardiac medical devices, such as a leadless pacemaker, have been introduced or proposed for implantation entirely within a patient's heart, eliminating the need for transvenous leads. A leadless pacemaker may include one or more electrodes on its outer housing to deliver therapeutic electrical signals and/or sense intrinsic depolarizations of the heart. Intracardiac medical devices may provide cardiac therapy functionality, such as sensing and pacing, within a single chamber of the patient's heart. Single chamber intracardiac devices may also treat either atrial or ventricular arrhythmias or fibrillation. Some leadless pacemakers are not intracardiac and may be positioned outside of the heart and, in some examples, may be anchored to a wall of the heart via a fixation mechanism.

In some patients, single chamber devices may adequately address the patient's needs. However, single chamber devices capable of only single chamber sensing and therapy may not fully address cardiac conduction disease or abnormalities in all patients, for example, those with some forms of AV dyssynchrony or tachycardia. Dual chamber sensing and/or pacing functions, in addition to ICD functionality in some cases, may be used to restore more normal heart rhythms.

SUMMARY

The techniques of this disclosure generally relate to delivering implantable medical devices to provide cardiac therapy using the cardiac conduction system or left ventricular myocardium implantable, for example, through the right atrium to the left ventricle (e.g., ventricle-from-atrium, or VfA) or through the coronary sinus. Various non-limiting examples of cardiac therapy include single chamber or multiple chamber pacing (e.g., dual or triple chamber pacing), atrioventricular synchronous pacing, asynchronous pacing, triggered pacing, cardiac resynchronization pacing, or tachycardia-related therapy. In general, a tissue-piercing electrode is implantable in the basal region, septal region, or basal-septal region adjacent to or within the left ventricular myocardium of the patient's heart. The tissue-piercing electrode, or another imagable member, may be at least partially formed of an imagable material.

In one aspect, the present disclosure provides an implantable medical device including one or more electrodes including a tissue-piercing electrode implantable to deliver cardiac therapy to or sense electrical activity of the left ventricle in the basal region, septal region, or basal-septal region of the left ventricular myocardium of a patient's heart. The tissue-piercing electrode is at least partially made of an imagable material. The device also includes a therapy delivery circuit operably coupled to the one or more electrodes to deliver cardiac therapy to the patient's heart; a sensing circuit operably coupled to the one or more electrodes to sense electrical activity of the patient's heart; and a controller including processing circuitry operably coupled to the therapy delivery circuit and the sensing circuit. The controller is configured to: sense electrical activity using one or more electrodes; and deliver cardiac therapy based on the sensed electrical activity.

In another aspect, the present disclosure provides an implantable medical device including one or more electrodes including a tissue-piercing electrode implantable to deliver cardiac therapy to or sense electrical activity of the left ventricle in the basal region, septal region, or basal-septal region of the left ventricular myocardium of a patient's heart. The device also includes an imagable member at least partially made of an imagable material coupled to a housing or a lead configured, when viewed using two-dimensional imaging, to provide orientation information in a third dimension orthogonal to the two dimensions. The device further includes a therapy delivery circuit operably coupled to the one or more electrodes to deliver cardiac therapy to the patient's heart; a sensing circuit operably coupled to the one or more electrodes to sense electrical activity of the patient's heart; and a controller including processing circuitry operably coupled to the therapy delivery circuit and the sensing circuit. The controller is configured to: sense electrical activity using the one or more electrodes; and deliver cardiac therapy based on the sensed electrical activity.

In another aspect, the present disclosure provides an implantation method that includes advancing an implantable medical device including a tissue-piercing electrode toward the triangle of Koch region of the right atrium through the right atrial endocardium and central fibrous body or through the coronary sinus to deliver cardiac therapy to or sense electrical activity of the left ventricle in the basal region, septal region, or basal-septal region of the left ventricular myocardium of a patient's heart. The tissue-piercing electrode includes an imagable material or the implantable medical device includes an imagable member at least partially made of an imagable material coupled to a housing or a lead of the implantable medical device. The method also includes acquiring image information representing the patient's heart and the imagable material using two-dimensional imaging; and generating orientation information representing the implantable medical device based on the acquired image information.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
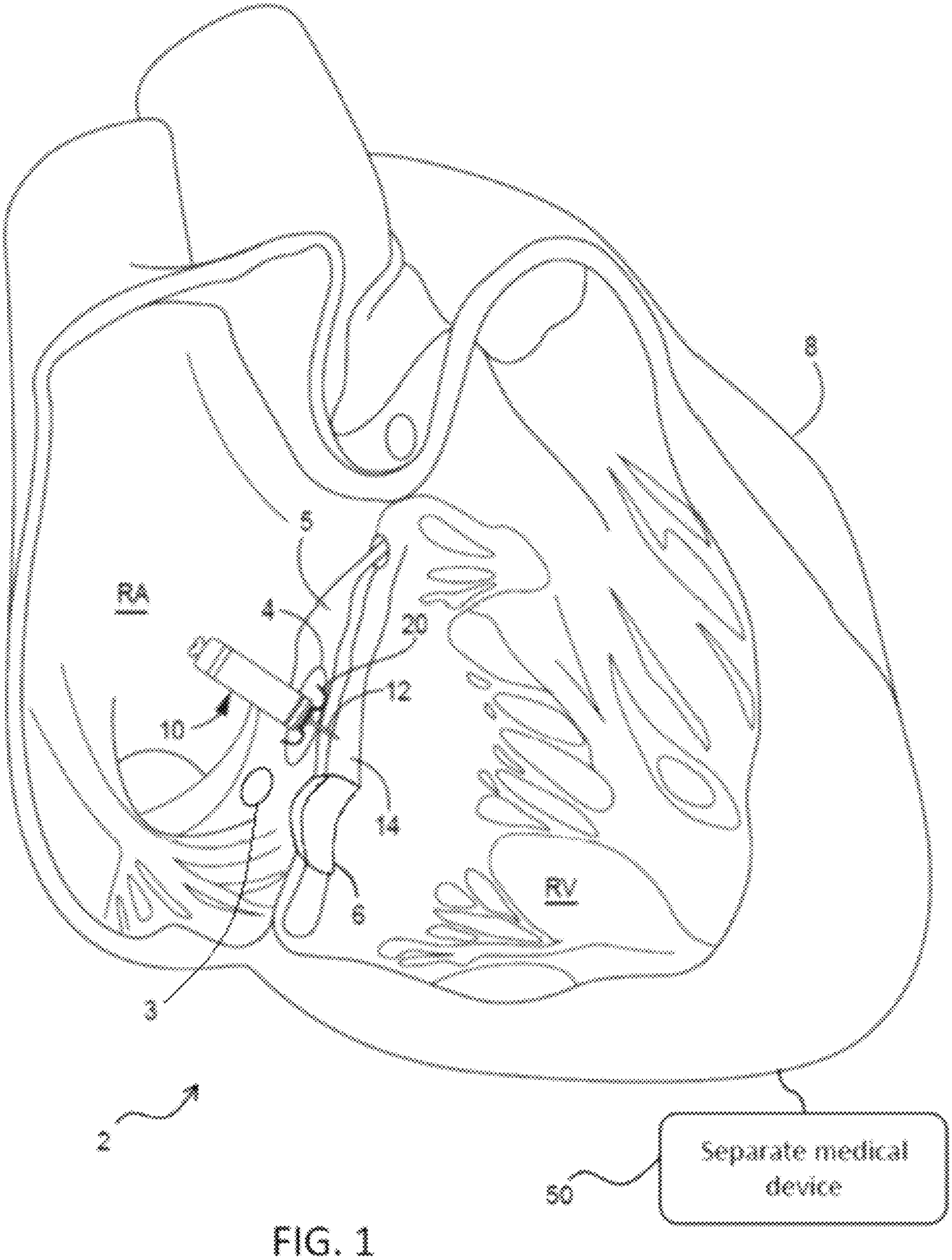
FIG. 1 is a conceptual diagram of an illustrative cardiac therapy system including an intracardiac medical device implanted in a patient's heart and a separate medical device positioned outside of the patient's heart for use with, e.g., the illustrative methods of FIGS. 24-25.

The techniques of this disclosure generally relate to delivering implantable medical devices to provide cardiac therapy using the cardiac conduction system or left ventricular myocardium implantable, for example, through the right atrium to the left ventricle (e.g., ventricle-from-atrium, or VfA) or through the coronary sinus. In some embodiments, various techniques described herein may be applied to His bundle or bundle branch pacing applications. Various non-limiting examples of cardiac therapy include single chamber or multiple chamber pacing (e.g., dual or triple chamber pacing), atrioventricular synchronous pacing, asynchronous pacing, triggered pacing, cardiac resynchronization pacing, or tachycardia-related therapy. Although reference is made herein to implantable medical devices, such as a pacemaker or ICD, the methods and processes may be used with any medical devices, systems, or methods related to a patient's heart. Various other applications will become apparent to one of skill in the art having the benefit of the present disclosure.

It may be beneficial to provide an implantable medical device delivery system and technique to locate an electrode for sensing or pacing the left ventricular myocardium or the cardiac conduction system. It may be beneficial to provide an implantable medical device that is free of transvenous leads (e.g., a leadless device). It may also be beneficial to provide an implantable medical device capable of being used for various cardiac therapies, such as single or multiple chamber pacing (e.g., dual- or triple-chamber pacing), atrioventricular synchronous pacing, asynchronous pacing, triggered pacing, cardiac resynchronization pacing, or tachycardia-related therapy. Further, it may be beneficial to provide a technique for delivering a medical device to the triangle of Koch region in the right atrium or to the cardiac conduction system in an accurate and precise manner to facilitate pacing the endocardium and/or the His bundle conduction system.

As used herein, the term "capture" in the context of pacing (e.g., effective capture of the heart from pacing) refers to determining whether a desired response is sensed in response to stimuli, such as sensing desirable electrical activity in response to electrical pulses delivered to a portion of the heart.

As used herein, the term "effective" generally refers to meeting conditions that would be sufficient to a person of ordinary skill in the art for performing a particular function. For example, effective pacing of the left ventricle may result in capture of the left ventricle when electrical or mechanical activity of the left ventricle is sensed and determined to provide cardiac therapy as desired.

The present disclosure provides a technique for implanting a tissue-piercing electrode in the basal region, septal region, or basal-septal region adjacent to or within the left ventricular myocardium of the patient's heart. In particular, the tissue-piercing electrode may be positioned to sense or pace the cardiac conduction system or left ventricular myocardium and be implantable, for example, through the right atrium to the left ventricle or through the coronary sinus. The tissue-piercing electrode, or another imagable member, may be at least partially formed of an imagable material. The technique may include using an imaging device to acquire two-dimensional (2D) imaging data and three-dimensional (3D) information (e.g., orientation information) may be generated from the 2D imaging data that represents the implantable medical device.

In some embodiments, the tissue-piercing electrode may be implanted in the basal region, septal region, or basal-septal region of the left ventricular myocardium of the patient's heart from the triangle of Koch region of the right atrium through the right-atrial endocardium and central fibrous body. In a leadless implantable medical device, the tissue-piercing electrode may leadlessly extend from a distal end region of a housing of the device, and the right-atrial electrode may be leadlessly coupled to the housing (e.g., part of or positioned on the exterior of the housing). The right-atrial motion detector may be within the implantable medical device. In a leaded implantable medical device, one or more of the electrodes may be coupled to the housing using an implantable lead. When the device is implanted, the electrodes may be used to sense electrical activity in one or more atria and/or ventricles of a patient's heart. The motion detector may be used to sense mechanical activity in one or more atria and/or ventricles of the patient's heart. In particular, the activity of the right atrium and the left ventricle may be sensed and, optionally, the activity of the right ventricle may be sensed. In general, electrical or mechanical activity may be sensed, determined, acquired, or monitored using various techniques available to one having ordinary skill in the art who has the benefit of the present disclosure. As used herein, the term "monitoring" generally refers to sensing, acquiring, or receiving data or information that may be used, for example, being processed or stored.

The electrodes may be used to deliver cardiac therapy, such as single-chamber pacing for atrial fibrillation, atrioventricular synchronous pacing for bradycardia, asynchronous pacing, triggered pacing, cardiac resynchronization pacing for ventricular dyssynchrony, anti-tachycardia pacing, or shock therapy. Shock therapy may be initiated by the implantable medical device. A separate medical device, such as an extravascular ICD, which may also be implanted, may be in operative communication with the implantable medical device and may deliver an electrical shock in response to a trigger, such as a signaling pulse (e.g., triggering, signaling, or distinctive electrical pulse) provided by the device.

The present disclosure also provides a technique to deliver and implant a medical device, for example, in the triangle of Koch region in the right atrium. Various devices may be used to identify the general location of the triangle of Koch region, which may be described as an implantation site. A flexible lead, or another probe, may be advanced to the potential implantation site and used to identify a precise location for implantation of a medical device, such as an electrode, leadlet, lead, or intracardiac device. In particular, the techniques of the present disclosure may be used to implant a device to provide synchronous pacing to patients with dyssynchrony, as well as provide dual chamber pacing for bradycardia patients with moderate heart failure.

Figure 24:
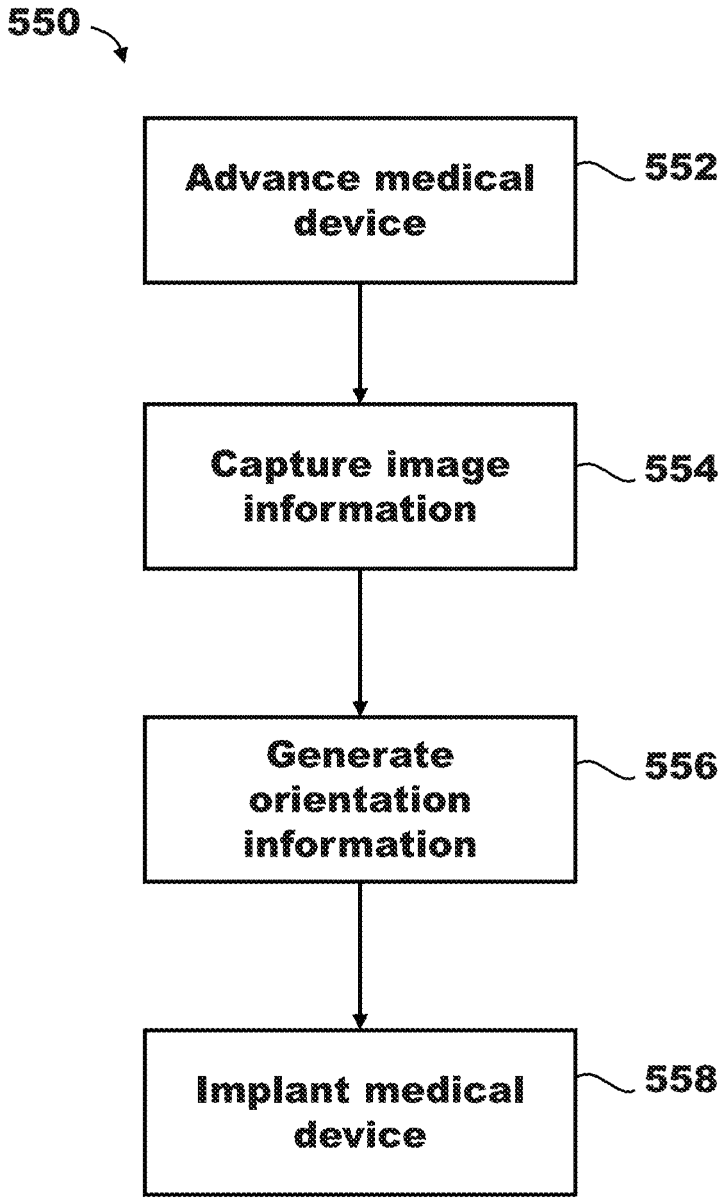
FIG. 24 is a flow diagram showing one example of a method of delivering an implantable medical device of, e.g., the illustrative systems and devices of FIGS. 1-4 and FIG. 16.
Figure 25:
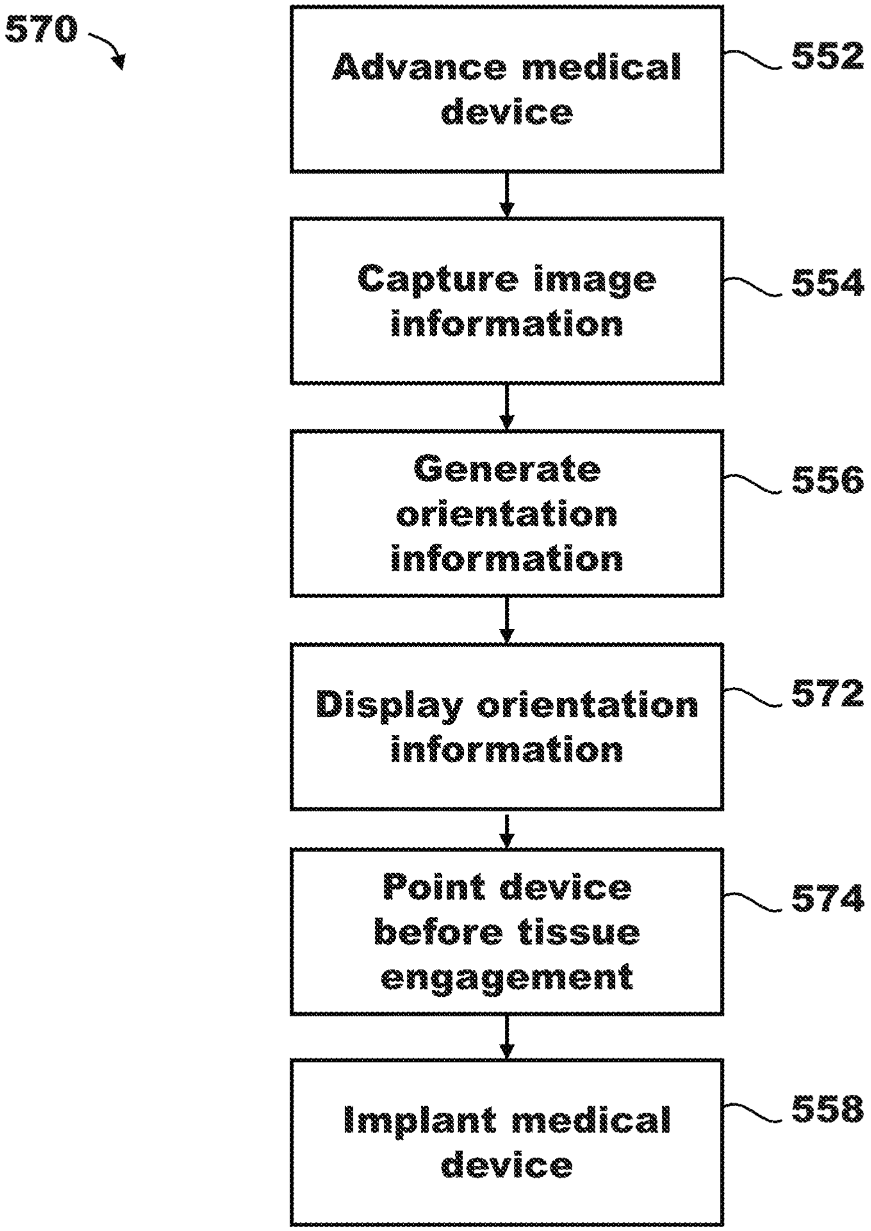
FIG. 25 is a flow diagram showing another example of a method of delivering an implantable medical device of, e.g., the illustrative systems and devices of FIGS. 1-4 and FIG. 16.

FIGS. 1-4 show examples of various cardiac therapy systems that may be implanted using, for example, the methods shown in FIGS. 24-25 to deliver a medical device to an implantation site. In these views, the left ventricle (LV) is positioned generally behind the right ventricle (RV).

Although the present disclosure describes leadless and leaded implantable medical devices, reference is first made to FIG. 1, which shows a conceptual diagram of a cardiac therapy system 2 including an intracardiac medical device 10 that may be configured for single or dual chamber therapy and implanted in a patient's heart 8. In some embodiments, the device 10 may be configured for single-chamber pacing and may, for example, switch between single-chamber and multiple-chamber pacing (e.g., dual- or triple-chamber pacing). As used herein, "intracardiac" refers to a device configured to be implanted entirely within a patient's heart, for example, to provide cardiac therapy. The device 10 is shown implanted in the right atrium (RA) of the patient's heart 8 in a target implant region 4. The device 10 may include one or more fixation members 20 that anchor a distal end of the device against the atrial endocardium in a target implant region 4. The target implant region 4 may lie between the His bundle 5 (or bundle of His) and the coronary sinus 3 and may be adjacent the tricuspid valve 6. The device 10 may be described as a ventricle-from-atrium (VfA) device, which may sense or provide therapy to one or both ventricles (e.g., right ventricle, left ventricle, or both ventricles, depending on the circumstances) while being generally disposed in the right atrium. In particular, the device 10 may include a tissue-piercing electrode that may be implanted in the basal region, septal region, or basal-septal region of the left ventricular myocardium of the patient's heart from the triangle of Koch region of the right atrium through the right-atrial endocardium and central fibrous body.

The device 10 may be described as a leadless implantable medical device. As used herein, "leadless" refers to a device being free of a lead extending out of the patient's heart 8. In other words, a leadless device may have a lead that does not extend from outside of the patient's heart to the inside of the patient's heart. Some leadless devices may be introduced through a vein, but once implanted, the device is free of, or may not include, any transvenous lead and may be configured to provide cardiac therapy without using any transvenous lead. Further, a leadless VfA device, in particular, does not use a lead to operably connect to an electrode in the ventricle when a housing of the device is positioned in the atrium. Additionally, a leadless electrode may be coupled to the housing of the medical device without using a lead between the electrode and the housing.

The device 10 may include a dart electrode assembly 12 defining, or having, a straight shaft extending from the distal end region of device 10. The dart electrode assembly 12 may be placed, or at least configured to be placed, through the atrial myocardium and the central fibrous body and into the ventricular myocardium 14, or along the ventricular septum, without perforating entirely through the ventricular endocardial or epicardial surfaces. The dart electrode assembly 12 may carry, or include, an electrode at the distal end region of the shaft such that the electrode may be positioned within the ventricular myocardium for sensing ventricular signals and delivering ventricular pulses (e.g., to depolarize the left ventricle to initiate a contraction of the left ventricle). In some examples, the electrode at the distal end region of the shaft is a cathode electrode provided for use in a bipolar electrode pair for pacing and sensing. While the implant region 4 as illustrated may enable one or more electrodes of the dart electrode assembly 12 to be positioned in the ventricular myocardium, it is recognized that a device having the aspects disclosed herein may be implanted at other locations for multiple chamber pacing (e.g., dual- or triple-chamber pacing), single-chamber pacing with multiple chamber sensing, single-chamber pacing and/or sensing, or other clinical therapy and applications as appropriate.

One or more portions, or all, of various components, such as the dart electrode assembly 12 (e.g., tissue-piercing electrode), the one or more fixation members 20, or any other suitable structure, may be at least partially made, or formed, of an imagable material. Such components may be described as imagable members. One example of an imagable material is a radiopaque material, which may be described as a material that is substantially radiopaque or substantially more radiopaque than other nearby structures during implantation. For example, the imagable material may include radiopaque properties that are visible using x-ray fluoroscopy. Non-limiting examples of imagable material include gold, platinum/iridium, or a polymer loaded with at least 75% tungsten. In some embodiments, the imagable materials include an appropriate radiopaque material such as a metal (e.g., stainless steel, tungsten, gold, platinum iridium, or other appropriate biocompatible materials), radiopaque polymer fibers, radiopaque fill fibers, polymers with radiopaque additives, or the like.

Such imagable materials may assist in resolution, such as a higher contrast, of the image of the imagable member. In general, the imagable member may be high in contrast in an x-ray image compared to other components of the device 10. The imagable member may be surrounded by materials that are not very radiopaque to facilitate higher contrast for efficient visualization.

Further, the geometry, such as a cross sectional geometry, of the imagable member may assist in resolution of the imagable member. Various cross-sectional geometries include hexagon, round, square, and trapezoid. In some embodiments, the imagable member may include a helical, or coil, shape to facilitate determining the orientation of the device 10. For example, a thread of a screw or a coiled spring can generally define a helical shape that can define a template for forming the helical shape of the imagable member.

In some embodiments, a tissue-piercing electrode of the dart electrode assembly 12 may be at least partially formed of the imagable material. In some embodiments, the one or more fixation members 20 may be formed of the imagable material. In some embodiments, an imagable member may be disposed on an outer surface of a housing of the device 10 (e.g., using sputtering). In some embodiments, an imagable member may be disposed inside of the housing of the device 10, for example, on an inner surface of the housing.

It is to be understood that although device 10 is described herein as including a single dart electrode assembly, the device 10 may include more than one dart electrode assembly placed, or configured to be placed, through the atrial myocardium and the central fibrous body, and into the ventricular myocardium 14, or along the ventricular septum, without perforating entirely through the ventricular endocardial or epicardial surfaces. Additionally, each dart electrode assembly may carry, or include, more than a single electrode at the distal end region, or along other regions (e.g., proximal or central regions), of the shaft.

The cardiac therapy system 2 may also include a separate medical device 50 (depicted diagrammatically in FIG. 1), which may be positioned outside the patient's heart 8 (e.g., subcutaneously) and may be operably coupled to the patient's heart 8 to deliver cardiac therapy thereto. In one example, separate medical device 50 may be an extravascular ICD. In some embodiments, an extravascular ICD may include a defibrillation lead including, or carrying, a defibrillation electrode. A therapy vector may exist between the defibrillation electrode on the defibrillation lead and a housing electrode of the ICD. Further, one or more electrodes of the ICD may also be used for sensing electrical signals related to the patient's heart 8. The ICD may be configured to deliver shock therapy including one or more defibrillation or cardioversion shocks. For example, if an arrhythmia is sensed, the ICD may send a pulse via the electrical lead wires to shock the heart and restore its normal rhythm. In some examples, the ICD may deliver shock therapy without placing electrical lead wires within the heart or attaching electrical wires directly to the heart (subcutaneous ICDs). Examples of extravascular, subcutaneous ICDs that may be used with the system 2 described herein may be described in U.S. Pat. No. 9,278,229 (Reinke et al.), issued 8 Mar. 2016, which is incorporated herein by reference in its entirety.

In the case of shock therapy (e.g., defibrillation shocks provided by the defibrillation electrode of the defibrillation lead), the separate medical device 50 (e.g., extravascular ICD) may include a control circuit that uses a therapy delivery circuit to generate defibrillation shocks having any of a number of waveform properties, including leading-edge voltage, tilt, delivered energy, pulse phases, and the like. The therapy delivery circuit may, for instance, generate monophasic, biphasic, or multiphasic waveforms. Additionally, the therapy delivery circuit may generate defibrillation waveforms having different amounts of energy. For example, the therapy delivery circuit may generate defibrillation waveforms that deliver a total of between approximately 60-80 Joules (J) of energy for subcutaneous defibrillation.

The separate medical device 50 may further include a sensing circuit. The sensing circuit may be configured to obtain electrical signals sensed via one or more combinations of electrodes and to process the obtained signals. The components of the sensing circuit may include analog components, digital components, or a combination thereof. The sensing circuit may, for example, include one or more sense amplifiers, filters, rectifiers, threshold detectors, analog-to-digital converters (ADCs), or the like. The sensing circuit may convert the sensed signals to digital form and provide the digital signals to the control circuit for processing and/or analysis. For example, the sensing circuit may amplify signals from sensing electrodes and may convert the amplified signals to multi-bit digital signals by an ADC, and then provide the digital signals to the control circuit. In one or more embodiments, the sensing circuit may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to the control circuit.

The device 10 and the separate medical device 50 may cooperate to provide cardiac therapy to the patient's heart 8. For example, the device 10 and the separate medical device 50 may be used to detect tachycardia, monitor tachycardia, and/or provide tachycardia-related therapy. For example, the device 10 may communicate with the separate medical device 50 wirelessly to trigger shock therapy using the separate medical device 50. As used herein, "wirelessly" refers to an operative coupling or connection without using a metal conductor between the device 10 and the separate medical device 50. In one example, wireless communication may use a distinctive, signaling, or triggering electrical-pulse provided by the device 10 that conducts through the patient's tissue and is detectable by the separate medical device 50. In another example, wireless communication may use a communication interface (e.g., an antenna) of the device 10 to provide electromagnetic radiation that propagates through patient's tissue and is detectable, for example, using a communication interface (e.g., an antenna) of the separate medical device 50.

Figure 2:
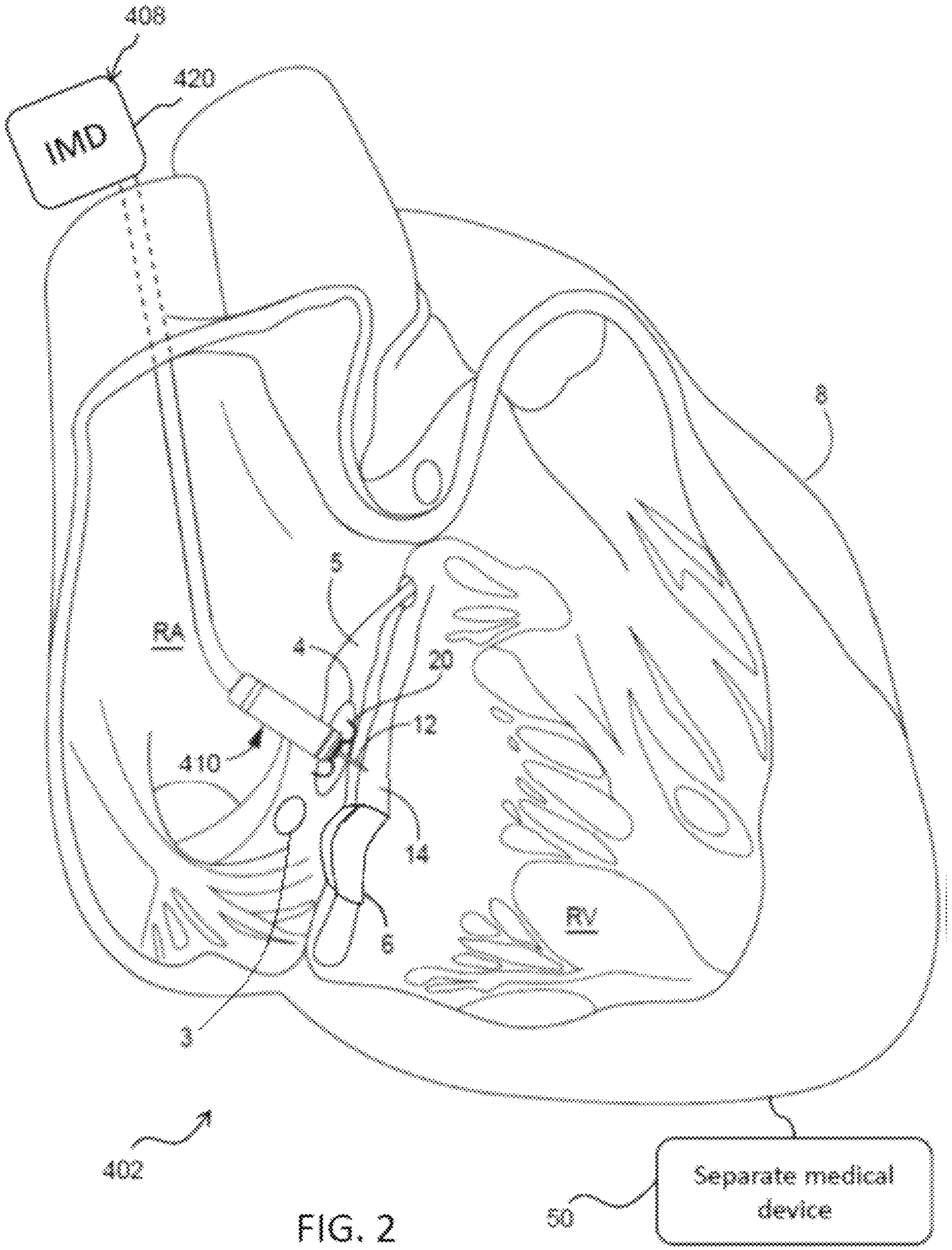
FIGS. 2-4 are conceptual diagrams of illustrative cardiac therapy systems including medical devices including leads with electrodes implanted in a patient's heart for use with, e.g., the illustrative methods of FIGS. 24-25.

With reference to FIG. 2, a cardiac therapy system 402 may include a leaded medical device 408 including one, or a single, implantable lead 410 having a tissue-piercing electrode assembly 12 coupled to a distal end region of the lead and implanted inside the patient's heart 8. The housing 420 of the leaded medical device 408 may be implanted and positioned outside of the patient's heart 8 and be configured to calibrate pacing therapy and/or deliver pacing therapy. The lead 410 may include a right-atrial electrode, and the device 408 may operate as a dual-channel capable device (e.g., pacing and/or sensing in both the right atrium and left ventricle). In some embodiments, the lead 410 may not include a right-atrial electrode. In other words, the leaded medical device 408 may be a single channel device, which may be used for asynchronous, triggered, or another type of single-channel pacing. The leaded medical device 408, using the lead 410, may sense activity or deliver pacing to the left ventricle (LV) when the tissue-piercing electrode assembly 12 is implanted, for example, in the same or similar manner as described with respect to FIG. 1.

Figure 3:
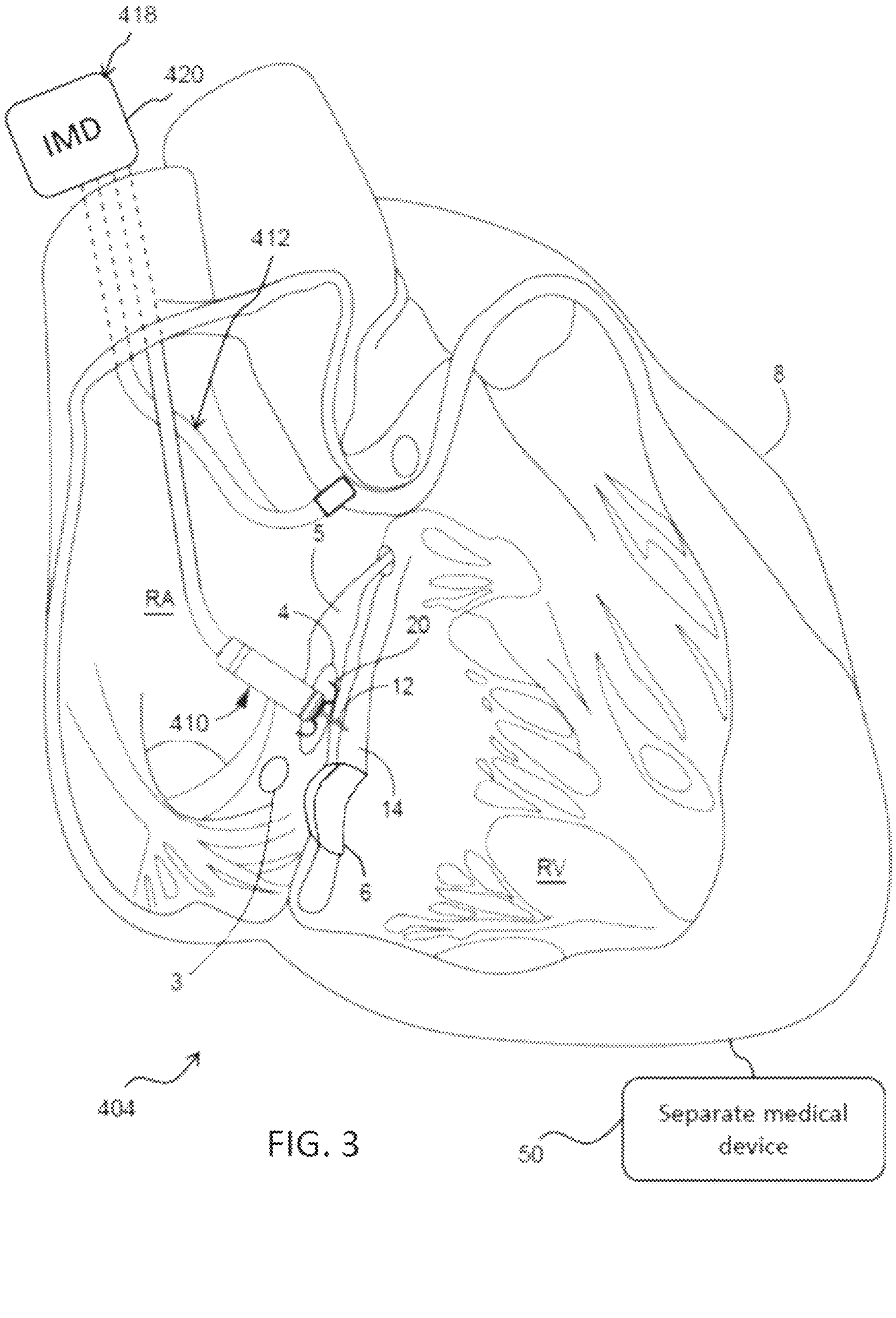

With reference to FIG. 3, a cardiac therapy system 404 may include a leaded medical device 418 similar to the leaded medical device 408 of FIG. 2, except that device 418 includes two implantable leads 410, 412. In particular, implantable lead 412 may include an electrode (e.g., a right-atrial electrode) coupled to a distal end region of the lead 412 and may be implanted in a different location than lead 410. In some embodiments, lead 412 is implanted in a different region of the right atrium. In some embodiments, each lead 410, 412 may contribute one channel of a dual-channel device 418. For example, lead 410 may sense activity or deliver pacing to the left ventricle (LV) when the tissue-piercing electrode of the tissue-piercing electrode assembly 12 is implanted, for example, in the same or similar manner as described with respect to FIG. 1, and lead 412 may sense activity or deliver pacing to the right atrium (RA).

Figure 4:
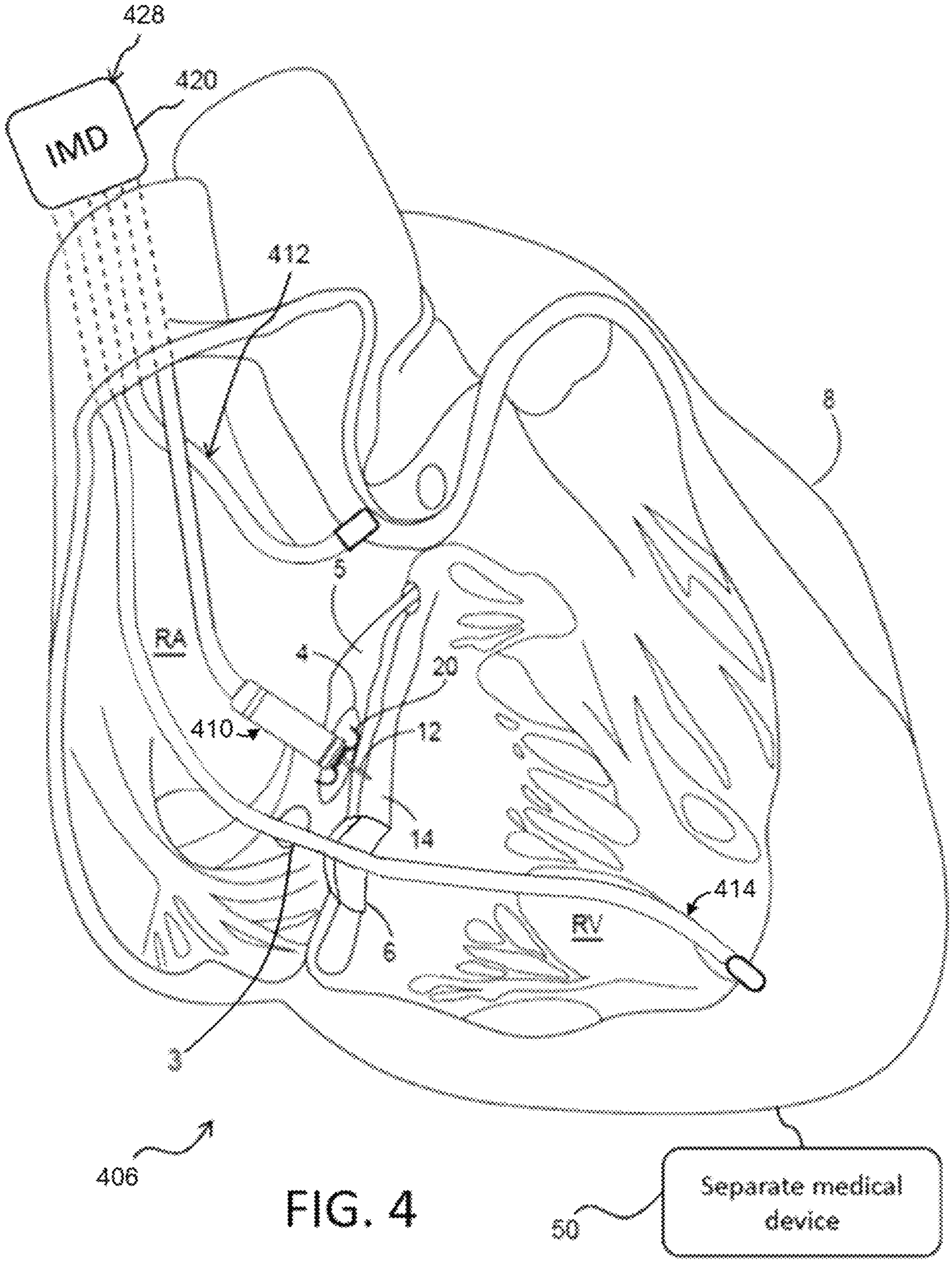

With reference to FIG. 4, a cardiac therapy system 406 may include a leaded medical device 428 similar to the leaded medical device 418 of FIG. 3 except that device 428 includes three implantable leads 410, 412, 414. In particular, implantable lead 414 may include an electrode (e.g., a right ventricular electrode) coupled to a distal end region of the lead 414 and may be implanted in a different location than leads 410, 412. As illustrated, implantable lead 414 extends from the right atrium (RA) to the right ventricle (RV) through tricuspid valve 6. In some embodiments, lead 414 is implanted in a region of the right ventricle. In some embodiments, each lead 410, 412, 414 may contribute one channel to a multi-channel device 428. For example, lead 410 may sense activity or deliver pacing to the left ventricle (LV) when the tissue-piercing electrode assembly 12 is implanted, for example, in the same or similar manner as described with respect to FIG. 1, lead 412 may sense activity from the delivery of pacing to the RA, and lead 414 may sense activity or deliver pacing to the RV.

In some embodiments, a pacing delay between the RV electrode on lead 414 to pace the RV and the LV electrode on lead 410 to pace the LV (e.g., RV-LV pacing delay, or more generally, VV pacing delay) may be calibrated or optimized, for example, using a separate medical device, such as an electrode apparatus (e.g., ECG belt). Various methods may be used to calibrate or optimize the VV delay. In some embodiments, the medical device 428 may be used to test pacing at a plurality of different VV delays. For example, the RV may be paced ahead of the LV by about 80, 60, 40, and 20 milliseconds (ms) and the LV may be paced ahead of the RV by about 80, 60, 40, and 20 ms, as well as simultaneous RV-LV pacing (e.g., about 0 ms VV pacing delay). The medical device 428 may then be configured, for example, automatically, to select a VV pacing delay that, when used for pacing, corresponds to a minimal electrical dyssynchrony measured using the electrode apparatus. The test pacing at different VV pacing delays may be performed using a particular AV delay, such as a nominal AV delay set by the medical device 428 or at a predetermined optimal AV delay based on patient characteristics.

Figure 5:
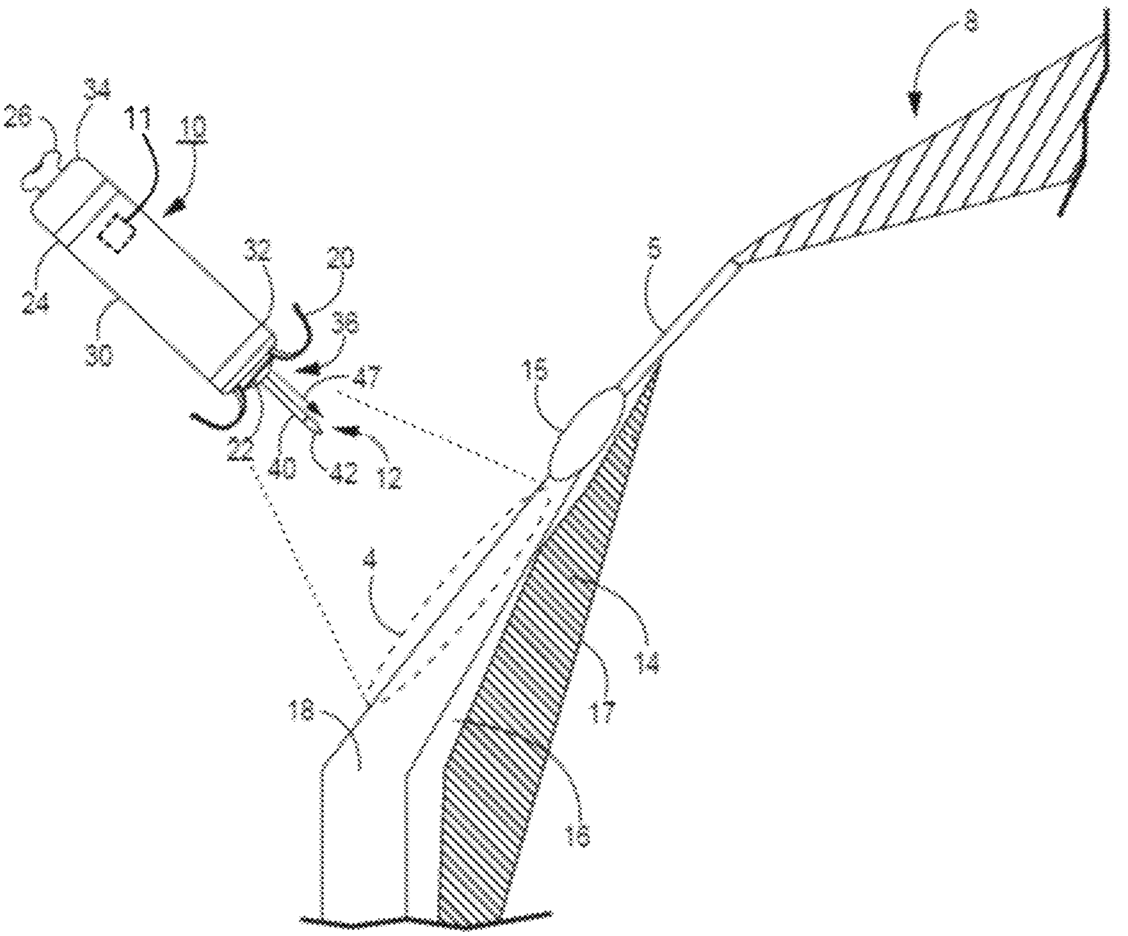
FIG. 5 is an enlarged conceptual diagram of the intracardiac medical device of FIG. 1 and anatomical structures of the patient's heart.

FIG. 5 is an enlarged conceptual diagram of the intracardiac medical device 10 of FIG. 1 and anatomical structures of the patient's heart 8. In particular, the device 10 is configured to sense electrical activity and/or deliver pacing therapy. The intracardiac device 10 may include a housing 30. The housing 30 may define a hermetically-sealed internal cavity in which internal components of the device 10 reside, such as a sensing circuit, therapy delivery circuit, control circuit, memory, telemetry circuit, other optional sensors, and a power source as generally described in conjunction with FIG. 8. The housing 30 may be formed from an electrically conductive material including titanium or titanium alloy, stainless steel, MP35N (a non-magnetic nickel-cobalt-chromium-molybdenum alloy), platinum alloy, or other bio-compatible metal or metal alloy. In other examples, the housing 30 may be formed from a non-conductive material including ceramic, glass, sapphire, silicone, polyurethane, epoxy, acetyl co-polymer plastics, polyether ether ketone (PEEK), a liquid crystal polymer, or other biocompatible polymer.

In at least one embodiment, the housing 30 may be described as extending between a distal end region 32 and a proximal end region 34 in a generally cylindrical shape to facilitate catheter delivery. In other embodiments, the housing 30 may be prismatic or any other shape to perform the functionality and utility described herein. The housing 30 may include a delivery tool interface member 26, e.g., at the proximal end region 34, for engaging with a delivery tool during implantation of the device 10.

All or a portion of the housing 30 may function as an electrode during cardiac therapy, for example, in sensing and/or pacing. In the example shown, the housing-based electrode 24 is shown to circumscribe a proximal portion (e.g., closer to the proximal end region 34 than the distal end region 32) of the housing 30. When the housing 30 is formed from an electrically conductive material, such as a titanium alloy or other examples listed above, portions of the housing 30 may be electrically insulated by a non-conductive material, such as a coating of parylene, polyurethane, silicone, epoxy, or other biocompatible polymer, leaving one or more discrete areas of conductive material exposed to define the proximal housing-based electrode 24. When the housing 30 is formed from a non-conductive material, such as a ceramic, glass or polymer material, an electrically conductive coating or layer, such as a titanium, platinum, stainless steel, or alloys thereof, may be applied to one or more discrete areas of the housing 30 to form the proximal housing-based electrode 24. In other examples, the proximal housing-based electrode 24 may be a component, such as a ring electrode, that is mounted or assembled onto the housing 30. The proximal housing-based electrode 24 may be electrically coupled to internal circuitry of the device 10, e.g., via the electrically-conductive housing 30 or an electrical conductor when the housing 30 is a non-conductive material.

In the example shown, the proximal housing-based electrode 24 is located nearer to the housing proximal end region 34 than the housing distal end region 32 and is therefore referred to as a "proximal housing-based electrode" 24. In other examples, however, the housing-based electrode 24 may be located at other positions along the housing 30, e.g., more distal relative to the position shown.

At the distal end region 32, the device 10 may include a distal fixation and electrode assembly 36, which may include one or more fixation members 20 and one or more dart electrode assemblies 12 of equal or unequal length. In one example, a single dart electrode assembly 12 includes a shaft 40 extending distally away from the housing distal end region 32 and one or more electrode elements, such as a tip electrode 42 at or near the free, distal end region of the shaft 40. The tip electrode 42 may have a conical or hemispherical distal tip with a relatively narrow tip-diameter (e.g., less than about 1 millimeter (mm)) for penetrating into and through tissue layers without using a sharpened tip or needle-like tip having sharpened or beveled edges.

The shaft 40 of the dart electrode assembly 12 may be a normally straight member and may be rigid. In other embodiments, the shaft 40 may be described as being relatively stiff but still possessing limited flexibility in lateral directions. Further, the shaft 40 may be non-rigid to allow some lateral flexing with heart motion. However, in a relaxed state, when not subjected to any external forces, the shaft 40 may maintain a straight position as shown to hold the tip electrode 42 spaced apart from the housing distal end region 32 at least by the height 47 of the shaft 40. In other words, the dart electrode assembly 12 may be described as resilient.

The dart electrode assembly 12 may be configured to pierce through one or more tissue layers to position the tip electrode 42 within a desired tissue layer, e.g., the ventricular myocardium. As such, the height 47, or length, of the shaft 40 may correspond to the expected pacing site depth, and the shaft 40 may have a relatively high compressive strength along its longitudinal axis to resist bending in a lateral or radial direction when pressed against the implant region 4. If a second dart electrode assembly 12 is employed, its length may be unequal to the expected pacing site depth and may be configured to act as an indifferent electrode for delivering of pacing energy to the tissue. A longitudinal axial force may be applied against the tip electrode 42, e.g., by applying a longitudinal pushing force to the proximal end region 34 of the housing 30, to advance the dart electrode assembly 12 into the tissue within the target implant region. The shaft 40 may be described as longitudinally non-compressive and/or elastically deformable in lateral or radial directions when subjected to lateral or radial forces to allow temporary flexing, e.g., with tissue motion, but may return to its normally straight position when lateral forces diminish. When the shaft 40 is not exposed to any external force, or to only a force along its longitudinal central axis, the shaft 40 may retain a straight, linear position as shown.

The one or more fixation members 20 may be described as one or more "tines" having a normally curved position. The tines may be held in a distally extended position within a delivery tool. The distal tips of tines may penetrate the heart tissue to a limited depth before elastically curving back proximally into the normally curved position (shown) upon release from the delivery tool. Further, the fixation members 20 may include one or more aspects described in, for example, U.S. Pat. No. 9,675,579 (Grubac et al.), issued 13 Jun. 2017, and U.S. Pat. No. 9,119,959 (Rys et al.), issued 1 Sep. 2015, each of which is incorporated herein by reference in its entirety.

In some examples, the distal fixation and electrode assembly 36 includes a distal housing-based electrode 22. In the case of using the device 10 as a pacemaker for multiple chamber pacing (e.g., dual- or triple-chamber pacing) and sensing, the tip electrode 42 may be used as a cathode electrode paired with the proximal housing-based electrode 24 serving as a return anode electrode. Alternatively, the distal housing-based electrode 22 may serve as a return anode electrode paired with tip electrode 42 for sensing ventricular signals and delivering ventricular pacing pulses. In other examples, the distal housing-based electrode 22 may be a cathode electrode for sensing atrial signals and delivering pacing pulses to the atrial myocardium in the target implant region 4. When the distal housing-based electrode 22 serves as an atrial cathode electrode, the proximal housing-based electrode 24 may serve as the return anode paired with the tip electrode 42 for ventricular pacing and sensing and as the return anode paired with the distal housing-based electrode 22 for atrial pacing and sensing.

As shown in this illustration, the target implant region 4 in some pacing applications is along the atrial endocardium 18, generally inferior to the AV node 15 and the His bundle 5. The dart electrode assembly 12 may at least partially define the height 47, or length, of the shaft 40 for penetrating through the atrial endocardium 18 in the target implant region 4, through the central fibrous body 16, and into the ventricular myocardium 14 without perforating through the ventricular endocardial surface 17. When the height 47, or length, of the dart electrode assembly 12 is fully advanced into the target implant region 4, the tip electrode 42 may rest within the ventricular myocardium 14, and the distal housing-based electrode 22 may be positioned in intimate contact with or close proximity to the atrial endocardium 18. The dart electrode assembly 12 may have a total combined height 47, or length, of the tip electrode 42 and the shaft 40 from about 3 mm to about 8 mm in various examples. The diameter of the shaft 40 may be less than about 2 mm, and may be about 1 mm or less, or even about 0.6 mm or less.

Figure 8:
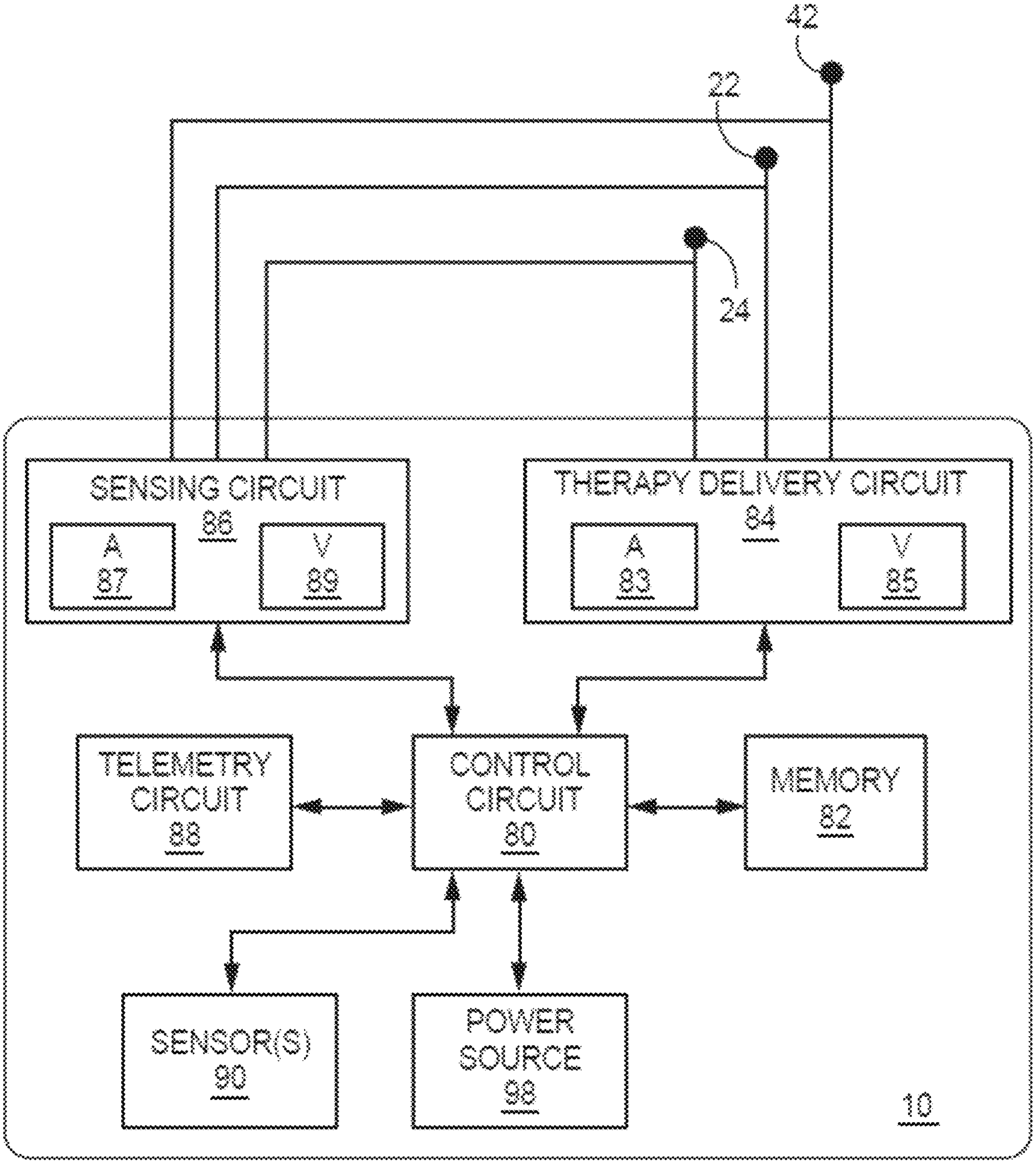
FIG. 8 is a block diagram of illustrative circuitry that may be enclosed within the housing of the medical devices of FIGS. 1-4 and FIG. 16, for example, to provide the functionality and therapy described herein.
Figure 10:
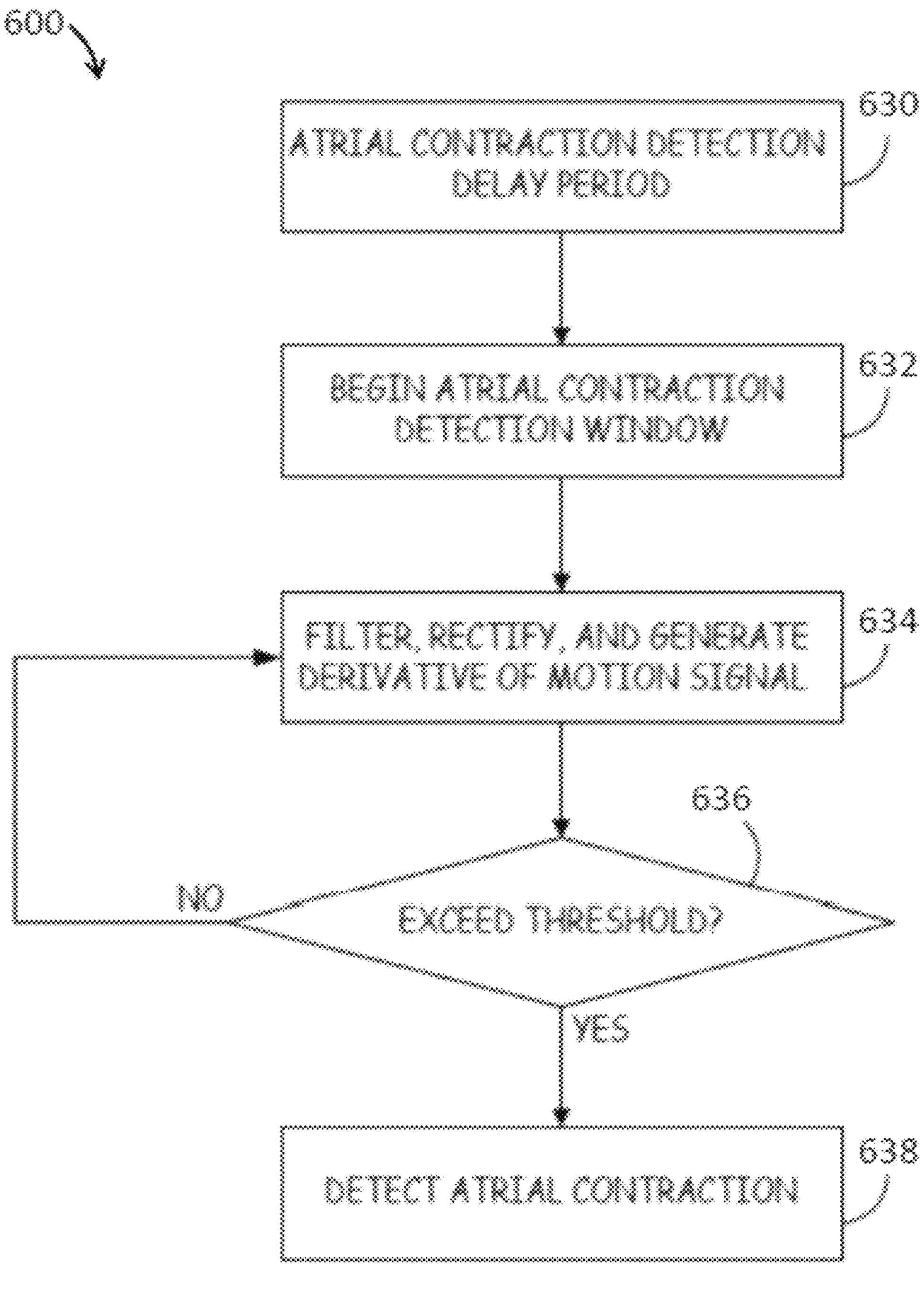
FIG. 10 is a flowchart of an illustrative method of detecting atrial activity using an atrial motion detector for use with, e.g., the illustrative systems and devices of FIGS. 1-4 and FIG. 16.
Figure 11:
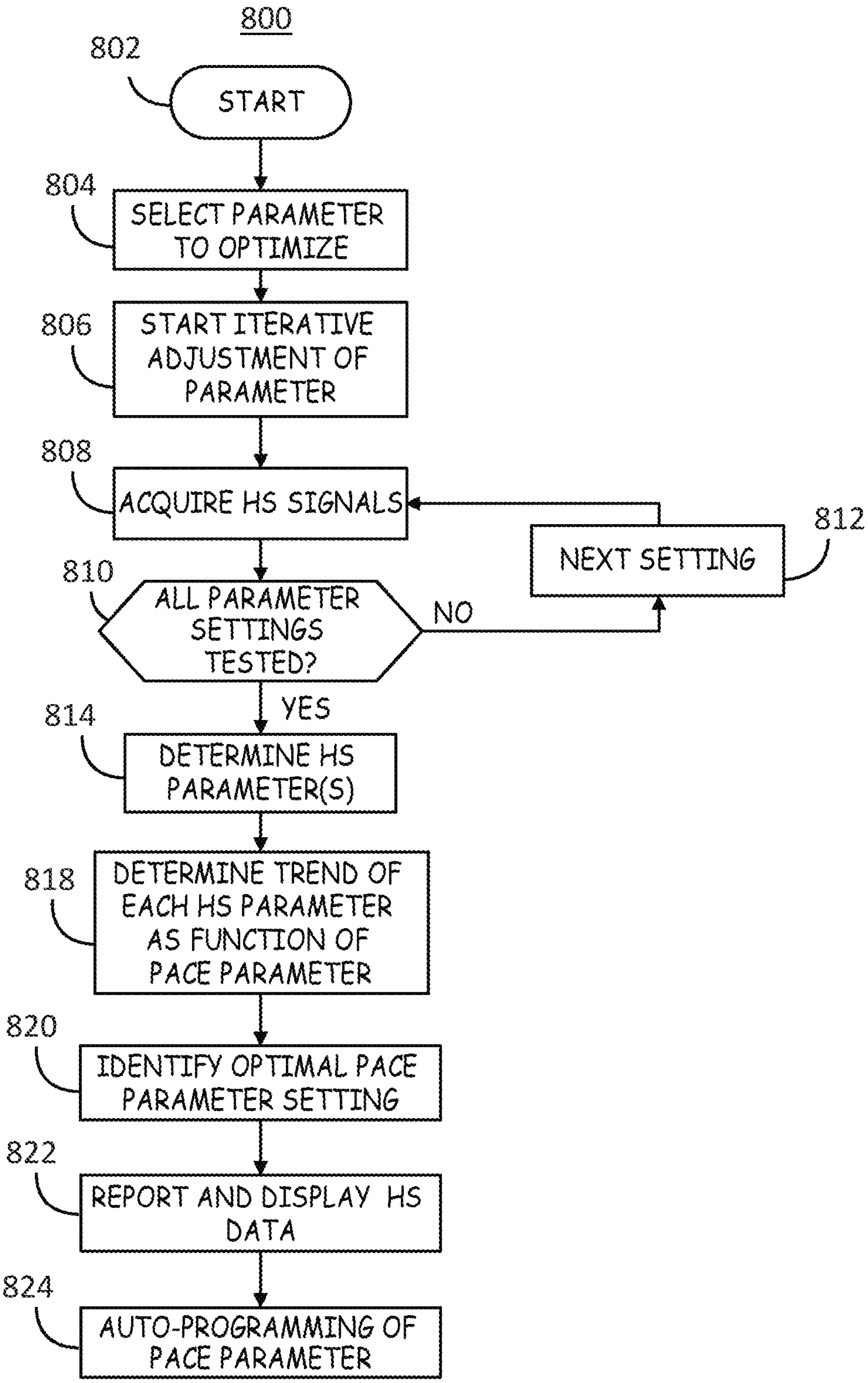
FIG. 11 is a flowchart of an illustrative method of detecting heart sounds to represent physiological response information for use with, e.g., the illustrative systems and devices of FIGS. 1-4 and FIG. 16.
Figure 12:
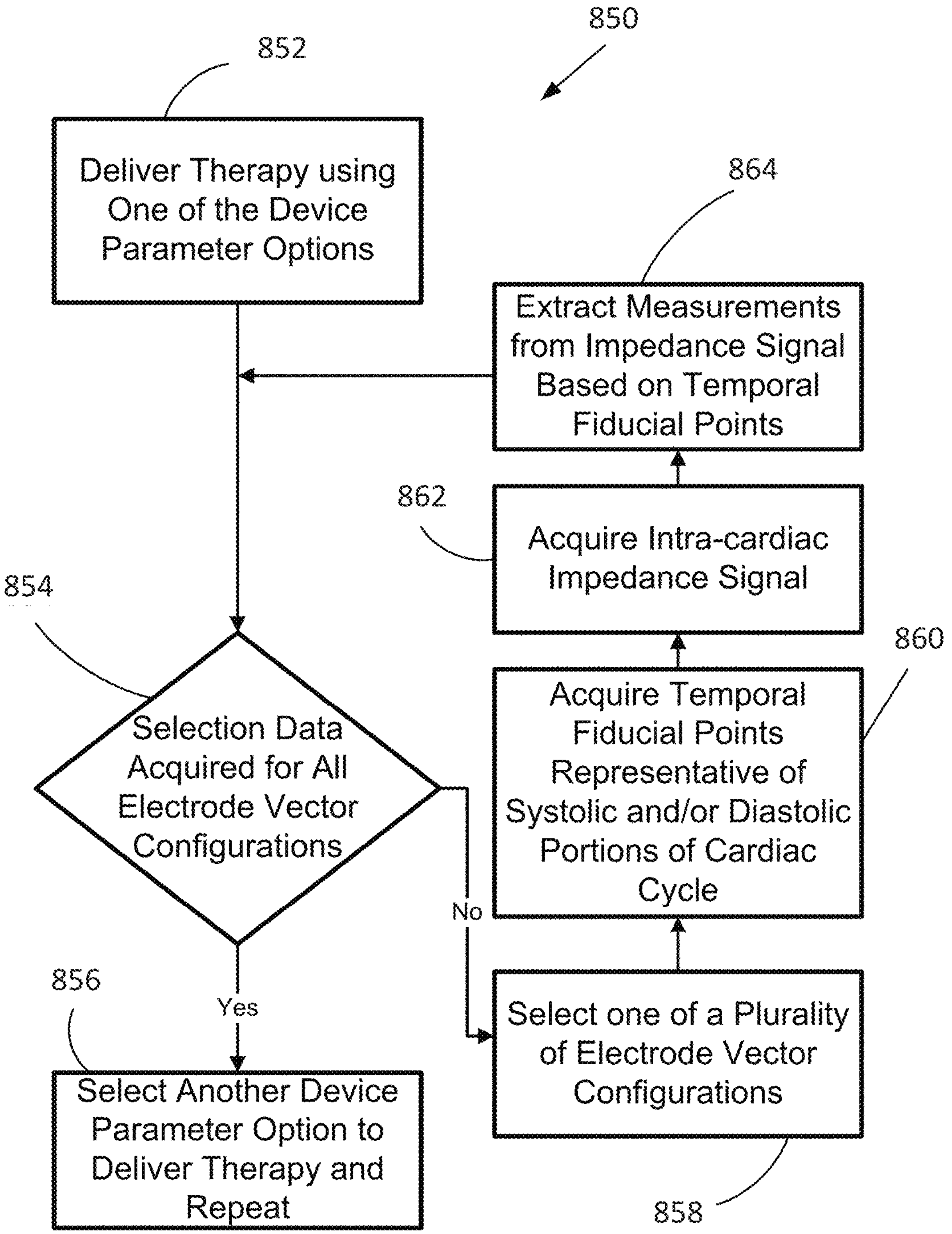
FIG. 12 is a flowchart of an illustrative method of detecting bioimpedance to represent physiological response information for use with, e.g., the illustrative systems and devices of FIGS. 1-4 and FIG. 16.

The device 10 may include an acoustic or motion detector 11 within the housing 30. The acoustic or motion detector 11 may be operably coupled to one or more a control circuit 80 (FIG. 8), a sensing circuit 86 (FIG. 8), or therapy delivery circuit 84 (FIG. 8). In some embodiments, the acoustic or motion detector 11 may be used with methods 600, 650, or 800 as shown in FIGS. 10-12. The acoustic or motion detector 11 may be used to sense mechanical activity, such as atrial mechanical activity (e.g., an atrial contraction) and/or ventricular mechanical activity (e.g., a ventricular contraction). In some embodiments, the acoustic or motion detector 11 may be used to detect right-atrial mechanical activity. A non-limiting example of an acoustic or motion detector 11 includes an accelerometer or microphone. In some embodiments, the mechanical activity detected by the acoustic or motion detector 11 may be used to supplement or replace electrical activity detected by one or more of the electrodes of the device 10. For example, the acoustic or motion detector 11 may be used in addition to, or as an alternative to, the proximal housing-based electrode 24.

The acoustic or motion detector 11 may also be used for rate response detection or to provide a rate-responsive IMD. Various techniques related to rate response may be described in U.S. Pat. No. 5,154,170 (Bennett et al.), issued Oct. 13, 1992, entitled "Optimization for rate responsive cardiac pacemaker," and U.S. Pat. No. 5,562,711 (Yerich et al.), issued Oct. 8, 1996, entitled "Method and apparatus for rate-responsive cardiac pacing," each of which is incorporated herein by reference in its entirety.

In various embodiments, acoustic or motion detector 11 (or motion sensor) may be used as an HS sensor and may be implemented as a microphone or a 1-, 2- or 3-axis accelerometer. In one embodiment, the acoustical sensor is implemented as a piezoelectric crystal mounted within an implantable medical device housing and responsive to the mechanical motion associated with heart sounds. The piezoelectric crystal may be a dedicated HS sensor or may be used for multiple functions. In the illustrative embodiment shown, the acoustical sensor is embodied as a piezoelectric crystal that is also used to generate a patient alert signal in the form of a perceptible vibration of the IMD housing. Upon detecting an alert condition, control circuit 80 may cause patient alert control circuitry to generate an alert signal by activating the piezoelectric crystal.

The control circuit may be used to control whether the piezoelectric crystal is used in a "listening mode" to sense HS signals by HS sensing circuitry or in an "output mode" to generate a patient alert. During patient alert generation, HS sensing circuitry may be temporarily decoupled from the HS sensor by control circuitry.

Examples of other embodiments of acoustical sensors that may be adapted for implementation with the techniques of the present disclosure may be described generally in U.S. Pat. No. 4,546,777 (Groch, et al.), U.S. Pat. No. 6,869,404 (Schulhauser, et al.), U.S. Pat. No. 5,554,177 (Kieval, et al.), and U.S. Pat. No. 7,035,684 (Lee, et al.), each of which is incorporated herein by reference in its entirety.

Various types of acoustical sensors may be used. The acoustical sensor may be any implantable or external sensor responsive to one or more of the heart sounds generated as described in the foregoing and thereby produces an analog electrical signal correlated in time and amplitude to the heart sounds. The analog signal may be then be processed, which may include digital conversion, by the HS sensing module to obtain HS parameters, such as amplitudes or relative time intervals, as derived by HS sensing module or control circuit 80. The acoustical sensor and HS sensing module may be incorporated in an IMD capable of delivering CRT or another cardiac therapy being optimized or may be implemented in a separate device having wired or wireless communication with IMD or an external programmer or computer used during a pace-parameter optimization procedure as described herein.

Figure 6:
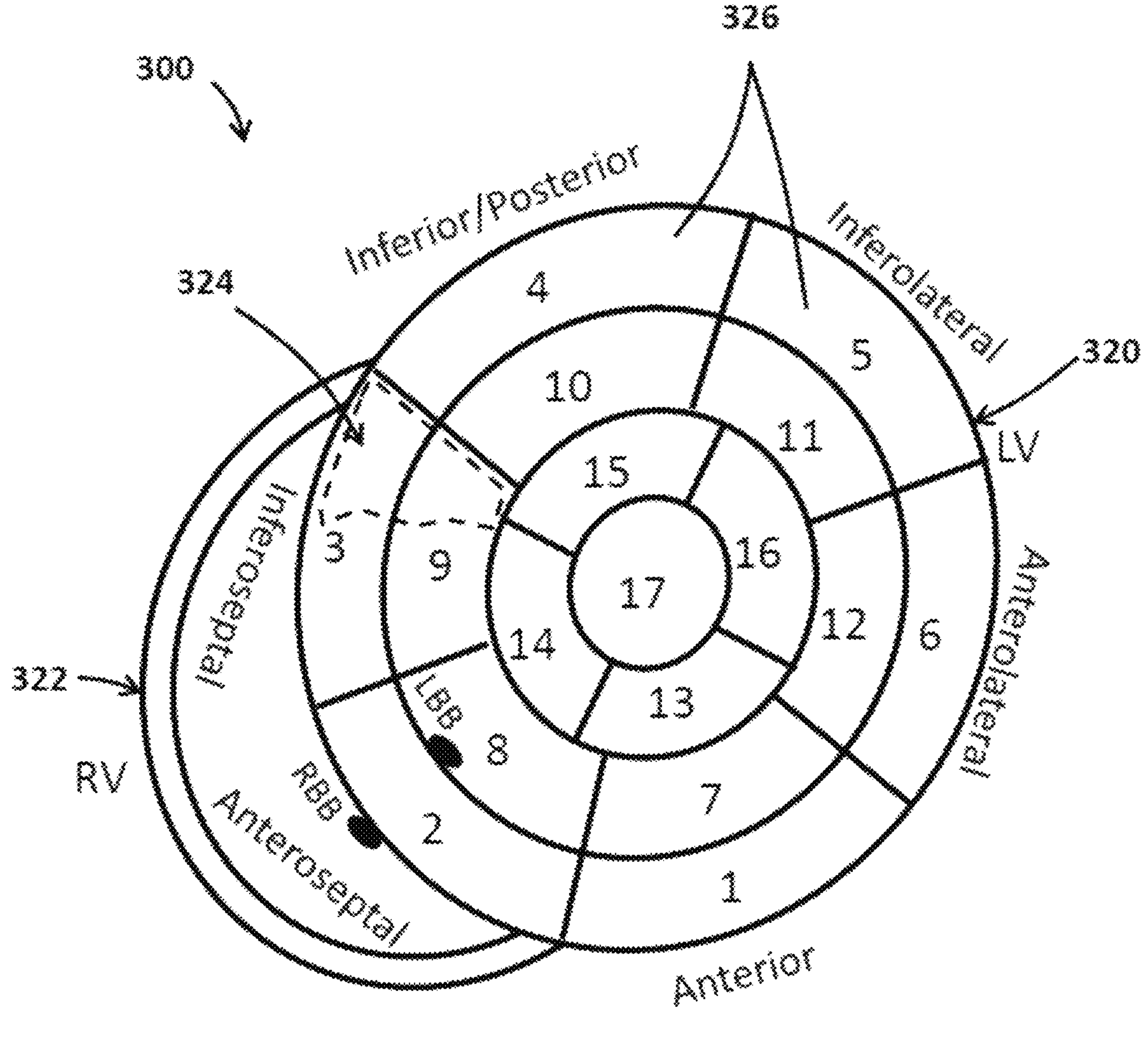
FIG. 6 is a conceptual diagram of a map of a patient's heart in a standard 17 segment view of the left ventricle showing various electrode implantation locations for use with, e.g., the illustrative systems and devices of FIGS. 1-4 and FIG. 16.

FIG. 6 is a two-dimensional (2D) ventricular map 300 of a patient's heart (e.g., a top-down view) showing the left ventricle 320 in a standard 17 segment view and the right ventricle 322. The map 300 includes a plurality of areas 326 corresponding to different regions of a human heart. As illustrated, the areas 326 are numerically labeled 1-17 (e.g., which correspond to 17 segments of the left ventricle of a human heart). Areas 326 of the map 300 may include basal anterior area 1, basal anteroseptal area 2, basal inferoseptal area 3, basal inferior area 4, basal inferolateral area 5, basal anterolateral area 6, mid-anterior area 7, mid-anteroseptal area 8, mid-inferoseptal area 9, mid-inferior area 10, mid-inferolateral area 11, mid-anterolateral area 12, apical anterior area 13, apical septal area 14, apical inferior area 15, apical lateral area 16, and apex area 17. The inferoseptal and anteroseptal areas of the right ventricle 322 are also illustrated, as well as the right bundle branch (RBB) and left bundle branch (LBB).

In some embodiments, any of the tissue-piercing electrodes of the present disclosure may be implanted in the basal region, septal region, or basal-septal region of the left ventricular myocardium of the patient's heart. In particular, the tissue-piercing electrode may be implanted from the triangle of Koch region of the right atrium through the right-atrial endocardium and central fibrous body.

Once implanted, the tissue-piercing electrode may be positioned in the target implant region 4 (FIGS. 1-5), such as the basal region, septal region, or basal-septal region of the left ventricular myocardium. With reference to map 300, the basal region includes one or more of the basal anterior area 1, basal anteroseptal area 2, basal inferoseptal area 3, basal inferior area 4, mid-anterior area 7, mid-anteroseptal area 8, mid-inferoseptal area 9, and mid-inferior area 10. With reference to map 300, the septal region includes one or more of the basal anteroseptal area 2, basal anteroseptal area 3, mid-anteroseptal area 8, mid-inferoseptal area 9, and apical septal area 14.

In some embodiments, the tissue-piercing electrode may be positioned in the basal septal region of the left ventricular myocardium when implanted. The basal septal region may include one or more of the basal anteroseptal area 2, basal inferoseptal area 3, mid-anteroseptal area 8, and mid-inferoseptal area 9.

In some embodiments, the tissue-piercing electrode may be positioned in the high inferior/posterior basal septal region of the left ventricular myocardium when implanted. The high inferior/posterior basal septal region of the left ventricular myocardium may include a portion of one or more of the basal inferoseptal area 3 and mid-inferoseptal area 9 (e.g., the basal inferoseptal area only, the mid-inferoseptal area only, or both the basal inferoseptal area and the mid-inferoseptal area). For example, the high inferior/posterior basal septal region may include region 324 illustrated generally as a dashed-line boundary. As shown, the dashed line boundary represents an approximation of where the high inferior/posterior basal septal region is located, which may take a somewhat different shape or size depending on the particular application.

Figure 7:
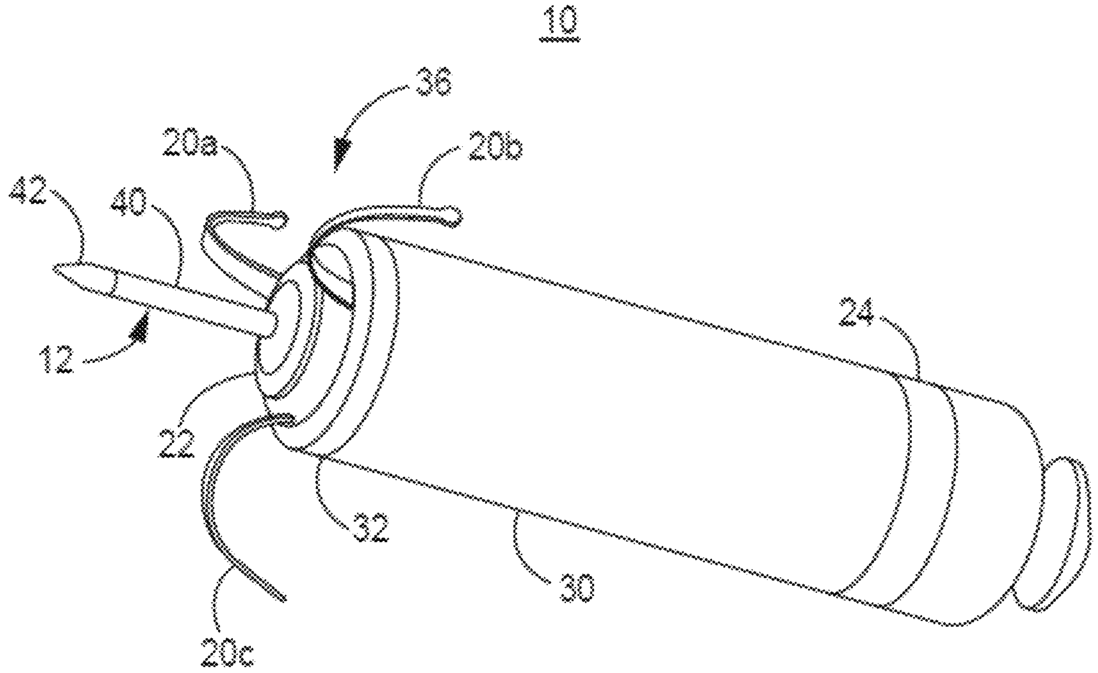
FIG. 7 is a perspective view of an intracardiac medical device having a distal fixation and electrode assembly that includes a distal housing-based electrode implemented as a ring electrode for use with, e.g., the illustrative systems and devices of FIGS. 1-4 and FIG. 16.

FIG. 7 is a three-dimensional perspective view of the device 10 capable of calibrating pacing therapy and/or delivering pacing therapy. As shown, the distal fixation and electrode assembly 36 includes the distal housing-based electrode 22 implemented as a ring electrode. The distal housing-based electrode 22 may be positioned in intimate contact with or operative proximity to atrial tissue when fixation member tines **20*a*, 20*b*, and 20*c* of the fixation members 20, engage with the atrial tissue. The tines 20*a*, 20*b*, and 20*c*, which may be elastically deformable, may be extended distally during delivery of device 10 to the implant site. For example, the tines 20*a*, 20*b*, and 20*c* may pierce the atrial endocardial surface as the device 10 is advanced out of the delivery tool and flex back into their normally curved position (as shown) when no longer constrained within the delivery tool. As the tines 20*a*, 20*b*, and 20*c* curve back into their normal position, the fixation member 20 may pull the distal fixation member and electrode assembly 36 toward the atrial endocardial surface. As the distal fixation member and electrode assembly 36 is pulled toward the atrial endocardium, the tip electrode 42 may be advanced through the atrial myocardium and the central fibrous body and into the ventricular myocardium. The distal housing-based electrode 22** may then be positioned against the atrial endocardial surface.

The distal housing-based electrode 22 may include a ring formed of an electrically conductive material, such as titanium, platinum, iridium, or alloys thereof. The distal housing-based electrode 22 may be a single, continuous ring electrode. In other examples, portions of the ring may be coated with an electrically insulating coating, e.g., parylene, polyurethane, silicone, epoxy, or another insulating coating, to reduce the electrically conductive surface area of the ring electrode. For instance, one or more sectors of the ring may be coated to separate two or more electrically conductive exposed surface areas of the distal housing-based electrode 22. Reducing the electrically conductive surface area of the distal housing-based electrode 22, e.g., by covering portions of the electrically conductive ring with an insulating coating, may increase the electrical impedance of the distal housing-based electrode 22, and thereby, reduce the current delivered during a pacing pulse that captures the myocardium, e.g., the atrial myocardial tissue. A lower current drain may conserve the power source, e.g., one or more rechargeable or non-rechargeable batteries, of the device 10.

As described above, the distal housing-based electrode 22 may be configured as an atrial cathode electrode for delivering pacing pulses to the atrial tissue at the implant site in combination with the proximal housing-based electrode 24 as the return anode. The electrodes 22 and 24 may be used to sense atrial P-waves for use in controlling atrial pacing pulses (delivered in the absence of a sensed P-wave) and for controlling atrial-synchronized ventricular pacing pulses delivered using the tip electrode 42 as a cathode and the proximal housing-based electrode 24 as the return anode. In other examples, the distal housing-based electrode 22 may be used as a return anode in conjunction with the cathode tip electrode 42 for ventricular pacing and sensing.

Figure 9:
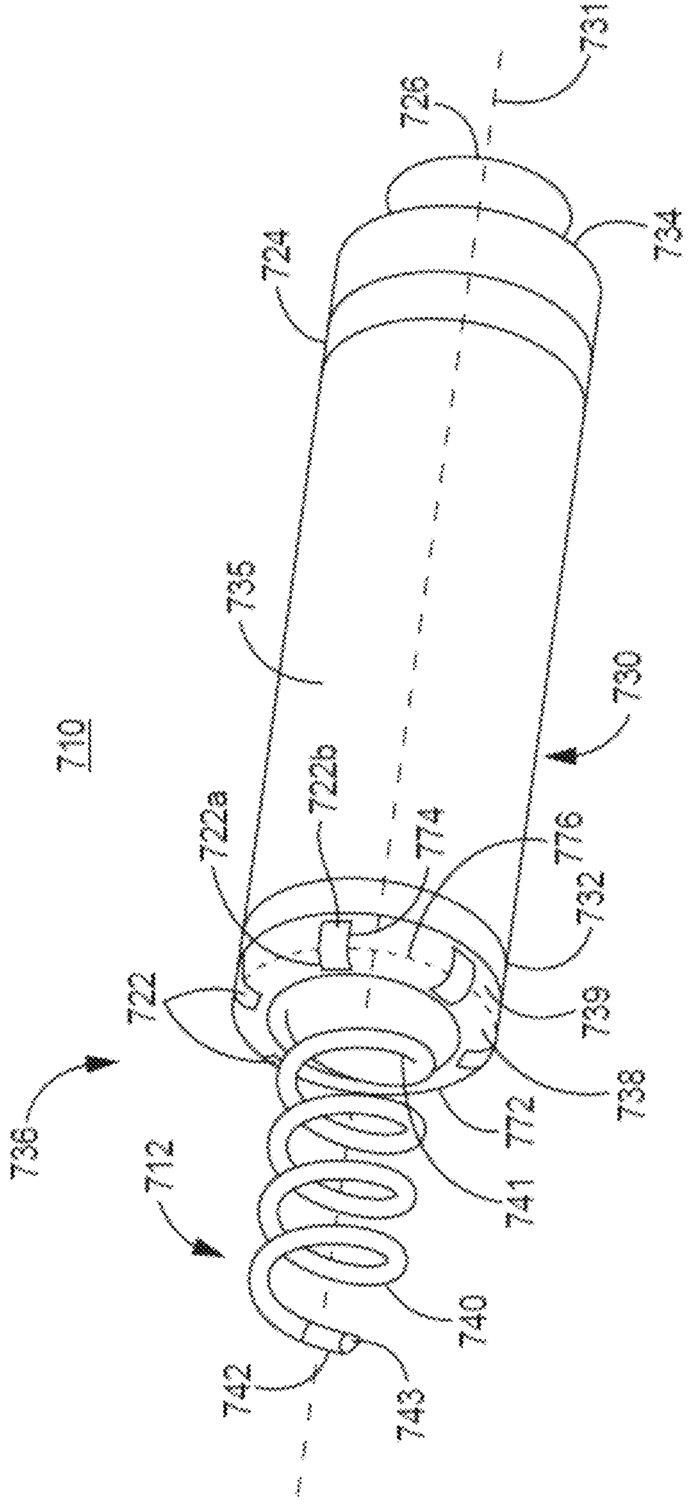
FIG. 9 is a perspective view of another illustrative intracardiac medical device for use with, e.g., the illustrative systems and devices of FIGS. 1-4 and FIG. 16.

FIG. 8 is a block diagram of circuitry that may be enclosed within the housing 30 (FIG. 7) to provide the functions of calibrating pacing therapy and/or delivering pacing therapy, using the device 10 according to one example or within the housings of any other medical devices described herein (e.g., device 408 of FIG. 2, device 418 of FIG. 3, device 428 of FIG. 4, or device 710 of FIG. 9). The separate medical device 50 (FIGS. 1-4) may include some or all the same components, which may be configured in a similar manner. The electronic circuitry enclosed within housing 30 may include software, firmware, and hardware that cooperatively acquires atrial and ventricular electrical cardiac signals, determine when a cardiac therapy is necessary, and/or deliver electrical pulses to the patient's heart according to programmed therapy mode and pulse control parameters. The electronic circuitry may include a control circuit 80 (e.g., including processing circuitry), a memory 82, a therapy delivery circuit 84, a sensing circuit 86, and/or a telemetry circuit 88. In some examples, the device 10 includes one or more sensors 90 for producing a signal that is correlated to a physiological function, state, or condition of the patient, such as a patient activity sensor, for use in determining a need for pacing therapy and/or controlling a pacing rate. For example, one sensor 90 may include an inertial measurement unit (e.g., accelerometer) to measure motion.

The power source 98 may provide power to the circuitry of the device 10 including each of the components 80, 82, 84, 86, 88, 90 as needed. The power source 98 may include one or more energy storage devices, such as one or more rechargeable or non-rechargeable batteries. The connections (not shown) between the power source 98 and each of the components, such as sensors 80, 82, 84, 86, 88, 90, may be understood from the general block diagram illustrated to one of ordinary skill in the art. For example, the power source 98 may be coupled to one or more charging circuits included in the therapy delivery circuit 84 for providing the power used to charge holding capacitors included in the therapy delivery circuit 84 that are discharged at appropriate times under the control of the control circuit 80 for delivering pacing pulses, e.g., according to a dual chamber pacing mode such as DDI(R). The power source 98 may also be coupled to components of the sensing circuit 86, such as sense amplifiers, analog-to-digital converters, switching circuitry, etc., sensors 90, the telemetry circuit 88, and the memory 82 to provide power to the various circuits.

The functional blocks shown represent functionality included in the device 10 and may include any discrete and/or integrated electronic circuit components that implement analog, and/or digital circuits capable of producing the functions attributed to the medical device 10 herein. The various components may include processing circuitry, such as an application specific integrated circuit (ASIC), an electronic circuit, a processor (shared, dedicated, or group), and memory that execute one or more software or firmware programs, a combinational logic circuit, state machine, or other suitable components or combinations of components that provide the described functionality. The particular form of software, hardware, and/or firmware employed to implement the functionality disclosed herein will be determined primarily by the particular system architecture employed in the medical device and by the particular detection and therapy delivery methodologies employed by the medical device.

The memory 82 may include any volatile, non-volatile, magnetic, or electrical non-transitory computer-readable storage media, such as random-access memory (RAM), read-only memory (ROM), non-volatile RAM (NVRAM), electrically-erasable programmable ROM (EEPROM), flash memory, or any other memory device. Furthermore, the memory 82 may include a non-transitory computer-readable media storing instructions that, when executed by one or more processing circuits, cause the control circuit 80 and/or other processing circuitry to calibrate pacing therapy and/or perform a single, dual, or triple-chamber calibrated pacing therapy (e.g., single or multiple chamber pacing), or other cardiac therapy functions (e.g., sensing or delivering therapy), attributed to the device 10. The non-transitory computer-readable media storing the instructions may include any of the media listed above.

The control circuit 80 may communicate, e.g., via a data bus, with the therapy delivery circuit 84 and the sensing circuit 86 for sensing cardiac electrical signals and controlling delivery of cardiac electrical stimulation therapies in response to sensed cardiac events, e.g., P-waves and R-waves, or the absence thereof. The tip electrode 42, the distal housing-based electrode 22, and the proximal housing-based electrode 24 may be electrically coupled to the therapy delivery circuit 84 for delivering electrical stimulation pulses to the patient's heart and to the sensing circuit 86 and for sensing cardiac electrical signals.

The sensing circuit 86 may include an atrial (A) sensing channel 87 and a ventricular (V) sensing channel 89. The distal housing-based electrode 22 and the proximal housing-based electrode 24 may be coupled to the atrial sensing channel 87 for sensing atrial signals, e.g., P-waves attendant to the depolarization of the atrial myocardium. In examples that include two or more selectable distal housing-based electrodes, the sensing circuit 86 may include switching circuitry for selectively coupling one or more of the available distal housing-based electrodes to cardiac event detection circuitry included in the atrial sensing channel 87. Switching circuitry may include a switch array, switch matrix, multiplexer, or any other type of switching device suitable to selectively couple components of the sensing circuit 86 to selected electrodes. The tip electrode 42 and the proximal housing-based electrode 24 may be coupled to the ventricular sensing channel 89 for sensing ventricular signals, e.g., R-waves attendant to the depolarization of the ventricular myocardium.

Each of the atrial sensing channel 87 and the ventricular sensing channel 89 may include cardiac event detection circuitry for detecting P-waves and R-waves, respectively, from the cardiac electrical signals received by the respective sensing channels. The cardiac event detection circuitry included in each of the channels 87 and 89 may be configured to amplify, filter, digitize, and rectify the cardiac electrical signal received from the selected electrodes to improve the signal quality for detecting cardiac electrical events. The cardiac event detection circuitry within each channel 87 and 89 may include one or more sense amplifiers, filters, rectifiers, threshold detectors, comparators, analog-to-digital converters (ADCs), timers, or other analog or digital components. A cardiac event sensing threshold, e.g., a P-wave sensing threshold and an R-wave sensing threshold, may be automatically adjusted by each respective sensing channel 87 and 89 under the control of the control circuit 80, e.g., based on timing intervals and sensing threshold values determined by the control circuit 80, stored in the memory 82, and/or controlled by hardware, firmware, and/or software of the control circuit 80 and/or the sensing circuit 86.

Upon detecting a cardiac electrical event based on a sensing threshold crossing, the sensing circuit 86 may produce a sensed event signal that is passed to the control circuit 80. For example, the atrial sensing channel 87 may produce a P-wave sensed event signal in response to a P-wave sensing threshold crossing. The ventricular sensing channel 89 may produce an R-wave sensed event signal in response to an R-wave sensing threshold crossing. The sensed event signals may be used by the control circuit 80 for setting pacing escape interval timers that control the basic time intervals used for scheduling cardiac pacing pulses. A sensed event signal may trigger or inhibit a pacing pulse depending on the particular programmed pacing mode. For example, a P-wave sensed event signal received from the atrial sensing channel 87 may cause the control circuit 80 to inhibit a scheduled atrial pacing pulse and schedule a ventricular pacing pulse at a programmed atrioventricular (AV) pacing interval. If an R-wave is sensed before the AV pacing interval expires, the ventricular pacing pulse may be inhibited. If the AV pacing interval expires before the control circuit 80 receives an R-wave sensed event signal from the ventricular sensing channel 89, the control circuit 80 may use the therapy delivery circuit 84 to deliver the scheduled ventricular pacing pulse synchronized to the sensed P-wave.

In some examples, the device 10 may be configured to deliver a variety of pacing therapies including bradycardia pacing, cardiac resynchronization therapy, post-shock pacing, and/or tachycardia-related therapy, such as ATP, among others. For example, the device 10 may be configured to detect non-sinus tachycardia and deliver ATP. The control circuit 80 may determine cardiac event time intervals, e.g., P-P intervals between consecutive P-wave sensed event signals received from the atrial sensing channel 87, R-R intervals between consecutive R-wave sensed event signals received from the ventricular sensing channel 89, and P-R and/or R-P intervals received between P-wave sensed event signals and R-wave sensed event signals. These intervals may be compared to tachycardia detection intervals for detecting non-sinus tachycardia. Tachycardia may be detected in a given heart chamber based on a threshold number of tachycardia detection intervals being detected.

The therapy delivery circuit 84 may include atrial pacing circuit 83 and ventricular pacing circuit 85. Each pacing circuit 83, 85 may include charging circuitry, one or more charge storage devices such as one or more low voltage holding capacitors, an output capacitor, and/or switching circuitry that controls when the holding capacitor(s) are charged and discharged across the output capacitor to deliver a pacing pulse to the pacing electrode vector coupled to respective pacing circuits 83, 85. The tip electrode 42 and the proximal housing-based electrode 24 may be coupled to the ventricular pacing circuit 85 as a bipolar cathode and anode pair for delivering ventricular pacing pulses, e.g., upon expiration of an AV or VV pacing interval set by the control circuit 80 for providing atrial-synchronized ventricular pacing and a basic lower ventricular pacing rate.

The atrial pacing circuit 83 may be coupled to the distal housing-based electrode 22 and the proximal housing-based electrode 24 to deliver atrial pacing pulses. The control circuit 80 may set one or more atrial pacing intervals according to a programmed lower pacing rate or a temporary lower rate set according to a rate-responsive sensor-indicated pacing rate. Atrial pacing circuit may be controlled to deliver an atrial pacing pulse if the atrial pacing interval expires before a P-wave sensed event signal is received from the atrial sensing channel 87. The control circuit 80 starts an AV pacing interval in response to a delivered atrial pacing pulse to provide synchronized multiple chamber pacing (e.g., dual- or triple-chamber pacing).

Charging of a holding capacitor of the atrial or ventricular pacing circuit 83, 85 to a programmed pacing voltage amplitude and discharging of the capacitor for a programmed pacing pulse width may be performed by the therapy delivery circuit 84 according to control signals received from the control circuit 80. For example, a pace timing circuit included in the control circuit 80 may include programmable digital counters set by a microprocessor of the control circuit 80 for controlling the basic pacing time intervals associated with various single-chamber or multiple-chamber pacing (e.g., dual- or triple-chamber pacing) modes or anti-tachycardia pacing sequences. The microprocessor of the control circuit 80 may also set the amplitude, pulse width, polarity, or other characteristics of the cardiac pacing pulses, which may be based on programmed values stored in the memory 82.

The device 10 may include other sensors 90 for sensing signals from the patient for use in determining a need for and/or controlling electrical stimulation therapies delivered by the therapy delivery circuit 84. In some examples, a sensor indicative of a need for increased cardiac output may include a patient activity sensor, such as an accelerometer. An increase in the metabolic demand of the patient due to increased activity as indicated by the patient activity sensor may be determined by the control circuit 80 for use in determining a sensor-indicated pacing rate.

Control parameters utilized by the control circuit 80 for sensing cardiac events and controlling pacing therapy delivery may be programmed into the memory 82 via the telemetry circuit 88, which may also be described as a communication interface. The telemetry circuit 88 includes a transceiver and antenna for communicating with an external device, such as a programmer or home monitor, using radio frequency communication or other communication protocols. The control circuit 80 may use the telemetry circuit 88 to receive downlink telemetry from and send uplink telemetry to the external device. In some cases, the telemetry circuit 88 may be used to transmit and receive communication signals to/from another medical device implanted in the patient.

FIG. 9 is a three-dimensional perspective view of another leadless intracardiac medical device 710 that may be configured for calibrating pacing therapy and/or delivering pacing therapy for single or multiple chamber cardiac therapy (e.g., dual- or triple-chamber cardiac therapy) according to another example. The device 710 may include a housing 730 having an outer sidewall 735, shown as a cylindrical outer sidewall, extending from a housing distal end region 732 to a housing proximal end region 734. The housing 730 may enclose electronic circuitry configured to perform single- or multiple-chamber cardiac therapy, including atrial and ventricular cardiac electrical signal sensing and pacing the atrial and ventricular chambers. The delivery tool interface member 726 is shown on the housing proximal end region 734.

A distal fixation and electrode assembly 736 may be coupled to the housing distal end region 732. The distal fixation and electrode assembly 736 may include an electrically insulative distal member 772 coupled to the housing distal end region 732. The tissue-piercing electrode assembly 712 extends away from the housing distal end region 732, and multiple non-tissue piercing electrodes 722 may be coupled directly to the insulative distal member 772. The tissue-piercing electrode assembly 712 extends in a longitudinal direction away from the housing distal end region 732 and may be coaxial with the longitudinal center axis 731 of the housing 730.

The distal tissue-piercing electrode assembly 712 may include an electrically insulated shaft 740 and a tip electrode 742 (e.g., tissue-piercing electrode). In some examples, the tissue-piercing electrode assembly 712 is an active fixation member including a helical shaft 740 and a distal cathode tip electrode 742. The helical shaft 740 may extend from a shaft distal end region 743 to a shaft proximal end region 741, which may be directly coupled to the insulative distal member 772. The helical shaft 740 may be coated with an electrically insulating material, e.g., parylene or other examples listed herein, to avoid sensing or stimulation of cardiac tissue along the shaft length. The tip electrode 742 is at the shaft distal end region 743 and may serve as a cathode electrode for delivering ventricular pacing pulses and sensing ventricular electrical signals using the proximal housing-based electrode 724 as a return anode when the tip electrode 742 is advanced into ventricular tissue. The proximal housing-based electrode 724 may be a ring electrode circumscribing the housing 730 and may be defined by an uninsulated portion of the longitudinal sidewall 735. Other portions of the housing 730 not serving as an electrode may be coated with an electrically insulating material as described above in conjunction with FIG. 7.

Using two or more tissue-piercing electrodes (e.g., of any type) penetrating into the LV myocardium may be used for more localized pacing capture and may mitigate ventricular pacing spikes affecting capturing atrial tissue. In some embodiments, multiple tissue-piercing electrodes may include two or more dart-type electrode assemblies (e.g., electrode assembly 12 of FIG. 7), a helical-type electrode (e.g., electrode assembly 712) Non-limiting examples of multiple tissue-piercing electrodes include two dart electrode assemblies, a helix electrode with a dart electrode assembly extending therethrough (e.g., through the center), or dual intertwined helixes. Multiple tissue-piercing electrodes may also be used for bipolar or multi-polar pacing.

In some embodiments, one or more tissue-piercing electrodes (e.g., of any type) that penetrate into the LV myocardium may be a multi-polar tissue-piercing electrode. A multi-polar tissue-piercing electrode may include one or more electrically active and electrically separate elements, which may enable bipolar or multi-polar pacing from one or more tissue-piercing electrodes.

Multiple non-tissue piercing electrodes 722 may be provided along a periphery of the insulative distal member 772, peripheral to the tissue-piercing electrode assembly 712. The insulative distal member 772 may define a distal-facing surface 738 of the device 710 and a circumferential surface 739 that circumscribes the device 710 adjacent to the housing longitudinal sidewall 735. Non-tissue piercing electrodes 722 may be formed of an electrically conductive material, such as titanium, platinum, iridium, or alloys thereof. In the illustrated embodiment, six non-tissue piercing electrodes 722 are spaced apart radially at equal distances along the outer periphery of insulative distal member 772. However, two or more non-tissue piercing electrodes 722 may be provided.

Non-tissue piercing electrodes 722 may be discrete components each retained within a respective recess 774 in the insulative member 772 sized and shaped to mate with the non-tissue piercing electrode 722. In other examples, the non-tissue piercing electrodes 722 may each be an uninsulated, exposed portion of a unitary member mounted within or on the insulative distal member 772. Intervening portions of the unitary member not functioning as an electrode may be insulated by the insulative distal member 772 or, if exposed to the surrounding environment, may be coated with an electrically insulating coating, e.g., parylene, polyurethane, silicone, epoxy, or another insulating coating.

When the tissue-piercing electrode assembly 712 is advanced into cardiac tissue, at least one non-tissue piercing electrode 722 may be positioned against, in intimate contact with, or in operative proximity to, a cardiac tissue surface for delivering pulses and/or sensing cardiac electrical signals produced by the patient's heart. For example, non-tissue piercing electrodes 722 may be positioned in contact with right-atrial endocardial tissue for pacing and sensing in the atrium when the tissue-piercing electrode assembly 712 is advanced into the atrial tissue and through the central fibrous body until the distal tip electrode 742 is positioned in direct contact with ventricular tissue, e.g., ventricular myocardium and/or a portion of the ventricular conduction system.

Non-tissue piercing electrodes 722 may be coupled to the therapy delivery circuit 84 and the sensing circuit 86 (see FIG. 8) enclosed by the housing 730 to function collectively as a cathode electrode for delivering atrial pacing pulses and for sensing atrial electrical signals, e.g., P-waves, in combination with the proximal housing-based electrode 724 as a return anode. Switching circuitry included in the sensing circuit 86 may be activated under the control of the control circuit 80 to couple one or more of the non-tissue piercing electrodes to the atrial sensing channel 87. Distal, non-tissue piercing electrodes 722 may be electrically isolated from each other so that each individual one of the electrodes 722 may be individually selected by switching circuitry included in the therapy delivery circuit 84 to serve alone or in a combination of two or more of the electrodes 722 as an atrial cathode electrode. Switching circuitry included in the therapy delivery circuit 84 may be activated under the control of the control circuit 80 to couple one or more of the non-tissue piercing electrodes 722 to the atrial pacing circuit 83. Two or more of the non-tissue piercing electrodes 722 may be selected at a time to operate as a multi-point atrial cathode electrode.

Certain non-tissue piercing electrodes 722 selected for atrial pacing and/or atrial sensing may be selected based on atrial capture threshold tests, electrode impedance, P-wave signal strength in the cardiac electrical signal, or other factors. For example, a single one or any combination of two or more individual non-tissue piercing electrodes 722 functioning as a cathode electrode that provides an optimal combination of a low pacing capture threshold amplitude and relatively high electrode impedance may be selected to achieve reliable atrial pacing using minimal current drain from the power source 98.

In some instances, the distal-facing surface 738 may uniformly contact the atrial endocardial surface when the tissue-piercing electrode assembly 712 anchors the housing 730 at the implant site. In that case, all the electrodes 722 may be selected together to form the atrial cathode. Alternatively, every other one of the electrodes 722 may be selected together to form a multi-point atrial cathode having a higher electrical impedance that is still uniformly distributed along the distal-facing surface 738. Alternatively, a subset of one or more electrodes 722 along one side of the insulative distal member 772 may be selected to provide pacing at a desired site that achieves the lowest pacing capture threshold due to the relative location of the electrodes 722 to the atrial tissue being paced.

In other instances, the distal-facing surface 738 may be oriented at an angle relative to the adjacent endocardial surface depending on the positioning and orientation at which the tissue-piercing electrode assembly 712 enters the cardiac tissue. In this situation, one or more of the non-tissue piercing electrodes 722 may be positioned in contact with the adjacent endocardial tissue closer than other non-tissue piercing electrodes 722, which may be angled away from the endocardial surface. By providing multiple non-tissue piercing electrodes along the periphery of the insulative distal member 772, the angle of the tissue-piercing electrode assembly 712 and the housing distal end region 732 relative to the cardiac surface, e.g., the right-atrial endocardial surface, may not be required to be substantially parallel. Anatomical and positional differences may cause the distal-facing surface 738 to be angled or oblique to the endocardial surface, however, multiple non-tissue piercing electrodes 722 distributed along the periphery of the insulative distal member 772 increase the likelihood of good contact between one or more electrodes 722 and the adjacent cardiac tissue to promote acceptable pacing thresholds and reliable cardiac event sensing using at least a subset of multiple electrodes 722. Contact or fixation circumferentially along the entire periphery of the insulative distal member 772 may not be required.

The non-tissue piercing electrodes 722 are shown to each include a first portion **722*a* extending along the distal-facing surface 738 and a second portion 722*b* extending along the circumferential surface 739. The first portion 722*a* and the second portion 722*b* may be continuous, exposed surfaces such that the active electrode surface wraps around a peripheral edge 776 of the insulative distal member 772 that joins the distal facing surface 738 and the circumferential surface 739. The non-tissue piercing electrodes 722 may include one or more of the electrodes 722 along the distal-facing surface 738, one or more electrodes along the circumferential surface 739, one or more electrodes each extending along both of the distal-facing surface 738 and the circumferential surface 739, or any combination thereof. The exposed surface of each of the non-tissue piercing electrodes 722 may be flush with respective distal-facing surfaces 738 and/or circumferential surfaces. In other examples, each of the non-tissue piercing electrodes 722 may have a raised surface that protrudes from the insulative distal member 772. Any raised surface of the electrodes 722**, however, may define a smooth or rounded, non-tissue piercing surface.

The distal fixation and electrode assembly 736 may seal the distal end region of the housing 730 and may provide a foundation on which the electrodes 722 are mounted. The electrodes 722 may be referred to as housing-based electrodes. The electrodes 722 may not be carried by a shaft or other extension that extends the active electrode portion away from the housing 730, like the distal tip electrode 742 residing at the distal tip of the helical shaft 740 extending away from the housing 730. Other examples of non-tissue piercing electrodes presented herein that are coupled to a distal-facing surface and/or a circumferential surface of an insulative distal member include the distal housing-based ring electrode 22 (FIG. 7), the distal housing-based ring electrode extending circumferentially around the assembly 36 (FIG. 7), button electrodes, other housing-based electrodes, and other circumferential ring electrodes. Any non-tissue piercing electrodes directly coupled to a distal insulative member, peripherally to a central tissue-piercing electrode, may be provided to function individually, collectively, or in any combination as a cathode electrode for delivering pacing pulses to adjacent cardiac tissue. When a ring electrode, such as the distal ring electrode 22 and/or a circumferential ring electrode, is provided, portions of the ring electrode may be electrically insulated by a coating to provide multiple distributed non-tissue piercing electrodes along the distal-facing surface and/or the circumferential surface of the insulative distal member.

The non-tissue piercing electrodes 722 and other examples listed above are expected to provide more reliable and effective atrial pacing and sensing than a tissue-piercing electrode provided along the distal fixation and electrode assembly 736. The atrial chamber walls are relatively thin compared to ventricular chamber walls. A tissue-piercing atrial cathode electrode may extend too deep within the atrial tissue leading to inadvertent sustained or intermittent capture of ventricular tissue. A tissue-piercing atrial cathode electrode may lead to interference with sensing atrial signals due to ventricular signals having a larger signal strength in the cardiac electrical signal received via tissue-piercing atrial cathode electrodes that are closer in physical proximity to the ventricular tissue. The tissue-piercing electrode assembly 712 may be securely anchored into ventricular tissue for stabilizing the implant position of the device 710 and providing reasonable certainty that the tip electrode 742 is sensing and pacing in ventricular tissue while the non-tissue piercing electrodes 722 are reliably pacing and sensing in the atrium. When the device 710 is implanted in the target implant region 4, e.g., as shown in FIG. 1 the ventricular septum, the tip electrode 742 may reach left ventricular tissue for pacing of the left ventricle while the non-tissue piercing electrodes 722 provide pacing and sensing in the right atrium. The tissue-piercing electrode assembly 712 may be in the range of about 4 to about 8 mm in length from the distal-facing surface 738 to reach left ventricular tissue. In some instances, the device 710 may achieve four-chamber pacing by delivering atrial pacing pulses from the atrial pacing circuit 83 via the non-tissue piercing electrodes 722 in the target implant region 4 to achieve bi-atrial (right and left atrial) capture and by delivering ventricular pacing pulses from the ventricular pacing circuit 85 via the tip electrode 742 advanced into ventricular tissue from the target implant region 4 to achieve biventricular (right and left ventricular) capture.

FIG. 10 shows an illustrative method 600 of detecting atrial activity, for example, using the acoustic or motion detector 11 of FIG. 5, which may be used to represent physiological response information. In particular, method 600 may include detecting an atrial contraction based on analysis of a motion signal (e.g., provided by the motion detector 11) that may be performed by an IMD implanted in the patient's heart. In some embodiments, the motion signal may be provided by an IMD implanted within a ventricle, such as the right ventricle, of the patient's heart. The method 600 may include beginning an atrial contraction detection delay period upon identification of a ventricular activation event 630. The method 600 may include beginning an atrial contraction detection window upon expiration of the atrial contraction delay period 632. The method 600 may include analyzing the motion signal within the atrial contraction detection window.

The method 600 may include filtering the motion signal within the atrial contraction detection window, rectifying the filtered signal, and generating a derivative signal of the filtered and rectified motion signal 634 within the atrial contraction detection window. The method 600 may include determining whether an amplitude of the derivative signal within the atrial contraction detection window exceeds a threshold 636. In response to determining that the amplitude of the derivative signal within the atrial contraction detection window exceeds the threshold (YES of 636), the method 600 may proceed to detecting atrial contraction 638. Otherwise (NO of 636), the method 600 may return to filtering, rectifying, and generating a derivative signal 634. Various techniques for using a motion detector that provides a motion signal may be described in U.S. Pat. No. 9,399,140 (Cho et al.), issued Jul. 26, 2016, entitled "Atrial contraction detection by a ventricular leadless pacing device for atrio-synchronous ventricular pacing," which is incorporated herein by reference in its entirety.

As will be described with respect to FIG. 11, heart sounds (HS) may be detected and used to represent physiological response information. described herein, the amplitudes and/or relative time intervals of one or more of the S1 through S4 heart sounds can be useful in optimizing a patient's hemodynamic response to CRT or other cardiac therapies that include cardiac pacing and/or neural stimulation for achieving hemodynamic benefit. The first heart sound, S1, corresponds to the start of ventricular systole. Ventricular systole begins when an action potential conducts through the atrioventricular node (AV node) and quickly depolarizes the ventricular myocardium. This event is distinguished by the QRS complex on the ECG. As the ventricles contract, the pressure in the ventricles begins to rise, causing abrupt closure of the mitral and tricuspid valves between the ventricles and atria as ventricular pressure exceeds atrial pressure. This valve closure may generate S1. S1 generally has a duration of about 150 ms and a frequency on the order of about 20 to 250 Hz. The amplitude of S1 may provide a surrogate measurement of LV contractility. Thus, an increase in S1 amplitude positively may correlate with an improvement in LV contractility. Other measures, like the pre-ejection period measured from the onset of QRS to S1, may also be used as a surrogate of myocardial contractility index.

Separation of the closure of the mitral and tricuspid valves due to ventricular dyssynchrony can be observed as separate M1 and T1 peaks in the S1 signal. Merging of the M1 (mitral valve closure sound) and the T1 (tricuspid valve closure sound) can be used as an indication of improved ventricular synchrony.

Generally, left ventricular pressure (LVP) rises dramatically following the QRS complex of the ECG and closure of the mitral valve and continues to build during ventricular systole until the aortic and pulmonary valves open, ejecting blood into the aorta and pulmonary artery. Ventricular contraction typically continues to cause blood pressure to rise in the ventricles and the aorta and pulmonary artery during the ejection phase. As the contraction diminishes, blood pressure decreases until the aortic and pulmonary valves close.

The second heart sound, S2, may be generated by the closure of the aortic and pulmonary valves, near the end of ventricular systole and start of ventricular diastole. S2 may, therefore, be correlated to diastolic pressure in the aorta and the pulmonary artery. S2 generally has a duration of about 120 ms and a frequency on the order of 25 to 350 Hz. The time interval between S1 and S2, i.e., S1-S2 time interval may represent the systolic time interval (STI) corresponding to the ventricular isovolumic contraction (pre-ejection) and ejection phase of the cardiac cycle. This S1-S2 time interval may provide a surrogate measurement for stroke volume. Furthermore, the ratio of the pre-ejection period (Q-S1) to S1-S2 time may be used as an index of myocardial contractility.

The third heart sound, S3, is associated with early, passive diastolic filling of the ventricles, and the fourth heart sound, S4, may be associated with late, active filling of the ventricles due to atrial contraction. The third sound is generally difficult to hear in a normal patient using a stethoscope, and the fourth sound is generally not heard in a normal patient. Presence of the third and fourth heart sounds during an examination using a stethoscope may indicate a pathological condition. The S3 and S4 heart sounds may be used in optimizing pace parameters as they relate to the diastolic function of the heart. Generally, these sounds would be minimized or disappear when an optimal pace parameter is identified. Other aspects of the S1 through S4 heart sounds and timing thereof that may be useful in cardiac pace-parameter optimization as known to one having ordinary skill in the art.

FIG. 11 is a flowchart 800 of a method for using heart sounds to optimize pace control parameters according to one embodiment. Methods of the present disclosure may include one or more blocks shown in flowchart 800. Other examples of using heart sounds to optimize cardiac therapy are described generally in U.S. Pat. No. 9,643,0134, granted May 9, 2017, entitled "System and method for pacing parameter optimization using heart sounds," which is incorporated herein by reference in its entirety.

A pace-parameter optimization method may be initiated at block 802. The optimization process may be initiated in response to a user command received via an external programmer. At a time of initial IMD implantation or during office follow-up visits, or during a remote patient monitoring session, a user may initiate an HS-base optimization procedure using an external programmer or networked computer. Additionally, or alternatively, the process shown by flowchart 800 may be an automated process started periodically or in response to sensing a need for therapy delivery or therapy adjustment based on a sensed physiological signal, which may include sensed HS signals.

At block 804 a pace control parameter to be optimized is selected. A control parameter may be a timing-related parameter, such as an AV interval or VV interval. Pacing vector is another control parameter that may be selected at block 804 for optimization. For example, when a multi-polar lead is used, such as a coronary sinus lead, multiple bipolar or unipolar pacing vectors may be selected for pacing in a given heart chamber. The pacing site associated with a particular pacing vector may have a significant effect on the hemodynamic benefit of pacing therapy. As such, pacing vector is one pace control parameter that may be optimized using methods described herein.

A pacing sequence is initiated at block 806 using an initial parameter setting for the test parameter selected at block 804. In one embodiment, the AV interval is being optimized, and ventricular pacing is delivered at an initial AV interval setting. It is understood that an initial AV interval setting may be selected at block 806 by first measuring an intrinsic AV interval in a patient having intact AV conduction, i.e., no AV block. An initial AV interval may be a default pacing interval, the last programmed AV interval, or a minimum or maximum AV interval to be tested. Alternatively, if the VV interval is selected for optimization, an intrinsic inter-ventricular conduction time may be measured first and paced VV intervals may be iteratively adjusted beginning at a VV interval longer, shorter, or approximately equal to the intrinsic VV conduction time.

An iterative process for adjusting the selected test parameter to at least two different settings is performed. The parameter may be adjusted to different settings in any desired order, e.g., increasing, decreasing, random, etc. For example, during adjustment of AV interval, an initial AV interval may be set to just longer than or approximately equal to a measured intrinsic AV conduction time then iteratively decreased down to a minimum AV interval test setting. During pacing using each pace parameter setting, HS signals are acquired at block 808. The iterative process advances to the next test parameter setting at block 812 until all test parameter settings have been applied, as determined at block 810, and HS signals have been recorded for each setting.

HS signals may be acquired for multiple cardiac cycles to enable ensemble averaging or averaging of HS parameter measurements taken from individual cardiac cycles. It is understood that amplification, filtering, rectification, noise cancellation techniques or other signal processing steps may be used for improving the signal-to-noise ratio of the HS signals and these steps may be different for each of the heart sounds being acquired, which may include any or all types of heart sounds.

At least one HS parameter measurement is determined from the recorded HS signals for each test parameter setting at block 814. The IMD processor or an external processor, e.g., included in a programmer, or a combination of both may perform the HS signal analysis described herein. In one embodiment, S1 and S2 are recorded and HS parameters are measured using the S1 and S2 signals at block 814. For example, the amplitude of S1, the V-S2 interval (where the V event may be a V pace or a sensed R-wave), and the S1-S2 interval are measured. The presence of S3 and/or S4 may additionally be noted, or measurements of these signals may be made for determining related parameters. HS signal parameters are determined for at least two different test parameter settings, e.g., at least two different AV intervals, two or more different VV intervals, or two or more different pacing vectors.

At block 818, a trend for each HS parameter determined at block 810 as a function of the pace parameter test settings is determined. In one embodiment, a trend for each of the V-S2 interval, S1 amplitude, and S1-S2 interval is determined. Other embodiments may include determining separation of the M1 and T1 sounds during the S1 signal. Based on the trends of the HS parameter(s) with respect to the varied pace control parameter, an optimal pace parameter setting may be identified automatically by the processor at block 820. Additionally, or alternatively, the HS trends are reported and displayed at block 822 on an external device such as a programmer or at a remote networked computer.

If the pace parameter being tested is, for example, pacing site or pacing vector when a multipolar electrode is positioned along a heart chamber, such as a quadripolar lead along LV, a pacing site or vector may be selected based on maximizing an HS-based surrogate for ventricular contractility. In one embodiment, the amplitude of S1 is used as a surrogate for ventricular contractility, and a pacing site or vector associated with a maximum S1 is identified at block 820 as the optimal pacing vector setting.

Determining the trend of each HS parameter at block 818 may include determining whether the V-S2 interval trend presents a sudden slope change, e.g., from a substantially flat trend to a decreasing trend. An AV interval associated with a sudden change in the V-S2 interval trend may be identified as an optimal AV interval setting. The optimal AV interval may be further identified based on other HS trends, for example, a maximum S1 amplitude and/or a maximum S1-S2 interval.

In some embodiments, an automatically-identified optimal pace parameter setting may also be automatically programmed in the IMD at block 824. In other embodiments, the clinician or user reviews the reported HS data and recommended pace parameter setting(s) and may accept a recommended setting or select another setting based on the HS data.

HS sensing module, or circuitry, may be operably coupled to the control circuit 80 (FIG. 8) and be configured to receive analog signals from an HS sensor for sensing one or more of these heart sounds. For example, the HS sensing module may include one or more "channels" configured to particularly sense a specific heart sound based on frequency, duration, and timing of the heart sounds. For example, ECG/EGM sensing circuitry may be used by the control circuit 80 to set HS sensing windows used by HS sensing module for sensing the heart sounds. HS sensing module may include one or more sense amplifiers, filters, and rectifiers for optimizing a signal to noise ratio of heart sound signals. Separate and unique amplification and filtering properties may be provided for sensing each of the S1 through S4 sounds to improve signal quality as needed.

Bioimpedance, or intracardiac impedance, may be measured and used to represent physiological response information. For example, any of the IMDs described herein may measure an intracardiac impedance signal by injecting a current and measuring a voltage between electrodes of an electrode vector configuration (e.g., selected electrodes). For example, the IMD may measure an impedance signal by injecting a current (e.g., a non-pacing threshold current) between a first electrode (e.g., RV electrode) and an electrode located in the RV proximate the tricuspid valve and measuring a voltage between the first and second electrodes. Another vector that may be used is from the LV electrode to the RV electrode. One will recognize that other vector pair configurations may be used for stimulation and measurement. Impedance can be measured between any set of electrodes that encompass the tissue or cardiac chamber of interest. Thus, one can inject current and measure voltage to calculate the impedance on the same two electrodes (a bipolar configuration) or inject current and measure the voltage on two separate pairs of electrodes (e.g., one pair for current injection and one pair for voltage sense), hence, a quadripolar configuration. For a quadripolar electrode configuration, the current injection and voltage sense electrodes may be in line with each other (or closely parallel to) and the voltage sense electrodes may be within the current sense field. For example, if one injected current between the SVC coil electrode and the RV tip electrode, voltage sensing may be between the RV coil electrode and RV ring electrode. In such embodiments, a VfA lead may be used for the LV cardiac therapy or sensing. The impedance vectors can be configured to encompass a particular anatomical area of interest, such as the atrium or ventricles.

The illustrative methods and/or devices described herein may sense one or more electrode vector configurations. Further, multiple impedance vectors may be measured concurrently and/or periodically relative to another. In at least one embodiment, the illustrative methods and/or devices may use impedance waveforms to acquire selection data (e.g., to find applicable fiducial points, to allow extraction of measurements from such waveforms, etc.) for optimizing CRT.

As used herein, the term "impedance signal" is not limited to a raw impedance signal. It should be implied that raw impedance signals may be processed, normalized, and/or filtered (e.g., to remove artifacts, noise, static, electromagnetic interference (EMI), and/or extraneous signals) to provide the impedance signal. Further, the term "impedance signal" may include various mathematical derivatives thereof including real and imaginary portions of the impedance signal, a conductance signal based on the impedance (i.e., the reciprocal or inverse of impedance), etc. In other words, the term "impedance signal" may be understood to include conductance signals, i.e., signals that are the reciprocal of the impedance signal.

In one or more embodiments of the methods and/or devices described herein, various patient physiological parameters (e.g., intracardiac impedance, heart sounds, cardiac cycle intervals such as R-R interval, etc.) may be determined for use in acquiring selection data to optimize CRT (e.g., set AV and/or VV delay, optimize cardiac contractility, for example, by using and/or measuring impedance first derivative dZ/dt, select pacing site, select pacing vector, lead placement, or assess pacing capture from both the electrical and mechanical points of view (e.g., electrical capture may not mean mechanical capture, and the heart sounds and impedance may assist in assessing whether the electrical stimulus captures the heart or not by looking at the mechanical information from the heart sounds and impedance), select an effective electrode vector configuration for pacing, etc.). For example, intracardiac impedance signals between two or more electrodes may be acquired for use in providing such optimization.

FIG. 12 shows one example of a method 850 for acquiring selection data for one of the device parameter options (e.g., one of the selectable device parameters that may be used to optimize CRT, such as a potential AV delay that may be an optimal parameter). Other examples of using heart sounds to optimize cardiac therapy are described generally in U.S. Pat. No. 9,707,399, granted Jul. 18, 2017, entitled "Cardiac resynchronization therapy optimization based on intracardiac impedance and heart sounds," which is incorporated herein by reference in its entirety.

As shown, pacing therapy is delivered using one of the plurality of device options (block 852) (e.g., the plurality of device parameter options may be selected, determined and/or calculated AV delays, such as percentages of intrinsic AV delay, for example, 40% of intrinsic AV delay, 50% of intrinsic AV delay, 60% of intrinsic AV delay, 70% of intrinsic AV delay, 80% of intrinsic AV delay, etc.). For the device parameter option used to pace (block 852), selection data is acquired at each of a plurality of electrode vector configurations (e.g., intracardiac impedance is sensed over a plurality of cardiac cycles, and selection data is extracted using such impedance signal). As indicated by the decision block 854, if selection data has not been acquired from all desired electrode vector configurations, then the loop of acquiring selection data (e.g., the loop illustrated by blocks 858, 860, 862, and 864) is repeated. If selection data has been acquired from all desired electrode vector configurations, then another different device parameter option is used to deliver therapy (block 856) and the method 850 of FIG. 12 is repeated (e.g., for the different device parameter option) until selection data has been acquired for all the different device parameter options (e.g., selection data being collected at each of a plurality of electrode vector configurations for each of the different device parameter options).

As shown in the repeated loop of acquiring selection data for each of the desired electrode vector configurations (e.g., blocks 858, 860, 862, and 864), one of the plurality of electrode vector configurations is selected for use in acquiring selection data (block 858). Temporal fiducial points associated with at least a part of a systolic portion of at least one cardiac cycle and/or temporal fiducial points associated with at least a part of a diastolic portion of at least one cardiac cycle for the selected electrode vector configuration are acquired (block 860) (e.g., such as with use of heart sounds, analysis of impedance signal minimum and maximums, application of algorithms based on physiological parameters such as R-R intervals, etc.). For example, temporal fiducial points associated with the systolic and/or diastolic portions of the cardiac cycle may be acquired, temporal fiducial points associated with one or more defined segments within systolic and/or diastolic portions of the cardiac cycle may be acquired, and/or temporal fiducial points within or associated with one or more points and/or portions of a systolic and/or diastolic portion of the cardiac cycle may be acquired. Yet further, for example, temporal fiducial points associated with just the systolic portion or just the diastolic portion of the cardiac cycle may be acquired, temporal fiducial points associated with one or more defined segments within just the systolic portion or just the diastolic portion of the cardiac cycle may be acquired, and/or temporal fiducial points within or associated with one or more points and/or portions of just the systolic portion or just the diastolic portion of the cardiac cycle may be acquired. In other words, fiducial points may be acquired that are associated with either both the systolic and diastolic portions of the cardiac cycle or associated with just one of such portions of the cardiac cycle. Further, for example, such fiducial points may be representative or indicative of a measurement window and/or time period (e.g., interval, point, etc.) at or during which intracardiac impedance may be measured for use in an analysis as described herein.

In about the same timeframe (e.g., about simultaneously with the acquired fiducial points), an intracardiac impedance signal is acquired at the selected electrode vector configuration (block 862). With the acquired fiducial points and the acquired intracardiac impedance signal, measurements from the impedance signal are extracted based on the temporal fiducial points (block 864) (e.g., integral of the impedance signal in a measurement window defined between fiducial points, maximum slope of impedance signal in a measurement window defined between fiducial points, time between the fiducial points, maximum impedance at a fiducial point, etc.). One or more of such measurements may be comparable to desired values for such measurements allowing for a determination of whether the measurement may indicate that the device parameter option may be an effective device parameter for optimizing therapy (e.g., a scoring algorithm may be used to determine if a device parameter option may be an optimal parameter based on whether a plurality of such measurements meet certain criteria or thresholds).

The measurement data for each of the device parameter options (e.g., obtained such as described in FIG. 12) is determined for at least one cardiac cycle. In one or more embodiments, such measurement data is acquired for a plurality of cardiac cycles. The cardiac cycles during which measurement data is acquired may be any suitable cardiac cycle. In one or more embodiments, the selected cardiac cycles during which measurement data is acquired is based on the respiratory cycle. In at least one embodiment, the measurement data is acquired during cardiac cycles occurring at the end of a respiratory cycle (e.g., proximate the end of expiration).

Figure 13:
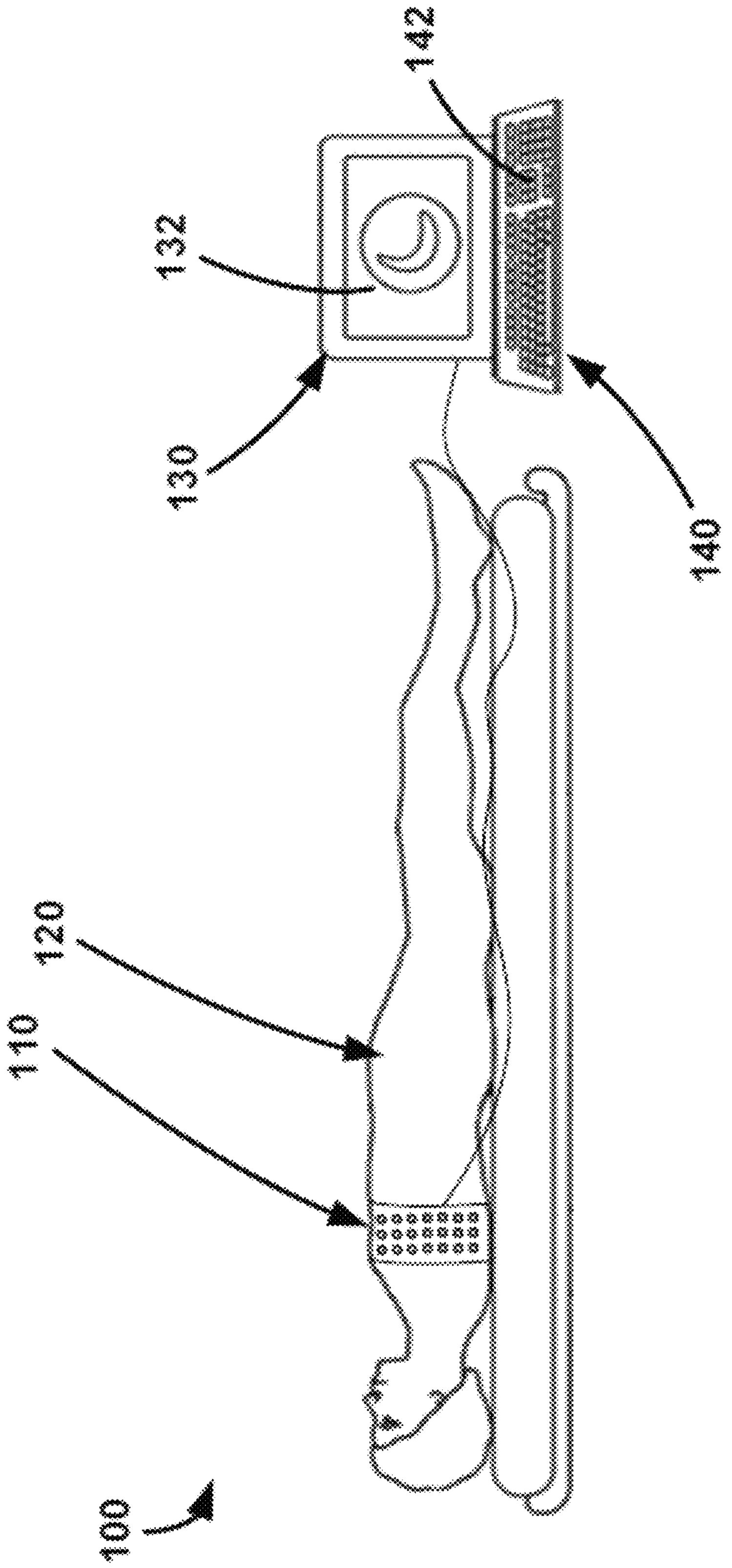
FIG. 13 is a diagram of an illustrative system including electrode apparatus, display apparatus, and computing apparatus for use with, e.g., the illustrative systems and devices of FIGS. 1-4 and FIG. 16.

FIG. 13 depicts an illustrative system 100 including electrode apparatus 110, display apparatus 130, and computing apparatus 140. The electrode apparatus 110 as shown includes a plurality of electrodes incorporated, or included, within a band wrapped around the chest, or torso, of a patient 120. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Illustrative electrode apparatus may be described in U.S. Pat. No. 9,320,446 entitled "Bioelectric Sensor Device and Methods" and issued on Apr. 26, 2016, which is incorporated herein by reference in its entirety. Further, illustrative electrode apparatus 110 will be described in more detail in reference to FIGS. 14-15.

Although not described herein, the illustrative system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the illustrative systems, methods, and interfaces described herein may further use imaging apparatus to provide noninvasive assistance to a user (e.g., a physician) to calibrate and/or deliver a VfA pacing therapy, to locate and position a device to deliver VfA cardiac pacing therapy, and/or to locate or select a pacing electrode or pacing vector proximate the patient's heart for ventricle from atrium pacing therapy in conjunction with the evaluation of ventricle from atrium pacing therapy.

For example, the illustrative systems, methods, and interfaces may provide image-guided navigation that may be used to navigate leads including leadless devices, electrodes, leadless electrodes, wireless electrodes, catheters, etc., within the patient's body while also providing noninvasive cardiac therapy evaluation including determining whether a ventricle from atrium (VfA) paced setting is optimal or determining whether one or more selected parameters are optimal, such as selected location information (e.g., location information for the electrodes to target a particular location in the left ventricle). Illustrative systems and methods that use imaging apparatus and/or electrode apparatus may be described in U.S. Patent Publication No. 2014/0371832 filed on Jun. 12, 2013, and entitled "Implantable Electrode Location Selection," U.S. Patent Publication No. 2014/0371833 filed on Jun. 12, 2013, and entitled "Implantable Electrode Location Selection," U.S. Patent Publication No. 2014/0323892 filed on Mar. 27, 2014 and entitled "Systems, Methods, and Interfaces for Identifying Effective Electrodes," U.S. Patent Publication No. 2014/0323882 filed on Mar. 27, 2014 and entitled "Systems, Methods, and Interfaces for Identifying Optical-Electrical Vectors," each of which is incorporated herein by reference in its entirety.

Illustrative imaging apparatus may be configured to acquire x-ray images and/or any other alternative imaging modality. For example, the imaging apparatus may be configured to acquire images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intravascular ultrasound (IVUS), two-dimensional (2D) ultrasound, three dimensional (3D) ultrasound, four-dimensional (4D) ultrasound, intraoperative CT, intraoperative MRI, etc. Further, it is to be understood that the imaging apparatus may be configured to acquire a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data acquired by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate treatment apparatus proximate target locations (e.g., such as locations within the left ventricle, including a selected location within the high posterior basal and/or septal area of the left ventricular cavity) within the heart or other areas of interest.

Systems and/or imaging apparatus that may be used in conjunction with the illustrative systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. App. Pub. No. 2011/0112398 to Zarkh et al. published on May 12, 2011, U.S. Pat. App. Pub. No. 2013/0116739 to Brada et al. published on May 9, 2013, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The display apparatus 130 and the computing apparatus 140 may be configured to display and analyze data such as, e.g., electrical signals (e.g., electrocardiogram data), cardiac information representative of one or more of mechanical cardiac functionality and electrical cardiac functionality (e.g., mechanical cardiac functionality only, electrical cardiac functionality only, or both mechanical cardiac functionality and electrical cardiac functionality), etc. Cardiac information may include, e.g., electrical heterogeneity information or electrical dyssynchrony information, surrogate electrical activation information or data, etc. that is generated using electrical signals gathered, sensed, or collected, using the electrode apparatus 110. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for calibrating and/or delivering pacing therapy for driving a graphical user interface configured to noninvasively assist a user in targeting placement of a pacing device, and/or for evaluating pacing therapy at that location (e.g., the location of an implantable electrode used for pacing, the location of pacing therapy delivered by a particular pacing vector, etc.).

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 and to view and/or select one or more pieces of information related to the cardiac therapy.

Although as depicted the input apparatus 142 is a keyboard, it is to be understood that the input apparatus 142 may include any apparatus capable of providing input to the computing apparatus 140 for performing the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including cardiac information, textual instructions, graphical depictions of electrical activation information, graphical depictions of anatomy of a human heart, images or graphical depictions of the patient's heart, graphical depictions of a leadless pacing device used to calibrate and/or deliver pacing therapy, graphical depictions of a leadless pacing device being positioned or placed to provide VfA pacing therapy, graphical depictions of locations of one or more electrodes, graphical depictions of a human torso, images or graphical depictions of the patient's torso, graphical depictions or actual images of implanted electrodes and/or leads, etc. Further, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, matrix mathematics, dispersion determinations (e.g., standard deviations, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more illustrative methods and/or processes described herein. Data stored and/or used by the computing apparatus 140 may include, for example, electrical signal/waveform data from the electrode apparatus 110, dispersions signals, windowed dispersions signals, parts or portions of various signals, electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

In one or more embodiments, the illustrative systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform the functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the illustrative systems, methods, and/or interfaces may be implemented using a computer readable storage medium, configured with a computer program, where the storage medium so configured causes the computer to operate in a specific and predefined manner to perform functions described herein. Further, in at least one embodiment, the illustrative systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, minicomputer, tablet computer, etc.) and may be generally described as including processing circuitry. The exact configuration of the computing apparatus 140 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable medium such as a disk or tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes, or programs (e.g., the functionality provided by such systems, processes, or programs) described herein.

Figure 14:
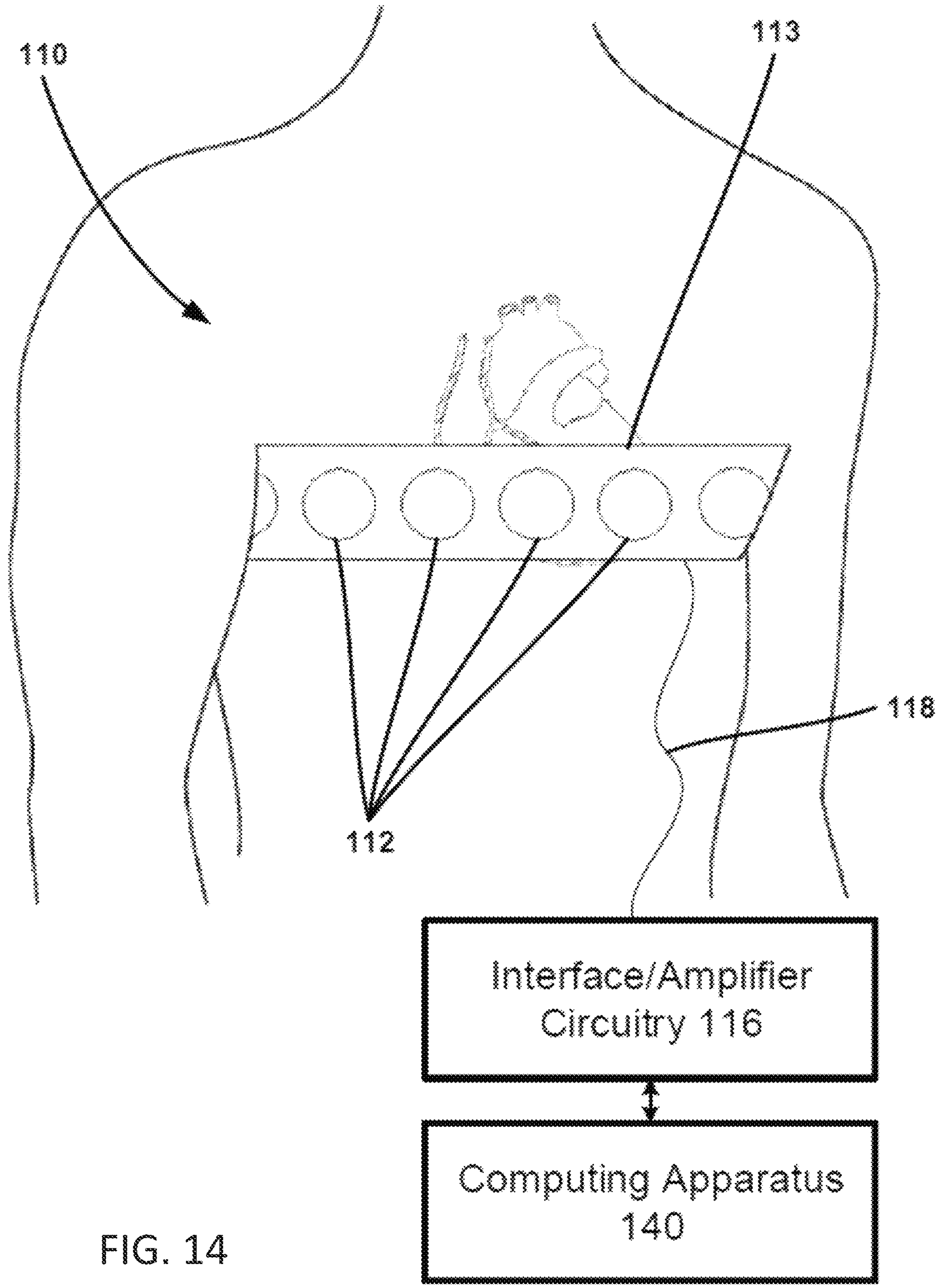
FIGS. 14-15 are diagrams of illustrative external electrode apparatus for measuring torso-surface potentials for use with, e.g., the illustrative systems and devices of FIGS. 1-4 and FIG. 16.
Figure 15:
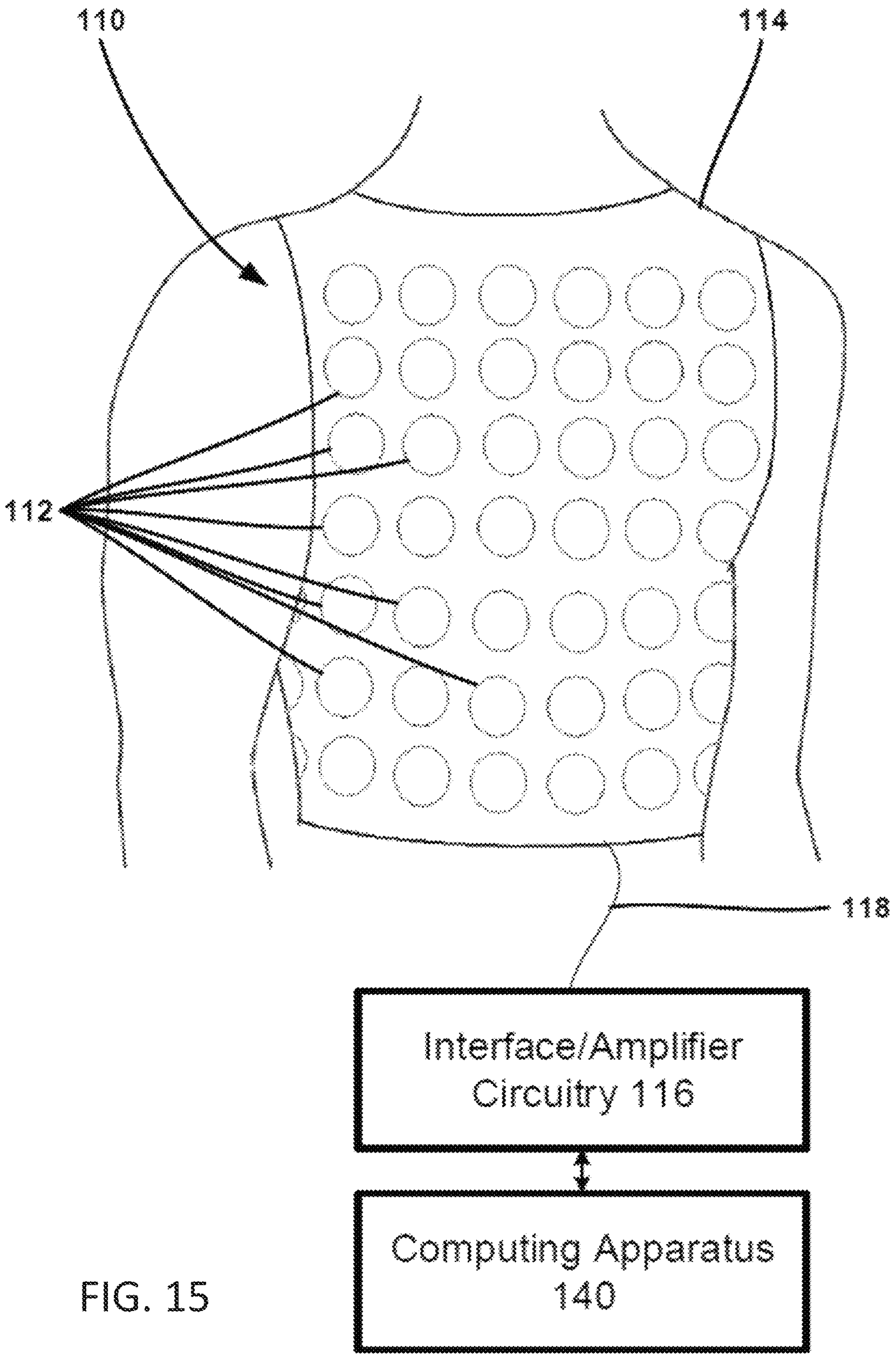

Electrical activation times of the patient's heart may be useful to evaluate a patient's cardiac condition and/or to calibrate, deliver, or evaluate ventricle from atrium (VfA) cardiac therapy to be or being delivered to a patient. Surrogate electrical activation information or data of one or more regions of a patient's heart may be sensed, or determined, using electrode apparatus 110 as shown in FIGS. 13-15. The illustrative electrode apparatus 110 may be configured to measure body-surface potentials of a patient 120 and, more particularly, torso-surface potentials of a patient 120.

As shown in FIG. 14, the illustrative electrode apparatus 110 may include a set, or array, of electrodes 112, a strap 113, and interface/amplifier circuitry 116. In at least one embodiment, a portion of the set of electrodes may be used wherein the portion corresponds to a particular location on the patient's heart. The electrodes 112 may be attached, or coupled, to the strap 113, and the strap 113 may be configured to be wrapped around the torso of a patient 120 such that the electrodes 112 surround the patient's heart. As further illustrated, the electrodes 112 may be positioned around the circumference of a patient 120, including the posterior, lateral, posterolateral, anterolateral, and anterior locations of the torso of a patient 120.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other illustrative systems may use a wireless connection to transmit the signals sensed by electrodes 112 to the interface/amplifier circuitry 116 and, in turn, the computing apparatus 140, e.g., as channels of data. For example, the interface/amplifier circuitry 116 may be electrically coupled to each of the computing apparatus 140 and the display apparatus 130 using, e.g., analog electrical connections, digital electrical connections, wireless connections, bus-based connections, network-based connections, internet-based connections, etc.

Although in the example of FIG. 14 the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 120. Further, in other examples, electrodes 112 (e.g., arranged in an array) may be part of, or located within, patches, vests, and/or other manners of securing the electrodes 112 to the torso of the patient 120.

The electrodes 112 may be configured to surround the heart of the patient 120 and record, or sens, the electrical signals associated with the depolarization and repolarization of the heart after the signals have propagated through the torso of a patient 120. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of the patient. Other configurations may have more or fewer electrodes 112.

The computing apparatus 140 may record and analyze the electrical activity (e.g., torso-surface potential signals) sensed by electrodes 112 and amplified/conditioned by the interface/amplifier circuitry 116. The computing apparatus 140 may be configured to analyze the signals from the electrodes 112 to provide as anterior and posterior electrode signals and surrogate cardiac electrical activation times, e.g., representative of actual, or local, electrical activation times of one or more regions of the patient's heart as will be further described herein. The computing apparatus 140 may be configured to analyze the signals from the electrodes 112 to provide as anterior-septal electrode signals and surrogate cardiac electrical activation times, e.g., representative of actual, or local, electrical activation times of one or more anterior-septal regions of the patient's heart, as will be further described herein, e.g., for use in calibrating, delivering, and/or evaluating VfA pacing therapy. Further, the electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. In one or more embodiments, measurement of activation times can be performed by measuring the period of time between an onset of cardiac depolarization (e.g., onset of QRS complex) and an appropriate fiducial point such as, e.g., a peak value, a minimum value, a minimum slope, a maximum slope, a zero crossing, a threshold crossing, etc.

Additionally, the computing apparatus 140 may be configured to provide graphical user interfaces depicting the surrogate electrical activation times obtained using the electrode apparatus 110. Illustrative systems, methods, and/or interfaces may noninvasively use the electrical information collected using the electrode apparatus 110 to evaluate a patient's cardiac condition and/or to calibrate, deliver, or evaluate VfA pacing therapy to be or being delivered to the patient.

FIG. 15 illustrates another illustrative electrode apparatus 110 that includes a plurality of electrodes 112 configured to surround the heart of the patient 120 and record, or sens, the electrical signals associated with the depolarization and repolarization of the heart after the signals have propagated through the torso of the patient 120. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times.

Similar to the electrode apparatus 110 of FIG. 14, the electrode apparatus 110 of FIG. 13 may include interface/amplifier circuitry 116 electrically coupled to each of the electrodes 112 through a wired connection 118 and be configured to transmit signals from the electrodes 112 to computing apparatus 140. As illustrated, the electrodes 112 may be distributed over the torso of a patient 120, including, for example, the anterior, lateral, posterolateral, anterolateral, and posterior surfaces of the torso of the patient 120.

The vest 114 may be formed of fabric with the electrodes 112 attached to the fabric. The vest 114 may be configured to maintain the position and spacing of electrodes 112 on the torso of the patient 120. Further, the vest 114 may be marked to assist in determining the location of the electrodes 112 on the surface of the torso of the patient 120. In one or more embodiments, the vest 114 may include about 17 or more anterior electrodes positionable proximate the anterior torso of the patient, and about 39 or more posterior electrodes positionable proximate the anterior torso of the patient. In some examples, there may be about 25 electrodes 112 to about 256 electrodes 112 distributed around the torso of the patient 120, though other configurations may have more or fewer electrodes 112.

As described herein, the electrode apparatus 110 may be configured to measure electrical information (e.g., electrical signals) representing different regions of a patient's heart. For example, activation times of different regions of a patient's heart can be approximated from surface electrocardiogram (ECG) activation times measured using surface electrodes in proximity to surface areas corresponding to the different regions of the patient's heart. In at least one example, activation times of the anterior-septal region of a patient's heart can be approximated from surface ECG activation times measured using surface electrodes in proximity to surface areas corresponding to the anterior-septal region of the patient's heart. That is, a portion of the set of electrodes 112, and not the entire set, can be used to generate activation times corresponding to a particular location of the patient's heart that the portion of the set of electrodes corresponds to.

The illustrative systems, methods, and interfaces may be used to provide noninvasive assistance to a user in the evaluation of a patient's cardiac health or status, and/or the evaluation of cardiac therapy such as ventricle from atrium (VfA) pacing therapy by use of the electrode apparatus 110 (e.g., cardiac therapy being presently-delivered to a patient during implantation or after implantation). Further, the illustrative systems, methods, and interfaces may be used to assist a user in the configuration, or calibration, of the cardiac therapy, such as VfA pacing therapy, to be or being delivered to a patient.

VfA pacing can be described as providing a synchronized homogeneous activation of ventricles of the heart. As an example, patients with atrial-ventricular (AV) block or prolonged AV timings that can lead to heart failure who have otherwise intact (e.g., normal) QRS can benefit from VfA pacing therapy. In addition, as an example, VfA pacing may provide beneficial activation for heart failure patients with intrinsic ventricular conduction disorders. Further, proper placement of VfA pacing can provide optimal activation of the ventricles for such patients. Further, left ventricular (LV) resynchronization for heart failure patients with left bundle branch block (LBBB) may find that VfA pacing enables easier access to left ventricular endocardium without exposing the leadless device or lead to the endocardial blood pool. At the same time, in that example, this can help engage part of the conduction system to potentially correct LBBB and effectively resynchronize the patient.

Electrical activity may be sensed using a plurality of external electrodes, such as electrodes 112 of FIGS. 13-15. The electrical activity can be sensed by a plurality of electrodes during VfA pacing therapy or in the absence of VfA pacing therapy. The sensed electrical activity can be used to evaluate VfA pacing therapy to a patient. The electrical activity sensed using the ECG belt described can be used to evaluate at least one paced setting of the VfA pacing therapy on the heart. As an example, a paced setting can be any one parameter or a combination of parameters including, but not limited to, electrode position, pacing polarity, pacing output, pacing pulse width, timing at which VfA pacing is delivered relative to atrial (A) timing, pacing rate, etc. Further, as an example, the location of the leadless device or a pacing lead can include a location in the left ventricle, accessed through the right atrium within, or in close proximity to, the high posterior basal and/or septal (HPBS) area of the left ventricular cavity. Moreover, pacing in, or in close proximity to, the HPBS area can be selective (e.g., involving stimulation of a particular area of the HPBS alone) or non-selective (e.g., combined pacing at the location of the HPBS and other atrial and/or ventricular septum areas).

Further, body-surface isochronal maps of ventricular activation can be constructed using the sensed electrical activity during VfA pacing therapy or in the absence of VfA pacing therapy. The sensed electrical activity and/or the map of ventricular activation can be used to generate electrical heterogeneity information (EHI). The electrical heterogeneity information can include determining metrics of electrical heterogeneity. The metrics of electrical heterogeneity can include a metric of standard deviation of activation times (SDAT) of electrodes on a left side of a torso of the patient and/or a metric of mean left ventricular activation time (LVAT) of electrodes on the left side of the torso of the patient. A metric of LVAT may be determined from electrodes on both the anterior and posterior surfaces, which are more proximal to the left ventricle. The metrics of electrical heterogeneity information can include a metric of mean right ventricular activation time (RVAT) of electrodes on the right side of the torso of the patient. A metric of RVAT may be determined from electrodes on both the anterior and posterior surfaces which are more proximal to the right ventricle. The metrics of electrical heterogeneity can include a metric of mean total activation time (mTAT) taken from a plurality of electrode signals from both sides of the torso of the patient, or it may include other metrics (e.g., standard deviation, interquartile deviations, a difference between a latest activation time and earliest activation time) reflecting a range or dispersion of activation times on a plurality of electrodes located on the right side of the patient torso or left side of the patient torso, or combining both right and left sides of the patient torso. The metrics of electrical heterogeneity information can include a metric of anterior-septal activation times (ASAT) of electrodes on the torso in close proximity to the anterior-septal portion of the heart.

Electrical heterogeneity information (EHI) may be generated during delivery of VfA pacing therapy at one or more VfA paced settings. The electrical heterogeneity information can be generated using metrics of electrical heterogeneity. As an example, the metrics of electrical heterogeneity can include one or more of an SDAT, an LVAT, an RVAT, an mTAT, and an ASAT. In at least one embodiment, only ASAT may be determined and further used, and/or ASAT may be more heavily weighted than other values.

One or more paced settings associated with the VfA pacing therapy may be evaluated. A paced setting can include a plurality of pacing parameters. The plurality of pacing parameters can be optimal if the patient's cardiac condition improves, if the VfA pacing therapy is effectively capturing a desired portion of the left ventricle (e.g., the high posterior basal and/or septal area), and/or if a metric of electrical heterogeneity improves by a certain threshold compared to a baseline rhythm or therapy. In at least one embodiment, the determination of whether the paced setting is optimal can be based on at least one metric of electrical heterogeneity generated from electrical activity during VfA pacing (and also, in some embodiments, during native conduction, or in the absence of VfA pacing). The at least one metric can include one or more of an SDAT, an LVAT, an RVAT, an mTAT, and an ASAT.

Further, the plurality of pacing parameters can be optimal if a metric of electrical heterogeneity is greater than or less than a particular threshold, and/or if the location of the pacing therapy to excite the left ventricle causes a particular pattern of excitation of the muscle fibers in the heart. In addition, the plurality of pacing parameters can be optimal if a metric of electrical heterogeneity indicates a correction of a left bundle branch block (LBBB), and/or if a metric of electrical heterogeneity indicates a complete engagement of a Purkinje system, etc. As an example, a metric of electrical heterogeneity of an ASAT less than or equal to a threshold (e.g., a threshold of 30 ms) and an LVAT less than or equal to a threshold (e.g., a threshold of 30 ms) can indicate a correction of an LBBB, and thus, the paced setting is optimal. As an example, a metric of electrical heterogeneity of an RVAT less than or equal to a threshold (e.g., a threshold of 30 ms), an ASAT less than or equal to a threshold (e.g., a threshold of 30 ms), and an LVAT less than or equal to a threshold (e.g., a threshold of 30 ms) can indicate a complete engagement of the Purkinje system, and thus the paced setting is may be optimal.

The paced setting can be determined to be optimal in response to the VfA pacing therapy using the paced setting being acceptable, being beneficial, being indicative of complete engagement of patient's native cardiac conduction system, being indicative of correction of a ventricular conduction disorder (e.g., left bundle branch block), etc. A paced setting can include one or more of a pacing electrode position (including one or more of a depth, an angle, an amount of turn for a screw-based fixation mechanism, etc.), a voltage, a pulse width, an intensity, a pacing polarity, a pacing vector, a pacing waveform, a timing of the pacing delivered relative to an intrinsic or paced atrial event or relative to the intrinsic His bundle potential, and/or a pacing location, etc. A pacing vector can include any two or more pacing electrodes such as, e.g., a tip electrode to a can electrode, a tip electrode to a ring electrode etc., that are used to deliver the VfA pacing therapy, etc. The pacing location can refer to the location of any of the one or more pacing electrodes that are positioned using a lead, a leadless device, and/or any device or apparatus configured to deliver VfA.

A paced setting for VfA pacing therapy may be adjusted. In at least one embodiment, the paced setting can be adjusted in response to the paced setting being not optimal. In at least one embodiment, the paced setting can be adjusted in response to the paced setting being within an optimal range but in order to determine whether the paced setting can be at a position within the optimal range that is more beneficial, more useful, more functional, etc., for the VfA pacing therapy. The paced setting could be adjusted to find the most optimal metric of electrical heterogeneity.

In one or more embodiments, a determination of whether the paced setting is optimal can be based on a particular metric of electrical heterogeneity using an ECG belt. In at least one example, the paced setting can be adjusted at intervals that correlate with a change in the metric of electrical heterogeneity until the metric of electrical heterogeneity is at or proximate a particular metric value. For instance, the adjusting of the paced setting can cause the metric of electrical heterogeneity to approach a particular threshold metric of electrical heterogeneity and, as the metric approaches the particular threshold, the rate at which the paced setting is adjusted can be slowed down. Put another way, as the metric of electrical heterogeneity is further from the particular threshold metric, the paced setting can be adjusted more quickly and as the metric of electrical heterogeneity gets closer to the particular threshold metric, the paced setting can be adjusted more slowly until the metric of electrical heterogeneity is at the particular threshold metric.

Various techniques for utilizing an electrode apparatus having a plurality of external electrodes to sense electrical activity from tissue of a patient that may be used with the devices, systems, and methods described herein are disclosed in U.S. patent application Ser. No. 15/934,517, filed 23 Mar. 2018, entitled "Evaluation of Ventricle from Atrium Pacing Therapy," which is incorporated herein by reference in its entirety.

Figure 16:
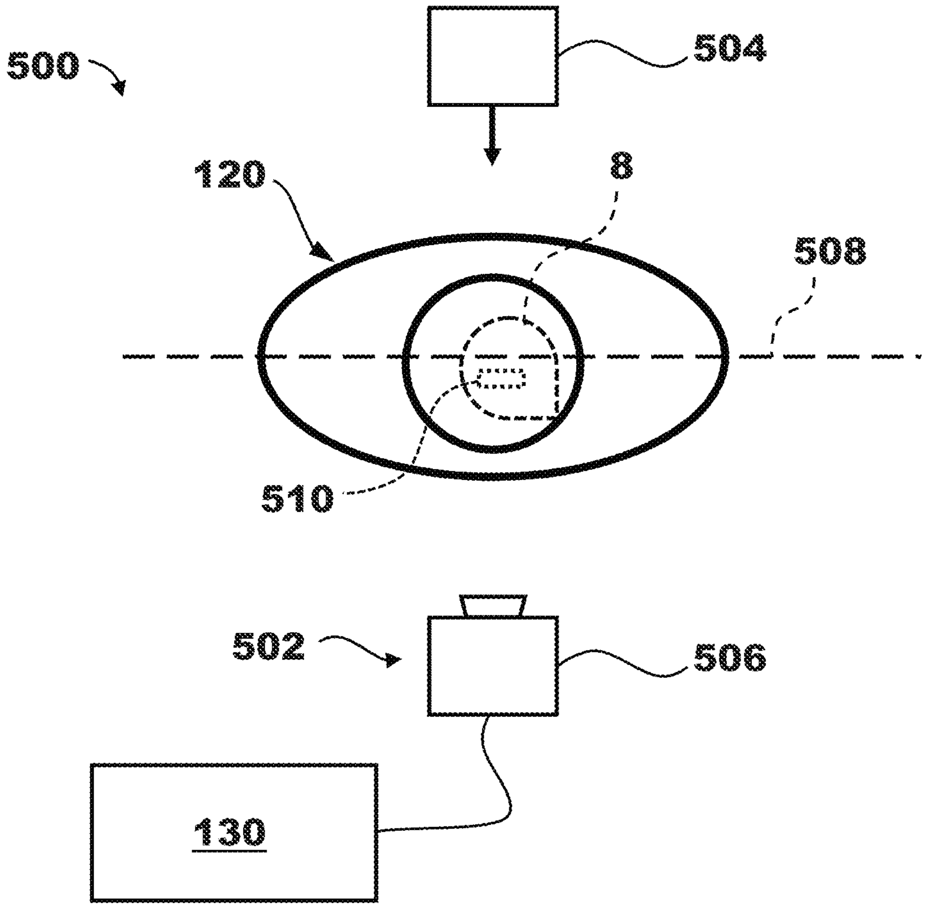
FIG. 16 is a diagram showing an overhead view of an environment including a patient and an imaging device for use with, e.g., the illustrative systems and devices of FIGS. 1-4 and the illustrative methods of FIGS. 24-25.

FIG. 16 shows an overhead view of an environment 500 including the patient 120 and an imaging device 502 having an imaging source 504 and an imaging receiver 506. In some embodiments, the imaging device 502 may be an x-ray machine having an x-ray source and an x-ray receiver. An imagable member 510 may be viewed using the imaging device 502 while being implanted in the patient's heart 8. The imaging device 502 may provide 2D imaging information, for example, aligned to a plane 508. The plane 508 may have a normal that is aligned, or parallel to, the direction of imaging between the imaging source 504 and the imaging receiver 506. Various imaging techniques and imagable members that may be used with the techniques of the present disclosure may be found, for example, in U.S. Pat. No. 10,004,467, issued Jun. 26, 2018, entitled "Guidance system for localization and cannulation of the coronary sinus," which is incorporated herein by reference in its entirety.

In some embodiments, the imagable member 510 may be part of, or include, one or more electrodes of an implantable medical device. In one example, the imagable member 510 may be part of, or include a tissue-piercing electrode implantable to deliver cardiac therapy to or sense electrical activity of the left ventricle in the basal region, septal region, or basal-septal region of the left ventricular myocardium of a patient's heart. In another example, the imagable member 510 may be part of, or include, a right atrial electrode or any other suitable electrode that is implantable in the patient's heart 8.

In some embodiments, one or more electrodes may be coupled to a housing of the implantable medical device leadlessly or using a lead. In one example, in an intracardiac device, various components may be located within an implantable housing, such as a therapy delivery circuit, a sensing circuit, and a controller, and a tissue-piercing electrode, which may be formed of an imagable material, may be leadlessly coupled to the housing. In another example, which may be an intracardiac device, various components may be located within an implantable housing, such as a therapy delivery circuit, a sensing circuit, and a controller, and a tissue-piercing electrode may be coupled to a lead that extends from the housing to a distal end region. In particular, the tissue-piercing electrode may be coupled to the distal end region of the lead. A right atrial electrode may also be coupled to the distal end region of the lead.

In general, imagable member 510 may be analyzed and used to provide additional information beyond the information shown in the image. For example, the imagable member 510 may be configured, when viewed using the imaging device 502 to provide 2D image information, to provide orientation information in a third dimension orthogonal to the two dimensions of the two-dimensional imaging (e.g., orientation information in the z-axis based on imaging information in the xy-plane). In other words, the 3D orientation information may be generated from 2D image information.

In some embodiments, the imaging device 502 may be operably coupled to a display apparatus, such as display apparatus 130, to show the imaging information to a user. In some embodiments, the imaging device 502 may be operably coupled to a computing apparatus (not shown), such as computing apparatus 140 (FIG. 13), to further process the imaging information. For example, the computing apparatus may be used to determine a 3D orientation, and a representation of the 3D orientation may be shown to the user.

FIGS. 17-23 show images of various orientations of the imagable member 510 of an implantable medical device as seen in 2D imaging information in the plane 508 (FIG. 16) from the imaging device 502 (FIG. 16). The imagable member 510 is at least partially made of an imagable material. In the illustrated embodiment, the imagable member 510 has a helical shape and a right-handed winding (e.g., going from left to right). In some embodiments, the imagable member 510 as shown may be used as a tissue-piercing electrode.

Figure 17:
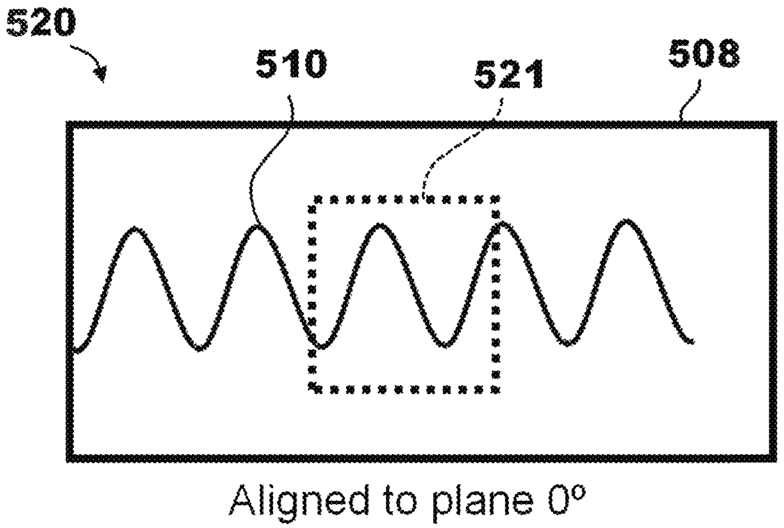
FIG. 17 is an illustration showing a two-dimensional image of an imagable material of an implantable medical device at 0 degrees relative to a plane acquired by, e.g., the illustrative imaging device of FIG. 16.

FIG. 17 shows an image 520 of the imagable member 510 at 0 degrees relative to the plane 508. In other words, the imagable member 510 is aligned to the plane 508. As can be seen in section 521 of the image 520, the imagable member 510 looks like a sine wave.

Figure 18:
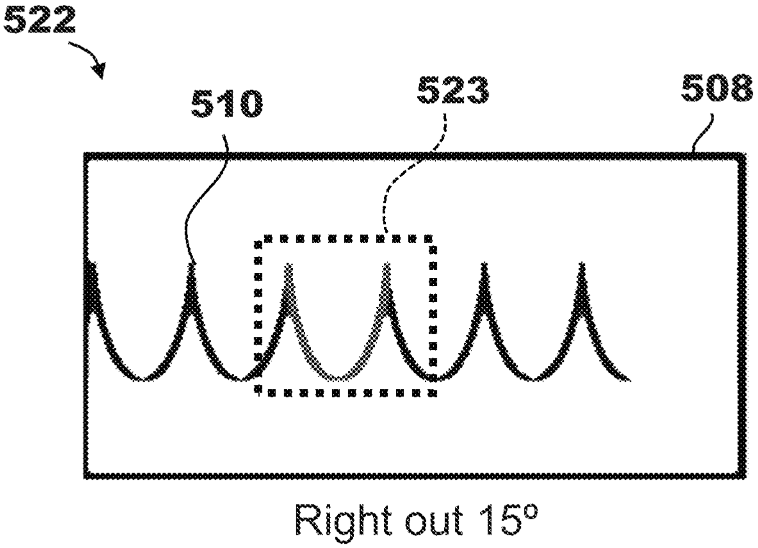
FIG. 18 is an illustration showing a two-dimensional image of the imagable material of the implantable medical device at +15 degrees relative to a plane acquired by, e.g., the illustrative imaging device of FIG. 16.

FIG. 18 shows an image 522 of the imagable member 510 at +15 degrees relative to the plane 508. In other words, the imagable member 510 is angled away from the imaging receiver of the imaging device 502. As can be seen in section 523 of the image 522, the imagable member 510 looks like a repeating U-shape.

Figure 19:
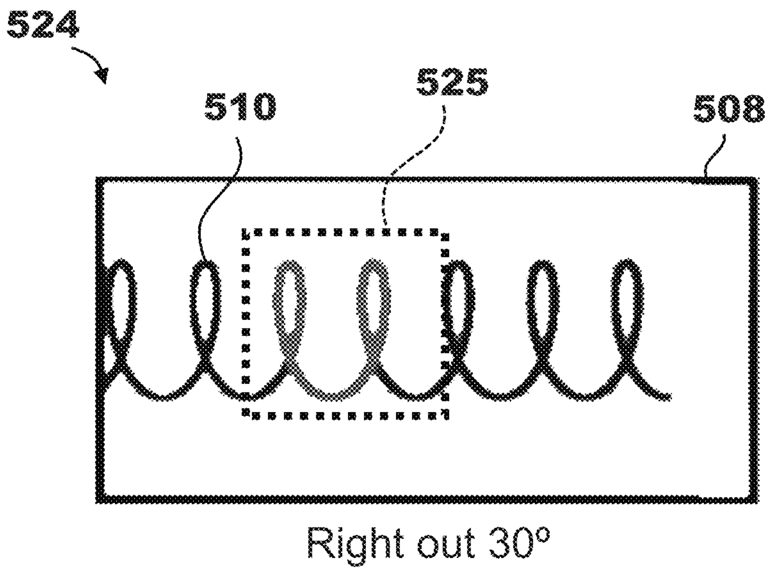
FIG. 19 is an illustration showing a two-dimensional image of the imagable material of the implantable medical device at +30 degrees relative to a plane acquired by, e.g., the illustrative imaging device of FIG. 16.

FIG. 19 shows an image 524 of the imagable member 510 at +30 degrees relative to the plane 508. In other words, the imagable member 510 is angled even further away from the imaging receiver of the imaging device 502 than shown in FIG. 18. As can be seen in section 525 of the image 524, the imagable member 510 looks like a repeating U-shape with small loops at the end, or top, of each U.

Figure 20:
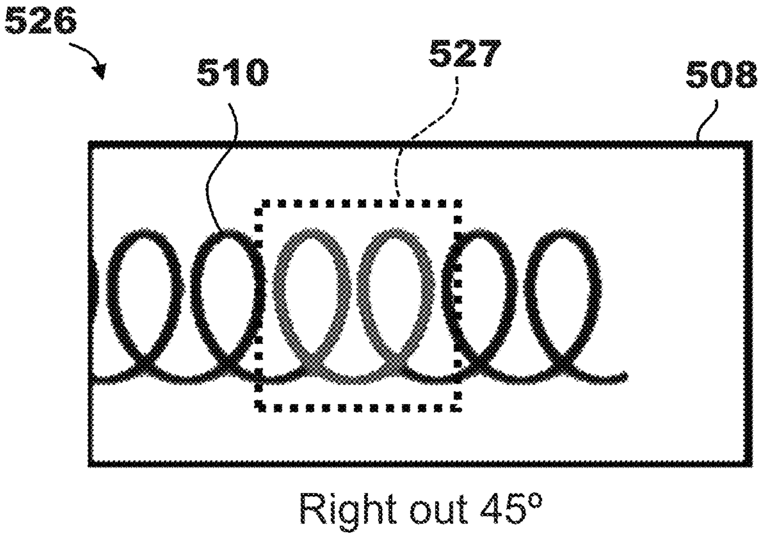
FIG. 20 is an illustration showing a two-dimensional image of the imagable material of the implantable medical device at +45 degrees relative to a plane acquired by, e.g., the illustrative imaging device of FIG. 16.

FIG. 20 shows an image 526 of the imagable member 510 at +45 degrees relative to the plane 508. In other words, the imagable member 510 is angled even further away from the imaging receiver of the imaging device 502 than shown in FIGS. 18-19. As can be seen in section 527 of the image 526, the imagable member 510 looks like a repeating U-shape with large loops at the end, or top, of each U.

Figure 21:
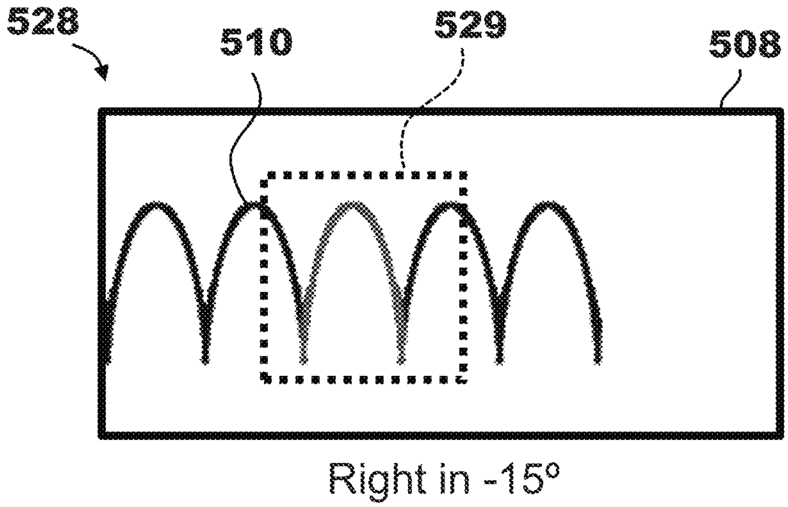
FIG. 21 is an illustration showing a two-dimensional image of the imagable material of the implantable medical device at −15 degrees relative to a plane acquired by, e.g., the illustrative imaging device of FIG. 16.

FIG. 21 shows an image 528 of the imagable member 510 at −15 degrees relative to the plane 508 (e.g., the opposite from FIG. 18). In other words, the imagable member 510 is angled toward the imaging receiver of the imaging device 502. As can be seen in section 529 of the image 528, the imagable member 510 looks like a repeating lowercase N-shape (e.g., an arch).

Figure 22:
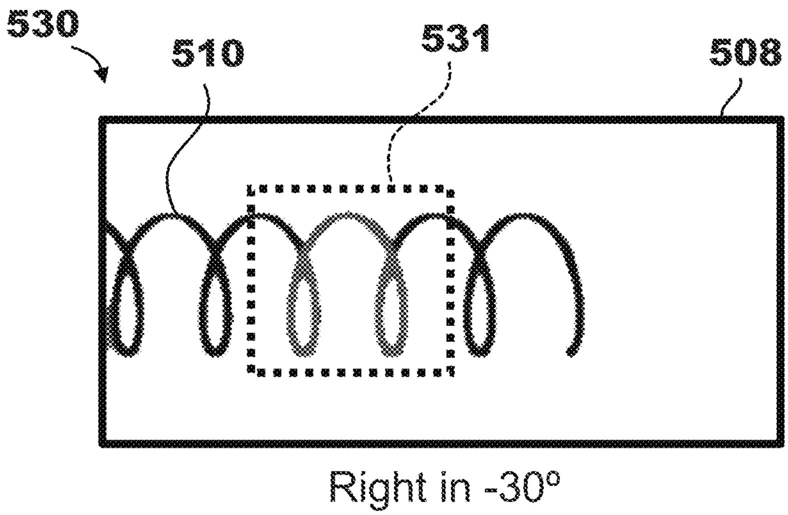
FIG. 22 is an illustration showing a two-dimensional image of the imagable material of the implantable medical device at −30 degrees relative to a plane acquired by, e.g., the illustrative imaging device of FIG. 16.

FIG. 22 shows an image 530 of the imagable member 510 at −30 degrees relative to the plane 508 (e.g., the opposite angle from FIG. 19). In other words, the imagable member 510 is angled even further toward the imaging receiver of the imaging device 502 than shown in FIG. 21. As can be seen in section 531 of the image 530, the imagable member 510 looks like a repeating lowercase N-shape with small loops at the end, or bottom, of each N.

Figure 23:
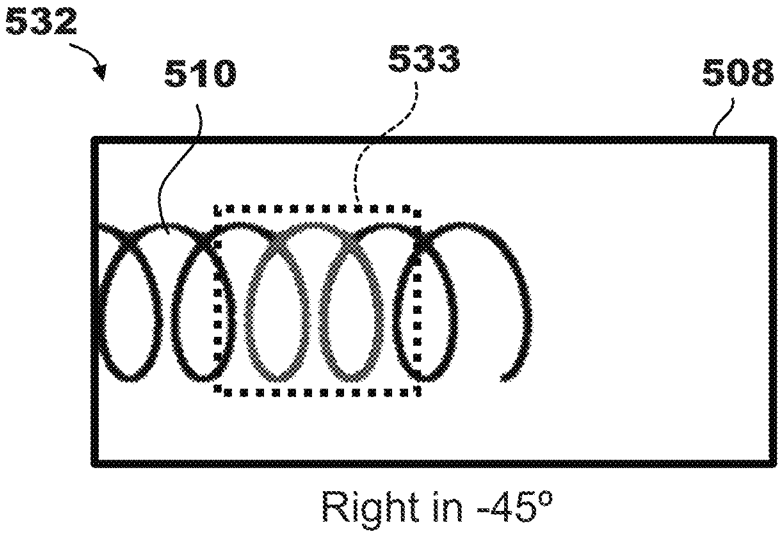
FIG. 23 is an illustration showing a two-dimensional image of the imagable material of the implantable medical device at −45 degrees relative to a plane acquired by, e.g., the illustrative imaging device of FIG. 16.

FIG. 23 shows an image 532 of the imagable member 510 at −45 degrees relative to the plane 508 (e.g., the opposite angle from FIG. 20). In other words, the imagable member 510 is angled even further toward the imaging receiver of the imaging device 502 than shown in FIGS. 21-22. As can be seen in section 533 of the image 532, the imagable member 510 looks like a repeating lowercase N-shape with large loops at the end, or top, of each N.

Knowledge of the shapes of the imagable member 510 visible in the two-dimensional imaging may be used in one or more implantable medical device delivery methods, or implantation methods.

FIG. 24 shows one example of a method 550 of delivering an implantable medical device, such as an implantable medical device described hereinabove. The method 550 may include advancing a medical device 552. For example, an implantable medical device having a tissue-piercing electrode may be advanced toward the triangle of Koch region of the right atrium through the right atrial endocardium and central fibrous body. The tissue-piercing electrode may be configured to deliver cardiac therapy to or sense electrical activity of the left ventricle in the basal region, septal region, or basal-septal region of the left ventricular myocardium of a patient's heart. In some embodiments, the tissue-piercing electrode may be formed of an imagable material. In some embodiments, the implantable medical device may include an imagable member formed of an imagable material coupled to a housing or a lead of the implantable medical device.

The method 550 may include acquiring image information 554. For example, image information may be acquired that represents the patient's heart and that represents the imagable material. The image information may be generated using two-dimensional imaging (e.g., x-ray fluoroscopy).

Further, the method 550 may include generating orientation information 556. For example, orientation information representing the implantable medical device may be generated based on the acquired image information. The orientation of the implantable medical device may be determined from the generated orientation information. In one example, processing circuitry may be used to determine the orientation of the implantable medical device based on the generated orientation information. As used herein, "orientation information" refers to any information derived from the imaging information that may be used to provide information in another dimension that is not shown in the imaging information. For example, orientation information may include the detection of the U-shape or the N-shape of the imagable member (see, e.g., FIGS. 18-23).

The method 550 may also include implanting the implantable medical device 558. In one example, the implantable medical device may be implanted in the triangle of Koch region of the right atrium of the patient's heart based on the generated orientation information representing the implantable medical device. In another example, the implantable medical device may be implanted from the coronary sinus into the myocardium adjacent to the cardiac conduction system.

FIG. 25 shows another example of a method 570 of delivering an implantable medical device. Method 570 may also include one or more of advancing the medical device 552, acquiring image information 554, generating orientation information 556, and implanting the medical device 558.

In addition, method 570 may include displaying orientation information 572. In one example, the imagable member having imagable material may be displayed on a display device (e.g., display apparatus) and show at least one of a lowercase N-shape (e.g., arch) or a U-shape viewable in the two-dimensional imaging. The lowercase N-shape or U-shape may be used to indicate whether the implantable medical device is pointed toward or away from an imaging device used to acquire the image information.

The method 570 may also include pointing the device before tissue engagement 574. In some embodiments, once the general implantation site (e.g., triangle of Koch region) has been reached a user may be instructed, or may have been instructed, to point the implantable medical device (e.g., the tissue-piercing electrode end portion) toward the apex of the patient's heart. Pointing the device in this manner may provide an optimal angle to reach the left ventricular myocardium or cardiac conduction system. In particular, the user may point the device before advancing the tissue-piercing electrode into the tissue of the patient's heart (e.g., into the right atrial endocardium and central fibrous body). A predetermined model of the patient's heart may be used to facilitate visualization and guidance to reach the general implantation site and the orientation of the implantable medical device. Any generated orientation information may also be used to facilitate visualization and guidance of the implantable medical device.

Generally, positioning of an electrode within the patient can be based upon image data acquired of the patient and user input and experience. Positioning of the electrode depend on the geometry of the chambers of the heart or vessels, tortuosity of a path through the chambers of the heart or vessels to reach a target location, the diameter of the coronary vessels, or any combination of these.

Using various systems, such as the CardioGuide™ implant system sold by Medtronic, Inc., image data can be acquired of a patient to identify various portions of the anatomy. For example, 2D image data acquired during venograms can be assimilated or reconstructed into a 2D model of the coronary vasculature of a subject, such as a human patient. The 3D image of the vasculature can include geometric, size, and configuration information regarding various portions of the anatomy, tortuosity of a path to reach a target location, vessel size to reach a coronary vessel, size of the vessel, location of the vessel, etc. In addition to the geometric shape and configuration of the patient, image data can incorporate or include physiological data, such as contraction timing, motion change, and the like. For example, image data can be acquired at a single time to generate a static three-dimensional model. Image data may also be acquired over time, such as about 30 frames per second, to acquire contraction timing data regarding a patient.

A system that can generate images of a patient, such as a vascular system of a patient, using fluoroscopic images may require the injection of a contrast agent into the vasculature of a patient. To inject a contrast agent into a vasculature of a heart of a patient, access to a coronary sinus ostium (herein CSOs) may be obtained. According to various embodiments a catheter can be positioned in or near the CSOs and a contrast agent can be injected to allow a contrast agent to flow through a vasculature around a heart. Images can be acquired of the patient, such as with a fluoroscopic system, during the flow time of the contrast agent.

Prior to the injection of a contrast agent into a patient's vascular system, fluoroscopic images (generally using x-rays) may not provide high contrast view of non-radiopaque portions. For example, non-radiopaque portions can include soft tissues of the heart. A high contrast instrument, such as a radiopaque portion of a catheter, can be viewed with a fluoroscopic imaging system.

A statistical model or model of a statistically "average subject" can be used to assist in identifying a possible or statistically probable location of the CSOs. A user, such as a surgeon, can then move the catheter towards a statistically probable location and orientation of the CSOs to assist in cannulating the CSOs and allowing injection of a contrast agent into the CSOs for flowing through the vascular system of the patient. As discussed herein, various techniques can be used to assist in cannulating the CSOs, such as real time tracking (i.e. viewing) of the relative position of an instrument and the predicted CSOs location, measurement of the instrument location and direction based on radiopaque landmarks and views of the instrument, etc.

ILLUSTRATIVE EMBODIMENTS

While the present disclosure is not so limited, an appreciation of various aspects of the disclosure of the present application will be gained through a discussion of some illustrative embodiments provided below.

In illustrative embodiment A1, an implantable medical device comprises one or more electrodes comprising a tissue-piercing electrode implantable to deliver cardiac therapy to or sense electrical activity of the left ventricle in the basal region, septal region, or basal-septal region of the left ventricular myocardium of a patient's heart, wherein the tissue-piercing electrode comprises an imagable material. The device also comprises a therapy delivery circuit operably coupled to the one or more electrodes to deliver cardiac therapy to the patient's heart; a sensing circuit operably coupled to the one or more electrodes to sense electrical activity of the patient's heart; and a controller comprising processing circuitry operably coupled to the therapy delivery circuit and the sensing circuit. The controller is configured to: sense electrical activity using one or more electrodes; and deliver cardiac therapy based on the sensed electrical activity.

In illustrative embodiment A2, a device comprises a device according to any A embodiment, wherein the imagable material comprises radiopaque properties visible using fluoroscopy.

In illustrative embodiment A3, a device comprises a device according to any A embodiment, wherein the tissue-piercing electrode is implantable from the triangle of Koch region of the right atrium through the right atrial endocardium and central fibrous body to deliver cardiac therapy to or sense electrical activity of the left ventricle in the basal region, septal region, or basal-septal region of the left ventricular myocardium of the patient's heart.

In illustrative embodiment A4, a device comprises a device according to any A embodiment, wherein the one or more electrodes comprise a right atrial electrode positionable within the right atrium to deliver cardiac therapy to or sense electrical activity of the right atrium of the patient's heart.

In illustrative embodiment A5, a device comprises a device according to any A embodiment, wherein the tissue-piercing electrode is configured, when viewed using two-dimensional imaging, to provide orientation information in a third dimension orthogonal to the two dimensions of the two-dimensional imaging.

In illustrative embodiment A6, a device comprises a device according to any A embodiment, wherein the tissue-piercing electrode has a helical shape.

In illustrative embodiment A7, a device comprises a device according to any A embodiment, further comprising a housing, wherein the therapy delivery circuit, the sensing circuit, and the controller are located within the housing and the tissue-piercing electrode is leadlessly coupled to the housing.

In illustrative embodiment A8, a device comprises a device according to any embodiment A1-A6, further comprising: a housing, wherein the therapy delivery circuit, the sensing circuit, and the controller are located within the housing; and a lead coupled to and extending from the housing to a distal end region, wherein the tissue-piercing electrode and a right atrial electrode are coupled to the distal end region of the lead.

In illustrative embodiment A9, a device comprises a device according to any embodiment A1-A6, further comprising: a housing, wherein the therapy delivery circuit, the sensing circuit, and the controller are located within the housing; a first lead coupled to and extending from the housing to a first distal end region, wherein the tissue-piercing electrode is coupled to the first distal end region of the first lead; and a second lead coupled to and extending from the housing to a second distal end region, wherein a right atrial electrode is coupled to the second distal end region of the second lead.

In illustrative embodiment A10, a device comprises a device comprises a device according to any embodiment A1-A6, further comprising: a housing, wherein the therapy delivery circuit, the sensing circuit, and the controller are located within the housing; a first lead coupled to and extending from the housing to a first distal end region wherein the tissue-piercing electrode is coupled to the first distal end region of the first lead; a second lead coupled to and extending from the housing to a second distal end region, wherein a right atrial electrode is coupled to the second distal end region of the second lead; and a third lead coupled to and extending from the housing to a third distal end region, wherein the one or more electrodes further comprise a right ventricular electrode to deliver cardiac therapy to or sense electrical activity of the right ventricle of the patient's heart coupled to the third distal end region of the third lead.

In illustrative embodiment B1, an implantable medical device comprises one or more electrodes comprising a tissue-piercing electrode implantable to deliver cardiac therapy to or sense electrical activity of the left ventricle in the basal region, septal region, or basal-septal region of the left ventricular myocardium of a patient's heart. The device also comprises an imagable member comprising an imagable material coupled to a housing or a lead configured, when viewed using two-dimensional imaging, to provide orientation information in a third dimension orthogonal to the two dimensions. The device further comprises a therapy delivery circuit operably coupled to the one or more electrodes to deliver cardiac therapy to the patient's heart; a sensing circuit operably coupled to the one or more electrodes to sense electrical activity of the patient's heart; and a controller comprising processing circuitry operably coupled to the therapy delivery circuit and the sensing circuit. The controller is configured to: sense electrical activity using the one or more electrodes; and deliver cardiac therapy based on the sensed electrical activity.

In illustrative embodiment B2, a device comprises a device according to any B embodiment, wherein the imagable material comprises radiopaque properties visible using fluoroscopy.

In illustrative embodiment B3, a device comprises a device according to any B embodiment, wherein the tissue-piercing electrode is implantable from the triangle of Koch region of the right atrium through the right atrial endocardium and central fibrous body to deliver cardiac therapy to or sense electrical activity of the left ventricle in the basal region, septal region, or basal-septal region of the left ventricular myocardium of the patient's heart.

In illustrative embodiment B4, a device comprises a device according to any B embodiment, wherein the one or more electrodes comprise a right atrial electrode positionable within the right atrium to deliver cardiac therapy to or sense electrical activity of the right atrium of the patient's heart.

In illustrative embodiment B5, a device comprises a device according to any B embodiment, wherein the tissue-piercing electrode is configured, when viewed using two-dimensional imaging, to provide orientation information in a third dimension orthogonal to the two dimensions of the two-dimensional imaging.

In illustrative embodiment B6, a device comprises a device according to any B embodiment, wherein the tissue-piercing electrode has a helical shape.

In illustrative embodiment B7, a device comprises a device according to any B embodiment, further comprising a housing, wherein the therapy delivery circuit, the sensing circuit, and the controller are located within the housing and the tissue-piercing electrode is leadlessly coupled to the housing.

In illustrative embodiment B8, a device comprises a device according to any embodiment B1-B6, further comprising: a housing, wherein the therapy delivery circuit, the sensing circuit, and the controller are located within the housing; and a lead coupled to and extending from the housing to a distal end region, wherein the tissue-piercing electrode and a right atrial electrode are coupled to the distal end region of the lead.

In illustrative embodiment B9, a device comprises a device according to any embodiment B1-B6, further comprising: a housing, wherein the therapy delivery circuit, the sensing circuit, and the controller are located within the housing; a first lead coupled to and extending from the housing to a first distal end region, wherein the tissue-piercing electrode is coupled to the first distal end region of the first lead; and a second lead coupled to and extending from the housing to a second distal end region, wherein a right atrial electrode is coupled to the second distal end region of the second lead.

In illustrative embodiment B10, a device comprises a device according to any embodiment B1-B6, further comprising: a housing, wherein the therapy delivery circuit, the sensing circuit, and the controller are located within the housing; a first lead coupled to and extending from the housing to a first distal end region wherein the tissue-piercing electrode is coupled to the first distal end region of the first lead; a second lead coupled to and extending from the housing to a second distal end region, wherein a right atrial electrode is coupled to the second distal end region of the second lead; and a third lead coupled to and extending from the housing to a third distal end region, wherein the one or more electrodes further comprise a right ventricular electrode to deliver cardiac therapy to or sense electrical activity of the right ventricle of the patient's heart coupled to the third distal end region of the third lead.

In illustrative embodiment C1, an implantation method comprises advancing an implantable medical device comprising a tissue-piercing electrode toward the triangle of Koch region of the right atrium through the right atrial endocardium and central fibrous body or through the coronary sinus to deliver cardiac therapy to or sense electrical activity of the left ventricle in the basal region, septal region, or basal-septal region of the left ventricular myocardium of a patient's heart, wherein the tissue-piercing electrode comprises an imagable material or the implantable medical device comprises an imagable member comprising an imagable material coupled to a housing or a lead of the implantable medical device. The method also comprises acquiring image information representing the patient's heart and the imagable material using two-dimensional imaging; and generating orientation information representing the implantable medical device based on the acquired image information.

In illustrative embodiment C2, a method comprises a method according to any C embodiment, further comprising implanting the implantable medical device in the triangle of Koch region of the right atrium of the patient's heart based on the generated orientation information representing the implantable medical device.

In illustrative embodiment C3, a method comprises a method according to embodiment C2, further comprising pointing the tissue-piercing electrode of the implantable medical device toward the apex of the patient's heart using a predetermined model of the patient's heart and the generated orientation information before advancing the tissue-piercing electrode into the right atrial endocardium and central fibrous body.

In illustrative embodiment C4, a method comprises a method according to any C embodiment, further comprising displaying on a display device the imagable material having at least one of a lowercase N-shape shape or a U-shape viewable in the two-dimensional imaging to indicate whether the implantable medical device is pointed toward or away from an imaging device used to acquire the image information.

In illustrative embodiment C5, a method comprises a method according to any C embodiment, wherein the two-dimensional imaging used is fluoroscopy.

In illustrative embodiment C6, a method comprises a method according to any C embodiment, further comprising determining, by processing circuitry, an orientation of the implantable medical device based on the generated orientation information.

In illustrative embodiment C7, a method comprises a method according to embodiment C6, wherein determining the orientation of the implantable medical device is based on a predetermined left-handed or right-handed winding of the tissue-piercing electrode comprising the imagable material or the imagable member comprising the imagable material.

Thus, various embodiments of IMPLANTABLE MEDICAL DEVICE DELIVERY FOR CARDIAC THERAPY are disclosed. Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

It will be understood that each block of the block diagrams and combinations of those blocks can be implemented by means for performing the illustrated function.

All references and publications cited herein are expressly incorporated herein by reference in their entirety into this disclosure, except to the extent they may directly contradict this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g., 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The term "and/of" means one or all of the listed elements or a combination of at least two of the listed elements.

The phrases "at least one of," "comprises at least one of," and "one or more of" followed by a list refers to any one of the items in the list and any combination of two or more items in the list.

What is claimed is:

1. An implantation method comprising:

advancing an implantable medical device comprising a tissue-piercing electrode toward the triangle of Koch region of the right atrium;

implanting the tissue-piercing electrode in the basal region, septal region, or basal-septal region of the left ventricular myocardium of a patient's heart, from the triangle of Koch region, through a region of the right atrial endocardium inferior to the His bundle, through the central fibrous body, wherein the tissue-piercing electrode comprises an imageable material or the implantable medical device comprises an imageable member comprising an imageable material coupled to a housing or a lead of the implantable medical device;

acquiring image information representing the patient's heart and the imageable material using two-dimensional imaging;

generating orientation information representing the implantable medical device based on the acquired image information; and delivering cardiac therapy to or sensing electrical activity of the left ventricle from the right atrium with the implantable medical device.

2. The method according to claim 1, wherein implanting the tissue-piercing electrode from the triangle of Koch region is based on the generated orientation information representing the implantable medical device.

3. The method according to claim 1, further comprising pointing the tissue-piercing electrode of the implantable medical device toward the apex of the patient's heart using the generated orientation information representing the implantable medical device.

4. The method according to claim 1, wherein generating orientation information comprises displaying on a display device the imageable material having at least one of a lowercase N-shape shape or a U-shape viewable in the two-dimensional imaging to indicate whether the implantable medical device is pointed toward or away from an imaging device used to acquire the image information.

5. The method according to claim 1, wherein the two-dimensional imaging used is fluoroscopy.

6. The method according to claim 1, further comprising determining, by processing circuitry, an orientation of the implantable medical device based on the generated orientation information.

7. The method according to claim 6, wherein determining the orientation of the implantable medical device is based on a predetermined left-handed or right-handed winding of the tissue-piercing electrode comprising the imageable material or the imageable member comprising the imageable material.

8. The method according to claim 3, wherein pointing the tissue-piercing electrode of the implantable medical device toward the apex of the patient's heart using the generated orientation information comprises adjusting the tissue-piercing electrode until the imageable member is oriented at an angle of 15 degrees or less relative to an imaging plane defined by the two-dimensional imaging.

9. The method according to claim 6, wherein the determined orientation of the implantable medical device includes orientation in a third dimension orthogonal to an imaging plane defined by the two-dimensional imaging.

10. The method according to claim 1, wherein the imageable material comprises a radiopaque material, and wherein the radiopaque material is more radiopaque than anatomical structures of the patient's heart.

11. The method according to claim 1, wherein, when the imageable member is aligned with an imaging plane defined by the two-dimensional imaging such that the imageable member is oriented at zero degrees relative to the imaging plane, and the imageable member displays as a sine wave.

12. The method according to claim 1, wherein, when the imageable member is oriented at an angle relative to an imaging plane defined by the two-dimensional imaging, the imageable member displays one or more loops.

13. The method according to claim 1, wherein, when the imageable member is oriented at positive fifteen degrees relative to an imaging plane defined by the two-dimensional imaging, the imageable member displays as a repeating U-shape, and wherein, when the imageable member is oriented at negative fifteen degrees relative to the imaging plane, the imageable member displays as a repeating lowercase N-shape or an arch.

14. The method according to claim 1, wherein when the imageable member is oriented at positive thirty degrees relative to an imaging plane defined by the two-dimensional imaging, the imageable member displays as a repeating U-shape with loops at a top of each U, and wherein when the imageable member is oriented at negative thirty degrees relative to the imaging plane, the imageable member displays as a repeating lowercase N-shape with loops at a bottom of each N.

15. The method according to claim 1, wherein when the imageable member is oriented at positive forty-five degrees relative to an imaging plane defined by the two-dimensional imaging, the imageable member displays as a repeating U-shape with loops at a top of each U, wherein the loops are larger than loops displayed at positive thirty degrees relative to the imaging plane, and wherein when the imageable member is oriented at negative forty-five degrees relative to the plane, the imageable member displays as a repeating lowercase N-shape with loops at a bottom of each N, wherein the loops are larger than loops displayed at negative thirty degrees relative to the imaging plane.

16. The method according to claim 1, further comprising acquiring additional image information representing the patient's heart using one or more of physiological data, two-dimensional, and three-dimensional imaging prior to advancing the implantable medical device, and advancing the implantable medical device based on the additional image information and the image information.

17. An implantation method comprising:

advancing an implantable medical device comprising a tissue-piercing electrode toward the triangle of Koch region of the right atrium;

implanting the tissue-piercing electrode in the basal region, septal region, or basal-septal region of the left ventricular myocardium of a patient's heart, from the triangle of Koch region, through a region of the right atrial endocardium inferior to the His bundle, through the central fibrous body, to deliver cardiac therapy to or sense electrical activity of the left ventricle from the right atrium, wherein the tissue-piercing electrode comprises an imageable material or the implantable medical device comprises an imageable member comprising an imageable material coupled to a housing or a lead of the implantable medical device;

acquiring image information representing the patient's heart and the imageable material using two-dimensional imaging; and generating orientation information representing the implantable medical device based on the acquired image information.

18. The method according to claim 17, further comprising pointing the tissue-piercing electrode of the implantable medical device toward the apex of the patient's heart using the generated orientation information representing the implantable medical device.

19. The method according to claim 17, further comprising displaying on a display device the imageable material, and when the imageable member is aligned with an imaging plane defined by the two-dimensional imaging, the imageable member is oriented at zero degrees relative to the imaging plane and the imageable member displays as a sine wave.

20. The method according to claim 17, further comprising displaying on a display device the imageable material, and when the imageable member is oriented at an angle relative to an imaging plane defined by the two-dimensional imaging, the imageable member displays one or more loops.

* * * * *